United States Patent
Al-Humam et al.

(10) Patent No.: US 11,035,009 B2
(45) Date of Patent: Jun. 15, 2021

(54) BIOCHIPS AND RAPID METHODS FOR DETECTING ORGANISMS INVOLVED IN MICROBIALLY INFLUENCED CORROSION (MIC)

(71) Applicant: Saudi Arabian Oil Company, Dhahran (SA)

(72) Inventors: Abdulmohsen A. Al-Humam, Dhahran (SA); Vitaly Zinkevich, Portsmouth (GB); Nelly Sapojnikova, Tbilisi (GE); Tamar Kartvelishvili, Tbilisi (GE); Nino Asatiani, Tbilisi (GE)

(73) Assignee: Saudi Arabian Oil Company, Dhahran (SA)

( * ) Notice: Subject to any disclaimer, the term of this patent is extended or adjusted under 35 U.S.C. 154(b) by 206 days.

(21) Appl. No.: 15/949,400

(22) Filed: Apr. 10, 2018

(65) Prior Publication Data

US 2018/0298429 A1    Oct. 18, 2018

Related U.S. Application Data

(60) Provisional application No. 62/484,672, filed on Apr. 12, 2017.

(51) Int. Cl.
*C07H 21/02* (2006.01)
*C12Q 1/689* (2018.01)
*B01J 19/00* (2006.01)

(52) U.S. Cl.
CPC .......... *C12Q 1/689* (2013.01); *B01J 19/0046* (2013.01); *B01J 2219/00529* (2013.01); *B01J 2219/00608* (2013.01); *C12Q 2600/16* (2013.01); *C12Q 2600/166* (2013.01)

(58) Field of Classification Search
None
See application file for complete search history.

(56) References Cited

U.S. PATENT DOCUMENTS

| | | | |
|---|---|---|---|
| 6,531,281 B1 | 3/2003 | Magot et al. | |
| 7,759,057 B2 | 7/2010 | Zhou et al. | |
| 2010/0323910 A1 | 12/2010 | Wunch et al. | |
| 2014/0024073 A1 | 1/2014 | Zhdaneev et al. | |

FOREIGN PATENT DOCUMENTS

| | | |
|---|---|---|
| CN | 105112543 | 12/2015 |
| IN | 2071MU2013 | 7/2015 |
| WO | WO2010/088500 | 8/2010 |

OTHER PUBLICATIONS

Abusam A., et al. (2002). Calibration and validation of a model for competition between methanogens and sulfate-reducers. In *Latin American Workshop and Symposium on Anaerobic Digestion*, 7(p. 8). UNAM. Available from: http://www.bvsde.paho.org/bvsacd/unam7/calibration.pdf.

Larsen J., et al. Consortia of MIC bacteria and archaea causing pitting corrosion in top side oil production facilities. *CORROSION 2010*, Mar. 14-18, 2010, San Antonio, TX, Conference Paper N 10252. Available from: http://www.onepetro.org/mslib/servlet/onepetropreview?id=NACE-10252.

Wolicka D., and Borkowski A. Microorganisms and Crude Oil. In: Introduction to Enhanced Oil Recovery (EOR) Processes and Bioremediation of Oil-Contaminated Sites. Dr. Laura Romero-Zerón (Ed.), ISBN: 978-953-51-0629-6, (2012) InTech, Available from: http://cdn.intechopen.com/pdfs/37040/InTech-Microorganisms_and_crude_oil.pdf.

Pruden A., et al. 7th International Conference on Acid Rock Drainage. Mar. 26-30, 2006. St. Louis, MO. Available from: http://www.docstoc.com/docs/41004784/Microbiology-of-Sulfate-Reducing-Passive-Treatment-Systems.

Daly K., et al. Development of oligonucleotide probes and PCR primers for detecting phylogenetic subgroups of sulfate-reducing bacteria. *Microbiology* (2000) 146:1693-1705.

Marshall Ipg., et al. The hydrogenase chip: a tiling oligonucleotide DNA microarray technique for characterizing hydrogen-producing and—consuming microbes in microbial community. *The ISME Journal* (2012) 6:814-826.

He Q., et al. Energetic consequences of nitrite stress in *Desulfovibrio vulgaris* Hildenborough, inferred from global transcriptional analysis. *Applied and Environ Microbiology* (2006) 72:4370-4381.

Caffrey SM., et al. Function of periplasmic hydrogenases in the sulfate-reducing bacterium *Desulfovibrio vulgaris* Hildenborough. *J Bacteriol* (2007) 189: 6159-6167.

Schmidt O., et al. Novel [NiFe]- and [FeFe]-hydrogenase gene transcripts indicative of active facultative aerobes and obligate anaerobes in earthworm gut contents. *Applied and Environ Microbiology* (2011) 77: 5842-5850.

Bodrossy L., et al. development and validation of a diagnostic microbial microarray for methanotrophs. Environ Microbiol (2003) 5:566-582.

Tiquia SM., et al. (2004) Evaluation of 50-mer oligonucleotide arrays for detecting microbial populations in environmental samples. *Biotechniques* 36: 664-675.

GeoChip 1-5; http://www.glomics.com/gch-tech.html. (Last accessed Jun. 16, 2015).

Magdalena K. Sztyler, Molecular Analysis of Microbial Communities from Oil Industry Environments; Thesis, University of Portsmouth, Institute of Biomedical and Biomolecular Sciences, May 2014.

He, Zhili, et al., GeoChip: A Comprehensive Microarray for Investigating Biogeochemical, Ecological and Environmental Processes. Int'l Society for Microbial Ecology, vol. 1: 67-77, 2007.

Rhee, S.K. et al. Detection of Genes Involved in Biodegradation and Biotransformation in Microbial Communities by Using 50-mer Oligonucleotide Microarrays. Appl. & Environ. Microbiol. vol. 70(7):4304-4307; Jul. 2004.

Xie, Jianping, et al., GeoChip-Based Analysis of the Functional Gene Diversity and Metabolic Potential of Microbial Communities in Acid Mine Drainage. Appl. & Environ. Microbiol. vol. 77 (3): 991-999. Feb. 2011.

(Continued)

Primary Examiner — Jehanne S Sitton
(74) Attorney, Agent, or Firm — Leason Ellis LLP

(57) ABSTRACT

The present invention relates to low-density biochips and methods for rapid detection of bacterial organisms involved in microbially influenced corrosion (MIC).

9 Claims, 22 Drawing Sheets

Specification includes a Sequence Listing.

(56) References Cited

OTHER PUBLICATIONS

Zhou, J., et al. High-Throughput Metagenomic Technologies for Complex Microbial Community Analysis: Open and Closed Formats. mBio. Jan./Feb. 2015, 6(1):e02288-14.

Loy, Alexander et al., Oligonucleotide Microarray for 16S rRNA Gene-Based Detection of All Recognized Lineages of Sulfate-Reducing Prokaryotes in the Environment. Appl. & Environ. Microbiol. vol. 68(10): 5064-5081, Oct. 2002.

Wu, L. et al. Development and Evaluation of Functional Gene Arrays for Detection of Selected Genes in the Environment. Appl. & Environ. Microbiol. vol. 67(12): 5780-5790, Dec. 2001.

Taroncher-Oldenburg, G. et al., Oligonucleotide Micraraay for the Study of Functional Gene Diversity in the Nitrogen Cycle in the Environment. Appl. & Environ. Microbiol. vol. 69(2): 1159-1171, Feb. 2003.

Zinkevich, Vitaly, and Iwona B. Beech. "Screening of sulfate-reducing bacteria in colonoscopy samples from healthy and colitic human gut mucosa." *FEMS microbiology ecology* 34.2 (2000): 147-155.

An, Xinli, et al. "The patterns of bacterial community and relationships between sulfate-reducing bacteria and hydrochemistry in sulfate-polluted groundwater of Baogang rare earth tailings." *Environmental Science and Pollution Research* 23.21 (2016): 21766-21779.

Hubert, Casey, et al. "Corrosion risk associated with microbial souring control using nitrate or nitrite." *Applied microbiology and biotechnology* 68.2 (2005): 272-282.

Hubert, Casey, and Gerrit Voordouw. "Oil field souring control by nitrate-reducing *Sulfurospirillum* spp. that outcompete sulfate-reducing bacteria for organic electron donors." *Applied and environmental microbiology* 73.8 (2007): 2644-2652.

Enning, Dennis, and Julia Garrelfs. "Corrosion of iron by sulfate-reducing bacteria—new views of an old problem." *Applied and environmental microbiology* (2013): AEM-02848.

Kleindienst, Sara, et al. "Distribution and in situ abundance of sulfate-reducing bacteria in diverse marine hydrocarbon seep sediments." *Environmental microbiology* 14.10 (2012): 2689-2710.

Zinkevich, Vitaly, et al. "A novel cassette method for probe evaluation in the designed biochips." *PloS one* 9.6 (2014): e98596.

Wu, Liyou et al. "Microarray-based analysis of subnanogram quantities of microbial community DNAs by using whole-community genome amplification" *Applied and environmental microbiology* vol. 72,7 (2006): 4931-41.

Schatz, Michael C et al. "Integrated microbial survey analysis of prokaryotic communities for the PhyloChip microarray" *Applied and environmental microbiology* vol. 76,16 (2010): 5636-8.

Klein, M et al. "Multiple lateral transfers of dissimilatory sulfite reductase genes between major lineages of sulfate-reducing prokaryotes" *Journal of bacteriology* vol. 183,20 (2001): 6028-35.

Vignais, Paulette M., and Bernard Billoud. "Occurrence, classification, and biological function of hydrogenases: an overview." *Chemical reviews* 107.10 (2007): 4206-4272.

Li, Xiangzhen, et al. "Metabolism of H2 by Desulfovibrio alaskensis G20 during syntrophic growth on lactate." *Microbiology* 157.10 (2011): 2912-2921.

Raskin, Lutgarde, et al. "Group-specific 16S rRNA hybridization probes to describe natural communities of methanogens." *Applied and environmental microbiology* 60.4 (1994): 1232-1240.

Bavykin, Sergei G., et al. "Portable system for microbial sample preparation and oligonucleotide microarray analysis." *Applied and environmental microbiology* 67.2 (2001): 922-928.

Tomalia, Donald A. "Birth of a new macromolecular architecture: dendrimers as quantized building blocks for nanoscale synthetic organic chemistry." *Aldrichimica Acta* 37.2 (2004): 39-57.

Lee, Cameron C., et al. "Designing dendrimers for biological applications." *Nature biotechnology* 23.12 (2005): 1517.

Balzani, Vincenzo. "Dendrimers: order, complexity, functions." *Australian Journal of Chemistry* 64.2 (2011): 129-130.

Breslauer, Kenneth J., et al. "Predicting DNA duplex stability from the base sequence." *Proceedings of the National Academy of Sciences* 83.11 (1986): 3746-3750.

Hager, Janet. "[7] Making and Using Spotted DNA Microarrays in an Academic Core Laboratory." *Methods in enzymology* 410 (2006): 135-168.

Zhou, Jizhong, and Dorothea K. Thompson. "Microarray technology and applications in environmental microbiology." (2004): 183-270.

| Position | Probe name | Position | Probe name | Position | Probe name |
|---|---|---|---|---|---|
| B2, C2 | Dtomoculum1 | B3, C3 | Dbacterium1 | B4, C4 | Dsmicrobium1 |
| D2, E2 | Dbulbus | D3, E3 | Dbacter2 | D4, E4 | Dv |

DNA –
*Desulfotomaculum ruminis, DSM 2154*

Probe –
*Dtomaculum1*

DNA –
*Desulfobulbus propionicus, DSM 2032*

Probe –
*Dbulbus*

| Position | Probe name | Position | Probe name | Position | Probe name |
|---|---|---|---|---|---|
| B2, C2 | 16SCONS_1 | B3, C3 | Dsmicrobium1 | B4, C4 | Dbacterium1 | B5, C5 | DV16S_1 |
| D2, E2 | SRB1 | D3, E3 | Dbacter2 | D4, E4 | Dbacterium16S_2 | D5, E5 | Dtomaculum1 |
| F2, G2 | Dv | F3, G3 | Dbacter2 | F4, G4 | Dbulbus | F5, G5 | Dscoccus |

| Position | Probe name | Position | Probe name | Position | Probe name | Sample A2 Position | Probe name |
|---|---|---|---|---|---|---|---|
| B2, C2 | Dv | B3, C3 | Dsmicrobium1 | B4, C4 | Dbulbus | B5, C5 | Dbacterium1 |
| D2, E2 | Dbacter2 | D3, E3 | Dtomaculum1 | D4, E4 | SRB | D5, E5 | 16SCONS_1 |
| F2, G2 | Dbacter1 | F3, G3 | Dtomaculum2 | F4, G4 | DSR2 | F5, G5 | Dscoccus1 |

| Position | Probe name | Position | Probe name | Position | Probe name | Position | Probe name | Position | Probe name |
|---|---|---|---|---|---|---|---|---|---|
| B2, C2 | 16SCONS_1 | B3, C3 | Dv_HynB2 | B4, C4 | Dv_1_hynA2 | B5, C5 | Dbacterium1 | B6, C6 | Dbacter1 |
| D2, E2 | SRB1 | D3, E3 | Dv_3_hynA2 | D4, E4 | Dv_2_hynA2 | D5, E5 | Dbacterium 16S_2 | D6, E6 | Dbacter2 |
| F2, G2 | Dv | F3, G3 | Dv 16S_1 | F4, G4 | Dv 16S_1 | F5, G5 | Dbulbus | F6, G6 | Dsmicrobium1 |
| H2, I2 | Dtomaculum1 | H3, I3 | Dtomaculum2 | H4, I4 | Dscoccus | | | | |

| Position | Probe name | Position | Probe name | Position | Probe name | Position | Probe name |
|---|---|---|---|---|---|---|---|
| B2, C2 | 16SCONS_1 | B3, C3 | Dbulbus | B4, C4 | Dbacterium1 | B5, C5 | nirk |
| D2, E2 | SRB1 | D3, E3 | Dsmicrobium1 | D4, E4 | Dbacterium16S_2 | D5, E5 | narG |
| F2, G2 | Dv16S_1 | F3, G3 | Dscoccus | F4, G4 | Dbacter1 | F5, G5 | NapA |
| H2, I2 | Dv | H3, I3 | Dtomaculum2 | H4, I4 | Dbacter2 | H5, I5 | nirS |

Sample A13

| Position | Probe name | Position | Probe name | Position | Probe name |
|---|---|---|---|---|---|
| B2, C2 | 16SCONS_1 | B4, C4 | Dv | B6, C6 | Dscoccus1 |
| D2, E2 | 16SCONS_2 | D4, E4 | Dbacterium1 | D6, E6 | Dv16S_1 |
| F2, G2 | 16SCONS_3 | F4, G4 | Dbulbus | F6, G6 | Dbacterium 16S_2 |
| H2, I2 | Geobac | H4, I4 | FTHFS | H6, I6 | narG |
| J2, K2 | GeoM | J4, K4 | a/bssA | J6, K6 | napA |
| L2, M2 | GeoS | L4, M4 | FirmicutishydA | | |
| B3, C3 | DSR1 | B5, C5 | Dtomaculum2 | | |
| D3, E3 | DSR2 | D5, E5 | Dsmicrobium1 | | |
| F3, G3 | SRB1 | F5, G5 | Dbacter2 | | |
| H3, I3 | 16SRNA PR | H5, I5 | nirK | | |
| J3, K3 | ShewRNA1 | J5, K5 | nirS | | |
| L3, M3 | Shew1 | L5, M5 | E. coli | | | ns

SEQUENCE LISTING

<160> NUMBER OF SEQ ID NOS: 85

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
ccagggcctg tccgccatca atac                                              24

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
gtgtagcagt taccgca                                                      17

<210> SEQ ID NO 3
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
acccactgga agcacg                                                       16

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
cacccctgca tcggctgcag                                                   20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cactggaaca ggcgatcaag                                                   20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
gcgccaccct gccgttcaac                                                   20

```
<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tcacctggtg aaaatcggac t                                              21

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
ccacaacctg gccatcccgg aaat                                           24

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
cacgcatcgg ggagagggtg g                                              21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
cacctcctcc aaaaccgggg aagg                                           24

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
caatccggac tgggacgg                                                  18

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gcgcgttgta cataccat                                                  18
```

```
<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
ccaggtggca tcaagttcgg acac                                            24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gtgctccccc gccaattcat                                                 20

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tgttgactac gtgttactga g                                               21

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
aggaattggc gggggagcac                                                 20

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
cacccggtgc actcctgga                                                  19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
acaactgccc aaccgagcgc                                                 20
```

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 19
ctcacgcact tcgggaccg                    19

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 20
ttcgggcctc ctgtctttc                    19

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 21
ttcgggcctt ttgtcacc                     18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic probe

<400> SEQUENCE: 22
cgcgattgga tgaacctag                    19

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic probe

<400> SEQUENCE: 23
agctaatccc acctaggtca                   20

<210> SEQ ID NO 24
<211> LENGTH: 18
<212> TYPE: DNA
<213> ORGANISM: Artificial Sequence
<220> FEATURE:
<223> OTHER INFORMATION: Description of Artificial Sequence: Synthetic probe

<400> SEQUENCE: 24
gtctgccgtg aaagtccg                     18

```
<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 25
tgcatggcca agacccaata cagc                                          24

<210> SEQ ID NO 26
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
tcgtcattgc cccatttggg ggc                                           23

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
aggcggcgag catgatccag caat                                          24

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
actcctgcgc gccaatccag                                               20

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
cgctgttcgt caagacccat ccg                                           23

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
cccgacccac gtcgtattca acgg                                          24
```

```
<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
ccagcttctt ctacgcccac accg                                          24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ccgcggctat gtgggtcgaa aaag                                          24

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
gacataaagg ccatgaggct g                                             21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
cagtgaggaa ttttgcgcac                                               20

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
gacgggcggt gtgtaca                                                  17

<210> SEQ ID NO 36
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
cctacgggag gcagcag                                                  17
```

```
<210> SEQ ID NO 37
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
attaccgcgg ctgctgg                                                    17

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
cggcaggcct aacacatgca agtcg                                           25

<210> SEQ ID NO 39
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
ccagggcctg tccgccatca atacaggaat tggcggggga gcacccaggt ggcatcaagt     60
tcggacac                                                              68

<210> SEQ ID NO 40
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gtgtccgaac ttgatgccac ctgggtgctc ccccgccaat tcctgtattg atggcggaca     60
ggccctgg                                                              68

<210> SEQ ID NO 41
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
cacccctgca tcggctgcag gcgccaccct gccgttcaac cacccggtgc actcctggaa     60
caactgccca accgagcgca ctcctgcgcg ccaatccag                            99

<210> SEQ ID NO 42
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 42
ctggattggc gcgcaggagt gcgctcggtt gggcagttgt tccaggagtg caccgggtgg    60
ttgaacggca gggtggcgcc tgcagccgat gcagggtg                            99

<210> SEQ ID NO 43
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 43
cagtgaggaa ttttgcgcac gacataaagg ccatgaggct gtgttgacta cgtgttactg    60
agcgcgattg gatgaaccta gagctaatcc cacctaggtc a                       101

<210> SEQ ID NO 44
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 44
tgacctaggt gggattagct ctaggttcat ccaatcgcgc tcagtaacac gtagtcaaca    60
cagcctcatg gcctttatgt cgtgcgcaaa attcctcact g                       101

<210> SEQ ID NO 45
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ttcgggcctt ttgtcacctt cgggcctcct gtctttcgtc tgccgtgaaa gtccggacgg    60
gcggtgtgta ca                                                        72

<210> SEQ ID NO 46
<211> LENGTH: 72
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
tgtacacacc gcccgtccgg actttcacgg cagacgaaag acaggaggcc cgaaggtgac    60
aaaaggcccg aa                                                        72

<210> SEQ ID NO 47
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtgctccccc gccaattcat ctcacgcact tcgggaccgg acgggcggtg tgtaca         56

```
<210> SEQ ID NO 48
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
tgtacacacc gcccgtccgg tcccgaagtg cgtgagatga attggcgggg gagcac       56

<210> SEQ ID NO 49
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
cagtgaggaa ttttgcgcac gtgctccccc gccaattcat ctcacgcact tcgggaccgt    60
tcgggccttt tgtcaccttc gggcctcctg tctttccgcg attggatgaa cctaggacgg   120
gcggtgtgta cagtctgccg tgaaagtccg                                    150

<210> SEQ ID NO 50
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 50
cggactttca cggcagactg tacacaccgc ccgtcctagg ttcatccaat cgcggaaaga    60
caggaggccc gaaggtgaca aaaggcccga acggtcccga agtgcgtgag atgaattggc   120
gggggagcac gtgcgcaaaa ttcctcactg                                    150

<210> SEQ ID NO 51
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51
cgctgttcgt caagacccat ccgccagctt cttctacgcc cacaccgccc gacccacgtc    60
gtattcaacg gccgcggcta tgtgggtcga aaaagtgcat ggccaagacc caatacagct   120
cgtcattgcc ccatttgggg gc                                            142

<210> SEQ ID NO 52
<211> LENGTH: 142
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52
gcccccaaat gggcaatga cgagctgtat tgggtcttgg ccatgcactt tttcgaccca     60
catagccgcg gccgttgaat acgacgtggg tcggcggtg tgggcgtaga agaagctggc   120
ggatgggtct tgacgaacag cg                                            142
```

```
<210> SEQ ID NO 53
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 53
cactggaaca ggcgatcaag tcacctggtg aaaatcggac tcacgcatcg gggagagggt      60
ggcacctcct ccaaaaccgg ggaaggccac aacctggcca tcccggaaat               110

<210> SEQ ID NO 54
<211> LENGTH: 110
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54
atttccggga tggccaggtt gtggccttcc ccggtttggg aggaggtgcc accctctccc      60
cgatgcgtga gtccgatttt caccaggtga cttgatcgcc tgttccagtg               110

<210> SEQ ID NO 55
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
caatccggac tgggacgggc gcgttgtaca taccatccta cgggaggcag cagattaccg      60
cggctgctgg cggcaggcct aacacatgca agtcg                                95

<210> SEQ ID NO 56
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cgacttgcat gtgttaggcc tgccgccagc agccgcggta atctgctgcc tcccgtagga      60
tggtatgtac aacgcgcccg tcccagtccg gattg                                95

<210> SEQ ID NO 57
<211> LENGTH: 119
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacataaagg ccatgaggct gcagtgagga attttgcgca cgtgctcccc cgccaattca      60
ttgttgacta cgtgttactg agaggaattg gcggggagc acgacgggcg gtgtgtaca      119

<210> SEQ ID NO 58
<211> LENGTH: 119
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 58
tgtacacacc gcccgtcgtg ctcccccgcc aattcctctc agtaacacgt agtcaacaat      60
gaattggcgg gggagcacgt gcgcaaaatt cctcactgca gcctcatggc ctttatgtc     119

<210> SEQ ID NO 59
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59
gtctgccgtg aaagtccgct cacgcacttc gggaccgttc gggccttttg tcaccttcgg      60
gcctcctgtc tttccgcgat tggatgaacc tagagctaat cccacctagg tca            113

<210> SEQ ID NO 60
<211> LENGTH: 113
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
tgacctaggt gggattagct ctaggttcat ccaatcgcgg aaagacagga ggcccgaagg      60
tgacaaaagg cccgaacggt cccgaagtgc gtgagcggac tttcacggca gac            113

<210> SEQ ID NO 61
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61 caccccctgca tcggctgcag gcgccaccct gccgttcaac cacgcatcgg ggagagggtg     60
gcacctcctc caaaaccggg aagg                                             85

<210> SEQ ID NO 62
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 62
ccttccccgg ttttggagga ggtgccaccc tctccccgat gcgtggttga acggcagggt      60
ggcgcctgca gccgatgcag gggtg                                            85

<210> SEQ ID NO 63
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide <210> SEQ ID NO 64
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ccacaacctg gccatcccgg aaatcactgg aacaggcgat caagtcacct ggtgaaaatc    60
ggact                                                                65

<210> SEQ ID NO 64
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
agtccgattt tcaccaggtg acttgatcgc ctgttccagt gatttccggg atggccaggt    60
tgtgg                                                                65

<210> SEQ ID NO 65
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cacccggtgc actcctggaa caactgccca accgagcgca ctcctgcgcg ccaatccaga    60
ggcggcgagc atgatccagc aat                                            83

<210> SEQ ID NO 66
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
attgctggat catgctcgcc gcctctggat tggcgcgcag gagtgcgctc ggttgggcag    60
ttgttccagg agtgcaccgg gtg                                            83

<210> SEQ ID NO 67
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
cgctgttcgt caagacccat ccgccagctt cttctacgcc cacaccgccc gacccacgtc    60
gtattcaacg gccgcggcta tgtgggtcga aaaag                               95

<210> SEQ ID NO 68
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 68 cttttttcgac ccacatagcc gcggccgttg aatacgacgt gggtcgggcg gtgtgggcgt    60
agaagaagct ggcggatggg tcttgacgaa cagcg                                95

<210> SEQ ID NO 69
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 69
ccagggcctg tccgccatca atactgcatg gccaagaccc aatacagctc gtcattgccc    60
catttggggg cccaggtggc atcaagttcg gacacgtgta gcagttaccg caacccactg   120
gaagcacg                                                            128

<210> SEQ ID NO 70
<211> LENGTH: 128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70
cgtgcttcca gtgggttgcg gtaactgcta cacgtgtccg aacttgatgc cacctgggcc    60
cccaaatggg gcaatgacga gctgtattgg gtcttggcca tgcagtattg atggcggaca   120
ggccctgg                                                            128

<210> SEQ ID NO 71
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
caaagggtgt ctgtacg                                                   17

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctcatggcat cccagaaatc                                                20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
cttgagacca tttcggttga                                                20
```

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
ggcgccgtta taggctgtag                                                20

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ctctacaaac tggggtgcaa g                                              21

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gacctttgcc ttggaaaaca                                                20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ccaggtctgt ccactgttcc                                                20

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
gtttcgccga agaacatga                                                 19

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgcccaatcc ctacaacct                                                 19

```
<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 80
acctatgccg attgtccccg                                               20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggaaattccg gactggtaca                                               20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gagggagtct tctccaagca                                               20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 83
cacccctgca tcgggtgcag                                               20

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
ctggatcgtc ctttcgatcg t                                             21

<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
tcacctggtg aaaatcggac t                                             21
```

BIOCHIPS AND RAPID METHODS FOR DETECTING ORGANISMS INVOLVED IN MICROBIALLY INFLUENCED CORROSION (MIC)

CROSS-REFERENCE TO RELATED APPLICATIONS

This present application claims priority to U.S. Provisional Patent Application Ser. No. 62/484,672 filed Apr. 12, 2017, which is incorporated herein by reference in its entirety.

SEQUENCE LISTING

The instant application contains a Sequence Listing which has been filed electronically in ASCII format and is hereby incorporated by reference in its entirety. Said ASCII copy, created on Apr. 11, 2017, and updated on Mar. 14, 2018, is named 00501-004193-US1_ST25.txt and is 22,480 bytes in size.

FIELD OF THE INVENTION

The present invention relates to low-density biochips and methods for rapid detection of bacterial organisms involved in microbially influenced corrosion (MIC).

BACKGROUND

Understanding the structure and composition of microbial communities and their responses to environmental perturbations such as toxic contamination, climate change, and agricultural and industrial practices is important for the maintenance and restoration of desirable ecosystem functions. However, due to the extremely high diversity of organisms, the detection, characterization, and quantification of microbial communities in environmental or industrial samples are formidable tasks for environmental biologists. Traditional culture-based enrichment techniques for studying microbial communities have proven difficult and ultimately, provide an extremely limited view of microbial community diversity and dynamics, because the majority of naturally occurring species cannot be cultured. Even for bacteria that can be cultured, the growth rate of the main MIC-causing bacteria (the sulfate-reducing bacteria (SRB)) typically requires from three to five weeks in culture. The development and application of nucleic acid-based techniques largely eliminated the reliance on cultivation-dependent methods and consequently, greatly advanced the detection and characterization of microorganisms in natural habitats. However, the limitations of conventional nucleic acid-based detection methods prevent them from being readily adapted as high-throughput, cost-effective assessment tools for monitoring complex microbial communities, and especially within the context of MIC.

DNA or oligonucleotide-based microarray technology is a powerful functional genomics tool that allows researchers to view the physiology of a living cell from a comprehensive and dynamic molecular perspective. Compared to traditional nucleic acid hybridization with porous membranes, glass slide-based microarrays, as well as 3-D arrays offer the additional advantages of high density, high sensitivity, rapid ("real-time") detection, automation, and low background levels. Target functional genes in environments tend to be highly diverse, and it is difficult, sometimes even experimentally impossible, to identify conserved DNA sequence regions for designing oligonucleotide probes for hybridization or primers for polymerase chain reaction (PCR) amplification. The microarray-based approach, however, does not require such sequence conservation, because all of the diverse gene sequences from different populations of the same functional group can be fabricated on arrays and used as probes to monitor their corresponding distributions in environmental samples.

Although microarray technology has been used successfully to analyze global gene expression in pure cultures, it is not clear whether it can be successfully adapted for use in complex and extreme environmental studies with sufficient specificity, sensitivity, and quantitative power [24]. First, in environmental samples, target and probe sequences can be very diverse, and it is not clear whether the performance of microarrays used with diverse environmental samples is similar to that with pure culture samples and how sequence divergence affects microarray hybridization. Second, unlike pure cultures, environmental samples are generally contaminated with substances such as humic matter, organic contaminants, and metals, which may interfere with nucleic acids-based molecular detection. Third, in contrast to pure cultures, the retrievable biomass in environmental samples is generally low. It is not clear whether microarray hybridization is sensitive enough for detecting microorganisms in environmental samples. Finally, since microarray-based hybridization has inherently high variability, it is uncertain whether microarray-based detection can be quantitative. Environmental and ecological studies often require experimental tools that not only detect the presence or absence of particular groups of microorganisms but also provide quantitative data on their in situ biological activities.

Based on the types of probes arrayed, microarrays used in environmental studies can be divided into three major classes: functional gene arrays (FGAs), community genome arrays (CGAs), and phylogenetic oligonucleotide arrays. FGAs contain probes corresponding to genes encoding key enzymes involved in various ecological and environmental processes, such as carbon fixation, nitrification, denitrification, sulfate reduction, and contaminant degradation [1-3]. Both PCR-amplified DNA fragments and oligonucleotides derived from functional genes can be used to fabricate FGAs. Thus, there are PCR product-based FGAs, as well as oligonucleotide-based FGAs. These types of arrays are useful in studying the physiological status and functional activities of microbial communities in natural environments. CGAs are constructed using whole genomic DNA isolated from pure-culture microorganisms and can be used to describe a microbial community in terms of its cultivable component [4]. Phylogenetic oligonucleotide arrays are constructed with short synthetic oligonucleotides from rRNA genes and can be used for phylogenetic analyses of microbial-community composition and structure in environmental samples [5].

Thus, novel microarray-based methods that will allow quantitative and sensitive analysis of microbial communities, especially less abundant populations in environments such as MIC, in a relatively quick and inexpensive manner, are desirable.

SUMMARY OF INVENTION

In certain embodiments, the present disclosure relates to an oligonucleotide probe set suitable for detection, identification, or quantification of corrosion causing bacteria in a sample, comprising a plurality of probes from Table 1, Table 3, Table 4, Table 5, or any combination thereof. In certain embodiments, the probes can be combined into one or more combinations of cassettes exemplified in Table 2.

In certain embodiments, the probes comprise SRB1, Dv, Dbacterium1, Dbulbus, Dbacter2, Dbacter1, Dsmicrobium1, Dtomaculum1, Dtomaculum2, Dscoccus, Dv 16S_1, MCR1, Archaea1, Archaea2, ARC16SRNA, Geobac, Shew, GeoS, GeoM, ShewRNA1, 16SRNA PR, FTHFS, a/bssA, Firmicutishyd A, *E. coli*, nirS, nirK, narG, and napA. (SEQ ID NOs: 1; 4; 5-11; 13-18; 20-22; 24-32; 80; and 84).

In certain embodiments, the probes of the set are immobilized at identifiable locations on a biochip.

In certain embodiments, the probe set further comprises a positive control probe 16SCONS_1 (SEQ ID NO:36).

In additional embodiments, the present disclosure relates to a method for determining a bacterial community composition, said method comprising the steps of:
(a) providing target DNA to be analyzed;
(b) subjecting said target DNA to $1^{st}$ amplification;
(c) fragmenting amplified target DNA;
(d) subjecting fragmented target DNA to $2^{nd}$ amplification step and labeling the target DNA;
(e) hybridizing said fragments of labeled target DNA with a BioChip comprising the oligonucleotide probe set described herein.
(f) quantifying hybridization efficiency of target DNA fragment to the oligonucleotide probe set described herein, wherein hybridization efficiency of >1.5 indicates successful hybridization.

In certain embodiments, the target DNA is single stranded.

In additional embodiments, oligonucleotide probes are immobilized on a solid support.

In additional embodiments, hybridization of at least 21 probes is indicative of corrosion causing bacterial activity.

In additional embodiments, the present disclosure relates to a BioChip comprising oligonucleotide probes from Table 1, Table 3, Table 4, Table 5, or any combination thereof, immobilized on a solid support, for detecting bacteria associated with microbially influenced corrosion (MIC).

In certain embodiments, the bacteria are selected from the group consisting of SRB: (*Desulfovibrio, Desulfobacterium, Desulfobulbus, Desulfobacter, Desulfomicrobium, Desulfotomaculum ruminis, Desulfotomaculum, Desulfococcus*); Methanogenic Archaea); MRB: (*Geobacter* spp.; *Shewanella* spp.; *G. sulfurreducens; G. metallireducens; Arthrobacter* spp.); FB: (Acetogenic, Hydrocarbon-degrading, Firmicutes); *E. coli*, and NRB.

In certain embodiments, the probes are selected from the group consisting of SRB1, Dv, Dbacterium1, Dbulbus, Dbacter2, Dbacter1, Dsmicrobium1, Dtomaculum1, Dtomaculum2, Dscoccus, Dv 16S_1, MCR1, Archaea1, Archaea2, ARC16SRNA, Geobac, Shew, GeoS, GeoM, ShewRNA1, 16SRNA PR, FTHFS, a/bssA, Firmicutishyd A, *E. coli*, nirS, nirK, narG, napA, and 16SCONS_1. (SEQ ID NOs: 1; 4; 5-11; 13-18; 20-22; 24-32; 80; 84; and 36).

In certain embodiments, the solid support comprises a 3D-matrix material. In certain embodiments, the 3D-matrix material is dendrimer.

In additional embodiments, the present disclosure relates to a method of preparing a DNA sample for analysis comprising the following steps:
(a) amplifying the DNA sample;
(b) purifying the amplified DNA;
(c) fragmenting the purified and amplified DNA;
(d) purifying the fragmented and amplified DNA;
(e) amplifying the purified DNA a second time and labeling the DNA;
(f) hybridization of the labeled DNA from step e) with a set of probes.

In certain embodiments, step (a) is performed at 25° C. for four hours.

In additional embodiments, fragmenting of the purified and amplified DNA is performed by a restriction enzyme that recognizes T^TAA site. In certain embodiments, fragmenting of the purified and amplified DNA is performed using fragmentase or SaqAI.

In certain embodiments, hybridization is performed at 25° C. for 4 hours.

In additional embodiments, the present disclosure relates to a kit suitable for performing an assay that detects, identifies and/or quantitates corrosion causing bacteria in a sample, wherein said kit comprises: a) the probes from Table 1, Table 3, Table 4, Table 5, or any combination thereof, or the cassettes of Table 2, and optionally, b) additional reagents or compositions necessary to perform the assay.

In certain embodiments, the corrosion causing bacteria are selected from the group consisting of SRB: (*Desulfovibrio, Desulfobacterium, Desulfobulbus, Desolfobacter, Desulfomicrobium, Desulfotomaculum ruminis, Desulfotomaculum, Desulfococcus*); Methanogenic Archaea; MRB: (*Geobacter* spp.; *Shewanella* spp.; *G. sulfurreducens; G. metallireducens; Arthrobacter* spp.); FB: (Acetogenic, Hydrocarbon-degrading, Firmicutes); *E. coli*, and NRB.

In certain embodiments, the kit further comprises a positive control probe 16SCONS_1 (SEQ ID NO:36).

In certain embodiments, the additional reagents or compositions comprise one or more of the following: sample buffer, reaction buffer, enzyme mix, Fragmentase reaction buffer, nucleotide mix, 1M GuSCN, 5 mM EDTA, or 50 mM HEPES (pH 7.5).

In yet additional embodiments, the present disclosure relates to an oligonucleotide probe set suitable for detection of bacteria associated with corrosion, comprising at least one or more of the following:
a) probes selected from the group consisting of SRB1, Dv, Dbacterium1, Dbulbus, Dbacter1, Dbacter2, Dmicrobium1, Dmaculum1, Dtomaculum2, Dscoccus, and Dv 16S_1 (SEQ ID Nos:1; 4; 5-7; 84; 8; 80; 9-11);
b) probes selected from the group consisting of the following: MCR1, Archaea1, Archaea2, and ARC16SRNA (SEQ ID Nos: 13-16);
c) probes selected from the group consisting of the following: Geobac, Shew, GeoS, GeoM, ShewRNA1, and 16SRNA PR (SEQ ID Nos:17-18; 20-22; and 24);
d) probes selected from the group consisting of the following: FTHFS, a/bssA, and Firmicutishyd A; and *E. coli* (SEQ ID Nos:25-28);
e) probes selected from the group consisting of the following: nirS, nirK, narG, and napA (SEQ ID NOs: 29-32) and
f) probe selected from the group consisting of the following: 16SCONS_1 (SEQ ID NO:36).

In additional embodiments, the present disclosure relates to an oligonucleotide probe set suitable for detection of combination of bacteria associated with corrosion, comprising at least one or more of the following:
a) 11 probe(s) selected from the group consisting of SRB1, Dv, Dbacterium1, Dbulbus, Dbacter1, Dbacter2, Dmicrobium1, Dmaculum1, Dtomaculum2, Dscoccus, and Dv 16S_1 (SEQ ID Nos:1; 4; 5-7; 84; 8; 80; 9-11);
b) 4 probe(s) selected from the group consisting of the following: MCR1, Archaea1, Archaea2, and ARC16SRNA (SEQ ID Nos:13-16);

c) 6 probe(s) selected from the group consisting of the following: Geobac, Shew, GeoS, GeoM, ShewRNA1, and 16SRNA PR (SEQ ID Nos:17-18; 20-22; and 24);

d) 4 probe(s) selected from the group consisting of the following: FTHFS, a/bssA, and Firmicutishyd A; and *E. coli* (SEQ ID Nos:25-28);

e) 4 probe(s) selected from the group consisting of the following: nirS, nirK, narG, and napA (SEQ ID NOs: 29-32) and f) 1 probe(s) selected from the group consisting of the following: 16SCONS_1 (SEQ ID NO:36).

In additional embodiments, the present disclosure relates to a method of detecting corrosion in a sample, said method comprising:

(a) obtaining a DNA sample;

(b) detecting whether corrosion causing bacteria is present in the DNA sample by contacting the DNA sample with one or more of the following probes: SRB1, Dv, Dbacterium1, Dbulbus, Dbacter2, Dbacter1, Dsmicrobium1, Dtomaculum1, Dtomaculum2, Dscoccus, Dv 16S_1, MCR1, Archaea1, Archaea2, ARC16SRNA, Geobac, Shew, GeoS, GeoM, ShewRNA1, 16SRNA PR, FTHFS, a/bssA, Firmicutishyd A, *E. coli*, nirS, nirK, narG, and napA (SEQ ID NOs: 1; 4; 5-11; 13-18; 20-22; 24-32; 80; and 84) detecting a hybridization signal between DNA sample and individual probes; and (c) establishing the presence of corrosion when the presence of at least one corrosion causing bacteria is detected.

In additional embodiments, the method further comprises increasing the amount of one or more nitrate reducing bacteria (NRB) that comprise nitrate or nitrite reductase genes selected from the group consisting of narG, nirS/nirK, and napA in a surface or liquid environment from which the sample was obtained.

In additional embodiments, the present disclosure relates to a method of detecting corrosion susceptibility in a sample, said method comprising:

(a) obtaining a DNA sample;

(b) detecting whether corrosion causing bacteria is present in the DNA sample by contacting the DNA sample with one or more of the following probes: SRB1, Dv, Dbacterium1, Dbulbus, Dbacter2, Dbacter1, Dsmicrobium1, Dtomaculum1, Dtomaculum2, Dscoccus, Dv 16S_1, MCR1, Archaea1, Archaea2, ARC16SRNA, Geobac, Shew, GeoS, GeoM, ShewRNA1, 16SRNA PR, FTHFS, a/bssA, Firmicutishyd A, *E. coli*, nirS, nirK, narG, and napA (SEQ ID NOs: 1; 4; 5-11; 13-18; 20-22; 24-32; 80; and 84) and detecting a hybridization signal between DNA sample and Individual probes; and (c) establishing the presence of corrosion susceptibility when the presence of at least one corrosion causing bacteria is detected.

In yet additional embodiments, the method further comprises increasing the amount of one or more nitrate reducing bacteria (NRB) that comprise nitrate or nitrite reductase genes selected from the group consisting of narG, nirS/nirK, and napA in a surface or liquid environment from which the sample was obtained.

In yet additional embodiments, the present disclosure relates to a method of detecting corrosion-causing microorganisms in a sample, the method comprising:

(a) obtaining DNA from the sample; and (b) detecting corrosion-causing microorganisms in the sample by contacting the DNA with one or more probes that hybridize to one or more genes encoding (i) one or more reductases, (ii) one or more hydrogenases, and/or (iii) 16S rRNA.

In certain embodiments, the one or more reductases comprise a nitrite reductase, and/or a nitrate reductase. In additional embodiments, the one or more hydrogenases comprise a periplasmic NiFe-hydrogenase, a membrane-bound NiFe-hydrogenase, a Fe-hydrogenase, hydrogenase accessory protein HypB, or combinations thereof. In yet additional embodiments, the genes comprise apr; hynAB; hydA (NiFe); hydA (Fe); hypB, or combinations thereof.

In further embodiments, the genes comprise mcr, hydA (NiFe), or a combination thereof.

In further embodiments, the genes comprise mcr; hydA (NiFe); fthfs; a/bssA; hydA (Fe); hyaA; nirS; nirK; narG; napA, or combinations thereof.

In further embodiments, the genes comprise apr; hynAB; hydA (NiFe); hydA (Fe); hypB; hyaA; mcr; fthfs; a/bssA; nirS; nirK; narG; napA, 16S rRNA, or combinations thereof.

In further embodiments, the genes comprise dsr, apr, hynB (NiFe), hydA (NiFe), hydA(Fe), hypB, 16S rRNA, or combinations thereof.

In yet further embodiments, the genes comprise dsr, apr, hynB, hydA(Fe), hydA(NiFe), mcr, fthfs, assA/bssA, hyaA, nirS; nirK; narG; napA, 16S rRNA, or combinations thereof.

In further embodiments, the genes encode one or more of the following: methyl coenzyme M reductase from *Archaea*; a hydrogenase from metal-reducing bacteria (MRB); fthf, assA/bssA, and hydA from fermentative bacteria (FB), narG, nirS, nirK, and napA from nitrate reducing bacteria (NRB), and hyaA from *E. coli*.

In further embodiments, the corrosion-causing microorganisms are selected from sulfate-reducing bacteria (SRB), *methanogenic archaea*, nitrate-reducing bacteria (NRB), metal-reducing bacteria (MRB), fermentative bacteria (FB).

In further embodiments, the corrosion-causing microorganisms are selected from the group consisting of SRB: (*Desulfovibrio, Desulfobacterium, Desulfobulbus, Desolfobacter, Desulfomicrobium, Desulfotomaculum ruminis, Desulfotomaculum, Desulfococcus*, Methanogenic Archaea; Archaea); MRB: (*Geobacter* spp.; *Shewanella* spp.; *G. sulfurreducens; G. metallireducens; Arthrobacter* spp.); FB: (Acetogenic, Hydrocarbon-degrading, Firmicutes); *E. coli*, NRB, and combinations thereof.

In further embodiments, the probes comprise one or more of the following: SEQ ID NOs: 1; 4; 5-11; 13-18; 20-22; 24-32; 80; and 84.

BRIEF DESCRIPTION OF THE FIGURES

FIG. 4A shows the arrangement of the probes on the biochip. Dark grey circles are the probes position markers. FIG. 4B represents the analysis of hybridization. The results of the hybridization are presented as signal to noise (S/N) ratios. FIG. 4C is the hybridization image for the probe Dtomaculum1 for *Desulfotimaculum ruminis*. FIG. 4D shows the hybridization image for the probe Dbulbus for *Desulfobulbus propionicus*. FIG. 4E is the hybridization image for the probe Dbacterium1 for *Desulfobacterium autotropicum*. FIG. 4F shows the hybridization image for the probe Dbacter2 for *Desulfobacter postgatei*. FIG. 4G is the hybridization image for the probe Dmicrobium1 for *Desulfomicrobium baculatum*. FIG. 4H shows the hybridization image for the probe Dv for *Desulfovibrio alaskensis*. The data are results of two independent experiments.

FIG. 6A is an image showing the arrangement of the probes on the BioChip. Dark grey circles along the edge of the biochip indicate probes position markers. FIG. 6B is the image of hybridization of *Desulfobacterium autotropicum*. FIG. 6C is a bar graph showing the hybridization signal, presented as signal to noise ratio for each probe on the biochip.

FIG. 7A shows the arrangement of the probes on the biochips. The dark circles along the edge of the biochip are the probes position markers. FIG. 7B shows the hybridization image. FIG. 7C shows the hybridization signal, presenting as signal to noise ratio, for the probes on the biochip. DNA (5.5 µg, 163 pmol Alexa555) was dissolved in 7 µl of HBB+BSA hybridization buffer. After hybridization at 25° C. for 4 h and washing, the biochips were imaged with the Portable Imager 5000 for 0.5 s of exposure.

FIG. 8A shows the arrangement of the probes on the biochips. The dark circles along the edge of the biochip are the probe position markers. FIG. 8B shows the hybridization image. FIG. 8C shows the hybridization signal, presenting as signal to noise ratio, for the probes on the prototype biochip. DNA (2.5 µg, 125 pmol Alexa555) was dissolved in 10 µl of HBB+BSA hybridization buffer. After hybridization at 25° C. for 4 h and washing, the biochips were imaged with the Portable Imager 5000 for 0.5 s of exposure.

FIG. 9A shows the arrangement of the probes on the biochips. FIG. 9B shows the hybridization image. FIG. 9C shows the hybridization signal, presenting as signal to noise ratio, for the probes.

FIG. 10A shows the arrangement of the probes on the biochips. The dark circles along the edge of the biochip are the probes position markers. FIG. 10B shows the hybridization image. FIG. 10C shows the hybridization signal, presenting as signal to noise ratio, for the probes on the biochip. DNA (6.75 µg, 246 pmol Alexa555) was dissolved in 24 µl of HBB+BSA hybridization buffer. After hybridization at 25° C. for 4 h and washing, the biochips were imaged with the Portable Imager 5000 for 5 s of exposure. PC is positive control.

DETAILED DESCRIPTION OF THE INVENTION

A large group of bacteria contribute to MIC of metal products, coatings based on iron, aluminum, manganese, iron, and even stainless steel and plastic and rubber products, which typically are in contact with water in diverse industries, such as the chemical industry (tanks, pipelines), the nuclear industry (pipes and tanks for cooling water), oil and gas industry (underground and surface), the aviation industry (fuel tanks, aluminum one-piece wing tanks), and the marine and shipbuilding industry (accelerated damage of ships and barges).

The economic loss associated with metal corrosion is huge ~$200 billion per year (loss of time, loss of production, penalty charges, cleaning). The contribution of bacterial corrosion in different areas of the industry is estimated to be 10-77%. Identifying the extremely active microbes to determine potential sites of biocorrosion development and monitoring sites for potential intervention have proved difficult.

Figure 11:
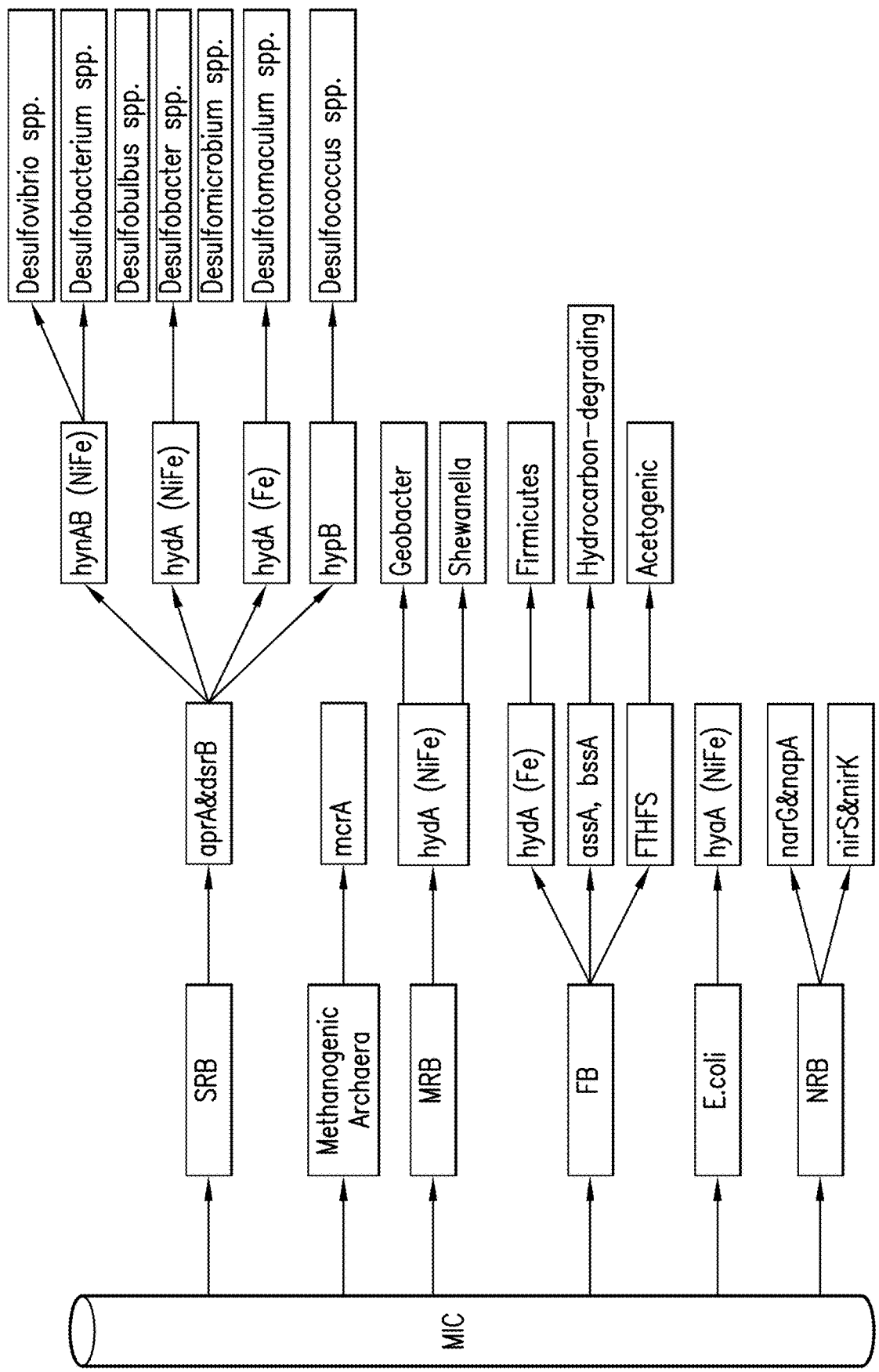
FIG. 11 is a flow chart illustrating combinations of genes to be used for probes in low-density MIC BioChips for evaluating microbial communities.

Embodiments of the present invention relate to a BioChip, more particularly, a low-density MIC BioChip based system utilizing detection of certain functional genes, whose products are involved in metabolic pathways related to microbially influenced corrosion (MIC). In certain aspects, the low-density MIC BioChip and related methods rely on detecting a combination of reductases and hydrogenases associated with MIC. In additional embodiments, the method further includes detecting nitrate reducing bacteria (NRB) (i.e., their nitrate and/or nitrite reductase genes), which are inhibitors of corrosion. Thus, embodiments of the proposed low-density MIC BioChip will be designed to detect at least 13 functional genes (at least 21 probes, and optionally additional genes as described, as shown in Table 5) encoding hydrogenases and reductases from four groups of sulfate-reducing bacteria (SRB), as well as optional genes encoding methyl coenzyme M reductase from *Archaea*, genes encoding hydrogenases from metal-reducing bacteria (MRB), genes encoding fthf, assA/bssA, and hydA from fermentative bacteria (FB), genes encoding narG, nirS/nirK, and napA from nitrate reducing bacteria (NRB), as well as hydrogenase gene hyaA from *E. coli* (as shown in FIG. 11). Thus, in certain embodiments, at least 13 functional genes (21 probes) are utilized for accurate detection, this is a minimum number required for accurate detection. The functional genes are: apr; hynAB; hydA (NiFe); hydA (Fe); hypB; hyaA; mcr; fthfs; a/bssA; nirS; nirK; narG; napA (shown in Table 5). The probes are: Numbers 1-10; 12; 16; 17; 22-29 (as shown in Table 5).

In additional embodiments, an extended variant of the MIC BioChip has 14 genes: 13 functional genes: apr; hynAB; hydA (NiFe); hydA (Fe); hypB; hyaA; mcr; fthfs; a/bssA; nirS; nirK; narG; napA and 16SrRNA gene (30 probes) (Table 5). 16SrRNA gene and 9 probes for the different bacteria are included as additional verifying features.

Thus, in additional embodiments, the method further includes detecting structural genes based on the 16S rRNA. Examples of such probe sets can be found at least in Table 1, Table 3, Table 4 and Table 5. Probes from any of these tables can be combined, as described below to detect the bacteria of interest as described herein.

The nitrate-reducing population may work to oppose SRB corrosion activity by the following pathways: 1) nitrite (product of nitrate reductase), but not nitrate inhibits the enzyme dissimilatory sulfite reductase [Hubert C., et al. *Corrosion risk associated with microbial souring control using nitrate and nitrite. Environmental Biotechnology* (2005) 68:272-282]; 2) the intermediates of nitrite reduction by nitrite reductase, nitrous oxide and nitric oxide, increase the ambient redox potential. Biological sulfide production does not occur when the redox potential is above −100 mV, and the growth of SRB can be inhibited by elevation of the redox potential [Postgate J R. *The Sulphate-Reducing Bacteria* (1979) *Cambridge University Press, Cambridge*]; 3) the intermediates of nitrite reduction by nitrite reductase inhibits the enzyme hydrogenase [Haruna S., et al. *The functional complexity of [NiFe] hydrogenases in sulfate reducing bacteria* (genus; *Desulfovibrio* spp). *American J Bioscience & Bioengineering* (2014) 2:1-7]; 4) soil sulfate reduction does not begin before the environment becomes exhausted of nitrates [He Q., et al. *Energetic consequences of nitrite stress in Desulfovibrio vulgaris Hildenborough, inferred from global transcriptional analysis. Applied and Environ Microbiology* (2006) 72:4370-4381]. Therefore, the detection the nitrate reductase genes (narG, napA) and nitrite reductase genes (nirk, nirS) using the MIC Biochip described herein works to characterize the status of nitrate-reducing population (NRB). The corresponding probes from the genes narG, napA, nirk and nirS are provided in Table 5.

In certain embodiments, the present invention provides for simultaneous detection of target nucleic acids in a sample. One of the major challenges in designing DNA probes that can be used simultaneously with other DNA is the variation in the conditions necessary for proper hybridization between the DNA probe and nucleic acid target, requiring each hybridization reaction to be carried out individually. Thus, probes that can be used simultaneously require identical hybridization characteristics. In aspects of the present invention, inventors used a novel method to evaluate BioChip probes in one reaction, using DNA cassettes, comprising all of the probes in equimolar proportions for a quick determination of the probes unsuitable for inclusion in the pilot biochip [23]. This allowed for the design of probes with identical hybridization characteristics. Thus, embodiments of the pilot BioChip of the present disclosure offer the ability to achieve simultaneous detection of many DNA targets without detriment to sensitivity.

Additional embodiments of the present invention include using the low-density MIC BioChip to obtain an estimated MIC microorganism ratio based upon detecting selected gene products from bacteria which contribute to corrosion, in combination with gene products from bacteria that inhibit or resist corrosion (e.g., nitrate reducing bacteria (NRB) and their nitrate and/or nitrite reductase genes). Based on these ratios, a corrosion scale can be developed based upon the quantity of MIC sustaining, inducing, or opposing bacteria present in the sample. In certain aspects, the present invention relates to estimating MIC microorganism ratios based upon detecting the select genes from bacteria which contribute to corrosion, in combination with genes from bacteria that inhibit or resist corrosion. For example, the MIC Biochip can detect and illustrate that Group I bacteria (Group I consists of *Desulfovibrio* and *Desulfobacterium*) dominate in the SRB (mostly, the corrosion of underground steel structures is caused by the genus *Desulfovibrio*), and if the signals from all the other bacterial groups are less, it means that this area is at the high-risk of corrosion. If detection of the bacteria from Groups II, III, IV are high, and Group I bacteria exhibit little or no signal, it indicates that this sample location/place is in the medium-risk of corrosion. The lowest risk areas are the places where the Group IV bacteria dominate. The use of the MIC biochip will allow for detecting the linkage between the bacterial diversity and degree of corrosion. On the basis of these results index maps of corroding regions can be developed and serve as a prognostic tool.

Figure 12A:
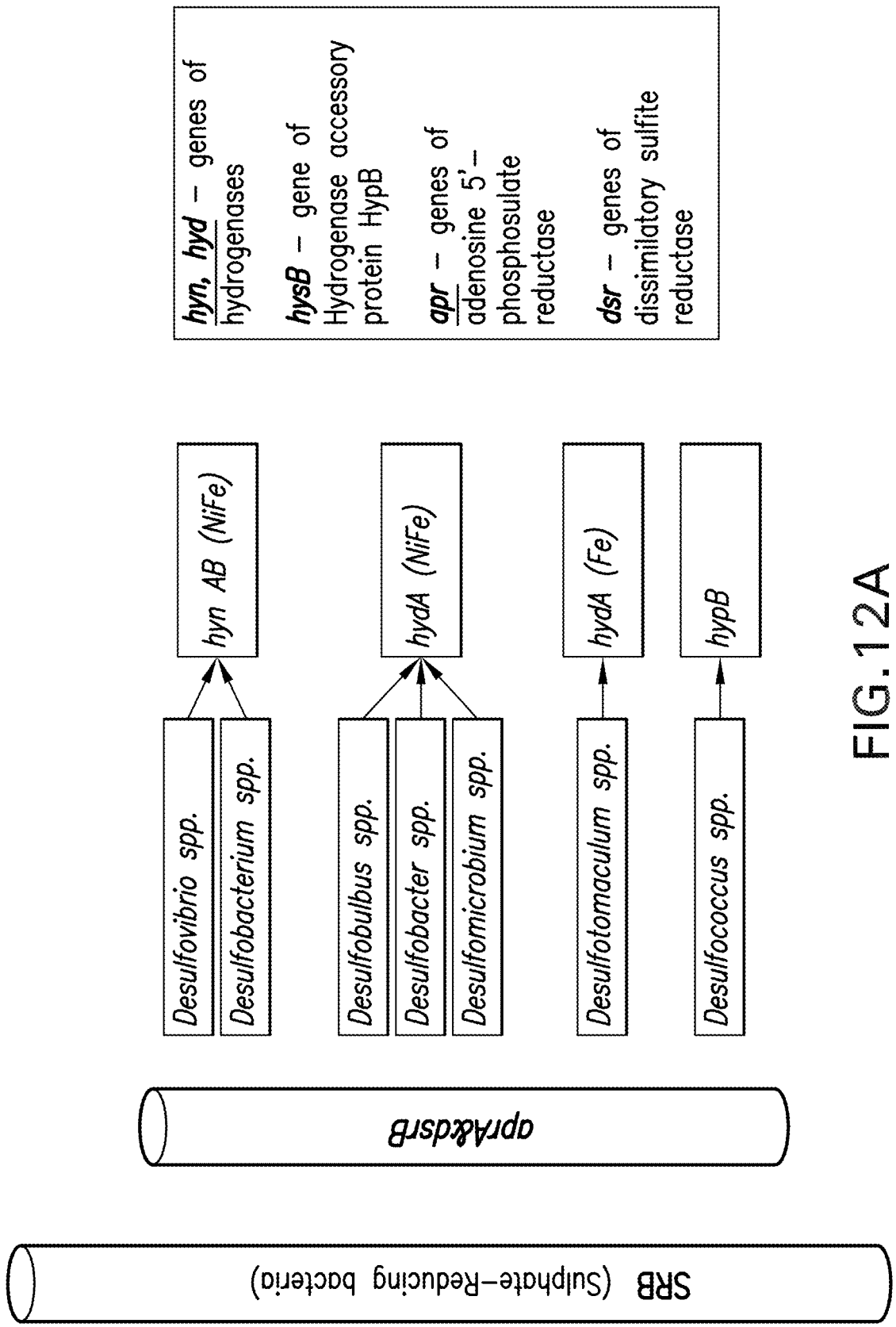
FIGS. 12A-C are flow charts illustrating select genes from sulfate-reducing bacteria, *Archaea*, and metal-reducing bacteria for assessing MIC.

An aspect of the present invention relates to evaluating SRB effects on corrosion by dividing the SRB into four groups and detecting one or more of the following hydrogenase genes using the MIC BioChip (as shown in FIG. 12A):

Group I *Desulfovibrio* and *Desulfobacterium* (Periplasmic (NiFe) hydrogenase);
Group II *Desulfobulbus, Desulfobacter* and *Desulfomicrobium* (Membrane-bound (NiFe) hydrogenase)
Group III *Desulfotomaculum* ((Fe) hydrogenase)
Group IV *Desulfococcus* (Hydrogenase accessory protein HypB; hypB gene).

Figure 12B:
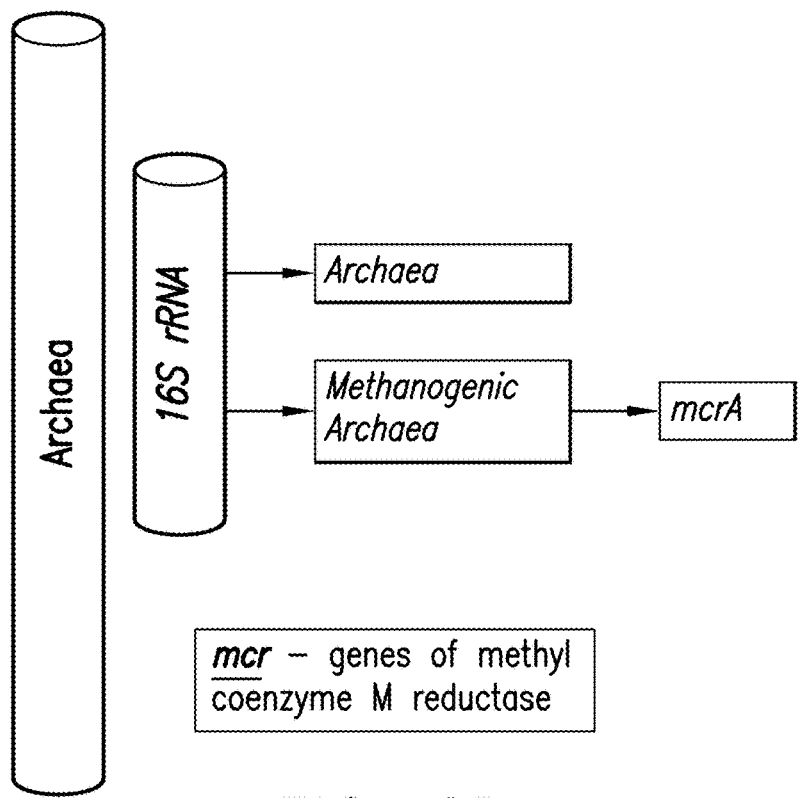

The minimum gene panel for detecting the SRBs consists from 5 genes apr; hynAB; hydA (NiFe); hydA (Fe); hypB; (10 probes) (Table 5). The microbial populations in addition to SRB, actively participating in biocorrosion processes, are Methanogenic Archaea and metal-reducing bacteria (MRB) (FIGS. 12 A-C). The detection of these two groups of microorganisms is based on the 2 genes mcr and hydA (NiFe) (3 probes). Therefore, the minimal panel for the detection the main players based on the degree of involvement in MIC (SRB, *Archaea* and MRB) consists of 7 genes (13 probes) (Table 5).

Thus, embodiments of low-density MIC BioChips and related methods provide an improved approach for determining the bacterial community contributing to potentially corrosive conditions in a variety of drilling/water/storage environments. These methods and BioChip compositions/arrays provide for high specificity while utilizing fewer probes. Advantages associated with these methods include speed of detection (e.g. 2-3 days); no requirement for cultures; unique bacterial community quantification; and an alternative to expensive chips containing thousands of genes. Further advantages also include simultaneous detection of these distinct genes based at least in part upon probe and hybridization optimizations as described herein.

The terms "nucleic acid" and "polynucleotide" are used interchangeably herein to describe a polymer of any length, e.g., greater than about 2 bases, greater than about 10 bases, greater than about 100 bases, greater than about 500 bases, greater than about 1,000 bases, up to about 10,000 or more bases composed of nucleotides, e.g., deoxyribonucleotides or ribonucleotides, which can hybridize with nucleic acids in a sequence specific manner analogous to that of two naturally occurring nucleotides, e.g., can participate in Watson-Crick base pairing interactions. Naturally-occurring nucleotides include guanine, cytosine, adenine and thymine (G, C, A and T, respectively).

The terms "hybridize" or "hybridization", as used herein, refer to the binding or duplexing of a nucleic acid molecule to a particular nucleotide sequence under suitable conditions.

The term "complementary", as used herein, refers to a nucleotide sequence that base-pairs by non-covalent bonds to a target nucleic acid of interest. In the canonical Watson-Crick base pairing, adenine (A) forms a base pair with thymine (T), as does guanine (G) with cytosine (C) in DNA. In RNA, thymine is replaced by uracil (U). As such, A is complementary to T and G is complementary to C. In RNA, A is complementary to U and vice versa. Typically, "complementary" refers to a nucleotide sequence that is fully complementary to a target of interest such that every nucleotide in the sequence is complementary to every nucleotide in the target nucleic acid in the corresponding positions. In certain cases, a nucleotide sequence may be partially complementary to a target, in which not all nucleotide is complementary to every nucleotide in the target nucleic acid in all the corresponding positions.

The term "probe," as used herein, refers to an oligonucleotide that is complementary and hybridizes to a nucleotide sequence of interest, typically to facilitate its detection.

The term "solid support" as used herein refers to any solid material able to bind oligonucleotides, e.g. by hydrophobic, ionic or covalent interaction.

The term "immobilisation" as used herein refers to reversible or irreversible association of the probes to said solid support, such as 3D matrix. If reversible, the probes remain associated with the solid support for a time sufficient for methods of the invention to be carried out.

The term "environmental sample" as used herein refers to any substance comprising bacterial community. As used herein, environmental samples include water and oil samples that comprise bacterial populations of varying genus and species that may be identified by the low density MIC BioChip described here. The environmental samples may comprise a bacterial consortium unique to a geographic region or target reservoir, or, alternatively the bacterial consortium may be adaptable to other environment sites, geographies and reservoirs. The methods of the present invention are suitable for analyzing the presence of MIC microorganism(s) in a sample originating from an oilfield or an oil well or from an oil production process, or any related equipment, surface, or systems, storage tanks or pipes.

High density microarray and low density biochips. DNA biochips are divided into two major classes: high density microarray and low density biochips. Microarrays typically contain thousands and tens of thousands probes. Low density biochips usually contain tens and hundreds probes. The proposed "low-density" MIC BioChip described herein aims to detect the bacterial consortium and to feature the risk assessment using the minimum panel, consisting of from the following embodiments: 13 genes/21 probes, including 5 genes (apr; hynAB; hydA (NiFe); hydA (Fe); hypB)/10 probes required for accurate detection of SRBs; and 10 genes (mcr; hydA (NiFe); fthfs; a/bssA; hydA (Fe); hyaA; nirS; nirK; narG; napA)/11 probes for accurate detection of the next preferred members. (Table 5) Extended panel consists from 14 genes/30 probes (Table 5). In certain embodiments, additional combinations Therefore, the MIC-biochip can be considered a low density biochip.

The term "hairpin structure" as used herein refers to a polynucleotide or nucleic acid that contains a double-stranded stem segment and a single-stranded loop segment wherein the two polynucleotide or nucleic acid strands that form the double-stranded stem segment are linked and separated by the single polynucleotide or nucleic acid strand that forms the loop segment. The "hairpin structure" can further comprise 3' and/or 5' single-stranded region(s) extending from the double-stranded stem segment.

The term "label" as used herein refers to any atom or molecule which provides a detectable (preferably quantifiable) effect and which can be attached to a nucleic acid. The term "label" includes e.g. colored dyes; radioactive labels; binding moieties such as biotin; haptens such as digoxgenin; luminogenic, phosphorescent or fluorogenic moieties; and fluorescent dyes alone or in combination with moieties that can suppress or shift emission spectra by the energy transfer of fluorescence. Labels may provide signals, which are detectable for example by fluorescence, radioactivity, colorimetry, gravimetry, X-ray diffraction or absorption, magnetism and enzymatic activity. A label may be a charged moiety (positive or negative charge) or may also have a neutral charge. They may include or consist of nucleic acid or protein sequence. Preferred labels are dyes and in particular preferred labels are fluorescent dyes. The amplification and the labeling can be performed either simultaneously or in subsequent steps.

Kits

The present invention also provides kits comprising the components of the combinations of the invention in kit form. A kit of the present invention includes one or more components including, but not limited to, one or more probes of the present disclosure, wherein one or more probes are used for detection of corrosion causing bacteria. In one embodiment, the kit of the present invention includes one or more components including, but not limited to, one or more probes of the present disclosure, wherein one or more probes are used for detection of target nucleic acid in a sample. In one embodiment, the kit includes a matrix comprising nucleic acid probes for detecting a labeled target nucleic acid in a sample. The nucleic acid probes are embedded in the matrix and comprise nucleotide sequences that are substantially complementary to one or more labeled nucleotide sequences in the target nucleic acid.

As a matter of convenience, one or more probes disclosed herein can be provided in a kit, i.e., a packaged combination of reagents in predetermined amounts with instructions for performing the diagnostic or detection assay. Additives may be included into the kits, such as reagents used for DNA purification, DNA amplification, DNA fragmentation, DNA labeling, and/or DNA hybridization. In some embodiments, the kits of the present invention include sample buffer, reaction buffer, enzyme mix, Fragmentase reaction buffer, nucleotide mix, 1M GuSCN, 5 mM EDTA, or 50 mM HEPES (pH 7.5). The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

The kit's components may be pre-attached to a solid support, or may be applied to the surface of a solid support when the kit is used. In some embodiments, the signal generating means may come pre-associated with a probe of the invention or may require combination with one or more components. Optionally the kit may also comprise instructions for carrying out the methods of the invention.

The detection kits disclosed herein may also be prepared that comprise at least one of the probes disclosed herein and instructions for using the composition as a detection reagent. Containers for use in such kits may typically comprise at least one vial, test tube, flask, bottle, syringe or other suitable container, into which one or more of the detection and/or therapeutic composition(s) may be placed, and preferably suitably aliquoted. Where a second detection agent is also provided, the kit may also contain a second distinct container into which this second detection composition may be placed. Alternatively, a plurality of compounds may be prepared in a single composition, and may be packaged in a single container means, such as a vial, flask, syringe, bottle, or other suitable single container. The kits of the present invention will also typically include a means for containing the vial(s) in close confinement for commercial sale, such as, e.g., injection or blow-molded plastic containers into which the desired vial(s) are retained. Where a radiolabel, chromogenic, fluorogenic, or other type of detectable label or detecting means is included within the kit, the labeling agent may be provided either in the same container as the detection or therapeutic composition itself, or may alternatively be placed in a second distinct container means into which this second composition may be placed and suitably aliquoted. Alternatively, the detection reagent and the label may be prepared in a single container means, and in most cases, the kit will also typically include a means for containing the vial(s) in close confinement for commercial sale and/or convenient packaging and delivery.

General Methods

In accordance with the present invention, there may be numerous tools and techniques within the skill of the art, such as those commonly used in molecular immunology, cellular immunology, pharmacology, and microbiology. See, e.g., Sambrook et al. (2001) Molecular Cloning: A Laboratory Manual. 3rd ed. Cold Spring Harbor Laboratory Press: Cold Spring Harbor. N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J. Production, purification, and fragmentation of polyclonal and monoclonal antibodies are described (Coligan, et al. (2001) Current Protocols in Immunology, Vol. 1, John Wiley and Sons, Inc., New York; Harlow and Lane (1999) Using Antibodies, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) Current Protocols in Immunology, Vol. 4, John Wiley, Inc., New York).

Abbreviations

CGA: community genome arrays
DBB *Desulfobulbus*
DBM *Desulfobacterium*
DSB *Desulfobacter*
DCC-DNM-DSS *Desulfococcus-Desulfonema-Desulfosarcina*
DFM *Desulfotomaculum*
DSV-DMB *Desulfovibrio-Desulfomicrobium*
FB: fermentative bacteria
FGA: functional gene arrays
MIC: microbially influenced corrosion
MRB: metal-reducing bacteria
NRB: nitrate-reducing bacteria
SRB: sulfate-reducing bacteria Recent advances in microarray technology have allowed the development of nucleic acid microarrays that are customizable for a specific assay. This methodology provides for the attachment of a desired number of specific nucleic acid sequences to a miniaturized immobilized support creating a nucleic acid microarray. Subsequently, these microarrays then may be used to screen the genetic sequences of a given field sample. Selected sequences to be analyzed may be submitted to a company that has the technology to manufacture such nucleic acid microarray chips. Such companies include, but are not limited to Affymetrix, inc. or Eppendorf International. Affymetrix Inc. has developed a high density GENECHIP® Microarray and Eppendorf has created a low density SILVERQUANT® Microarray that allows for the high throughput quantification of specific mRNA. In this sense, density refers to the number of features (genetic sequences at each location), where high density refers to a greater number of features relative to low density. While higher density systems may monitor more genes in comparison to the relatively lower density systems, they may be significantly more expensive. The building of such microarrays is known, and is exemplified in U.S. Pat. Nos. 7,115,364, 7,205,104, and 7,202,026. The process generally involves photolithographic binding or spotting of target nucleotide sequences to a customized DNA microarray. Such a DNA microarray could be used to correlate fluorescent values corresponding to hybridized mRNA or DNA with quantification using target sequences from specifically identified strains to probe field samples. It is noted that in certain embodiments, a field sample mRNA may directly hybridize with target sequence or it may be converted into cDNA (complementary DNA which is more stable) to be hybridized with a target sequence.

In certain embodiments, the extended panel for a low-density MIC BioChip (30 probes) comprises a biochip based on the targeted functional gene detection and structural gene detection (16S rRNA) of 30 total probes, as shown in Table 5. In certain embodiments, an extended variant of the BioChip contains 14 genes: 13 functional genes (apr; hynAB; hydA (NiFe); hydA (Fe); hypB; hyaA; mcr; fthfs; a/bssA; nirS; nirK; narG; napA) and 1 structural gene (16SrRNA) (30 probes) (shown in Table 5). In certain embodiments, the 16SrRNA gene and 9 probes for the different bacteria are included as additional verifying features.

In additional embodiments, the low-density MIC BioChip will be in the form of an FGA.

Many groups of bacteria commonly present in oil beds directly or indirectly contribute to the process of biogenic corrosion. Sulfate-reducing bacteria (SRB) is one of the groups of bacteria most often identified as being involved in and contributing to corrosion. The SRB can be divided into six main groups based on 16S rRNA gene sequences:

*Desulfotomaculum* (DFM), Group 1;
*Desulfobulbus* (DBB), Group 2;
*Desulfobacterium* (DBM), Group 3;

*Desulfobacter* (DSB), Group 4;
*Desulfococcus-Desulfonema-Desulfosarcina* (DCC-DNM-DSS), Group 5;
*Desulfovibrio-Desulfomicrobium* (DSV-DMB), Group 6.
SRB-induced corrosion is schematically described by the following reactions:

$$8H_2O \rightarrow 8H^+ + 8OH^- \text{ (water ionization)}$$

$$4Fe \rightarrow 4Fe^{2+} + 8e^- \text{ (anodic site, iron ionization)}$$

$8H^+ + 8e^- \rightarrow 8H$ (the formation of a protective film at the cathode, preventing the further dissolution of the metal).
Cathodic depolarization takes place in the presence of SRB:

$$SO_4^{2-} + 8H \rightarrow S^{2-} + 4H_2O$$

In addition, the secondary reactions proceed:

$$Fe^{2+} + S^{2-} \rightarrow FeS$$

$$3Fe^{2+} + 6OH^- \rightarrow 3Fe(OH)_2$$

The summary corrosion reaction is the following:

$$4Fe^{2+} + SO_4^{2-} + 4H_2O \rightarrow FeS + 3Fe(OH)_2 + 2OH^-$$

Depolarizing activity of SRB increases significantly due to the formation of hydrogen sulfide at cathodic site in the reaction:

$$2H^+ + S^{2-} \rightarrow H_2S$$

Frequent depolarization (consuming polarized hydrogen) leads to stimulation of the cathode area. In addition, the formation of the new cathodes, which are the end products of sulfate reduction to insoluble sulfides of iron and other metals, stimulates the cathode area. In view of these reactions, the following processes accelerate microbial corrosion:
1. The metal ions bind to the sulfide ions and weaken overpotential (overvoltage) at the near-electrode layer, accelerating the anodic reactions and forming the new cathodes;
2. SRB and *Archaea* decrease hydrogen overpotential (overvoltage) at the near-electrode layer, thereby accelerating the cathodic reactions.

The detection of SRB is an important step in MIC monitoring. As an aspect of the present invention, detection of functional genes, dissimilatory sulfite reductase (dsr) and adenosine 5'-phosphosulfate reductase (apr) (genes directly associated with the reduction of inorganic sulfate) is proposed as part of a Low Density MIC BioChip. The apr probe can be successfully used for screening of a wide spectra of sulfate-reducing bacteria: *Desulfovibrio indonensis, Desulfovibrio alaskensis, Desulfovibrio vietnamensis, Desulfovibrio vulgaris, Desulfovibrio gigas, Desulfovibrio desulfuricans, Desulfomicrobium baculatus, Desulfococcus multivorans, Desulfobulbus propionicus, Desulfofrigus fragile, Desulfofrigus oceanense, Desulfotalea psychrotphila, Desulfotalea arctica, Desulfofada gelida, Desulfocinum infernum, Desulfotomaculum nigrificans, Desulfosporosinus orientis* [10]. Additionally, two dsr gene probes can be used for the identification of SRB in the environmental samples [11].

As another aspect, it is proposed that detecting SRB be based in part on a division into groups I-IV on the basis of specific hydrogenase genes. The hydrogenase genes along with reductase genes of SRB are the genes encoding enzymes which largely contribute to MIC development, since biocorrosion is accelerated by hydrogenases utilizing cathodic hydrogen.

Bacterial hydrogenases can be placed into three broad categories based on the metal cofactors found at their active sites: (Fe) hydrogenases; (NiFe) hydrogenases, and (NiFeSe) hydrogenases. (Fe) hydrogenases are characterized by low affinity to hydrogen and work preferentially at its high concentration. (NiFeSe) hydrogenases are characterized by high affinity to hydrogen. (NiFe) hydrogenases can compensate for the absence of activity of two other types of hydrogenases. Hydrogenases also differ in their susceptibility to inhibitors. (Fe) hydrogenases are the most sensitive to CO and $NO^{2-}$, as well as (NiFeSe) hydrogenases. (NiFe) hydrogenases are particularly resistant to inhibitors such as CO and $NO^{2-}$, which are the main products of metabolism of bacterial community in the anaerobic conditions. (NiFe) hydrogenases are divided into 4 groups: 1) periplasmic proteins; 2) soluble cytoplasmic proteins; 3) bilateral membrane-bound proteins; and 4) membrane-bound outer cytoplasmic proteins.

An aspect of the present invention relates to evaluating SRB effects on corrosion by dividing the SRB into four groups and detecting one or more of the following hydrogenase genes (as shown in FIG. 12A):
Group I *Desulfovibrio* and *Desulfobacterium* (Periplasmic (NiFe) hydrogenase);
Group II *Desulfobulbus, Desulfobacter* and *Desulfomicrobium* (Membrane-bound (NiFe) hydrogenase)
Group III *Desulfotomaculum* ((Fe) hydrogenase)
Group IV *Desulfococcus* (Hydrogenase accessory protein HypB; hypB gene).

Group I consists of *Desulfovibrio* and *Desulfobacterium*. Mostly, the corrosion of underground steel structures is caused by the genus *Desulfovibrio*. Overview of the hydrogenase genes in SRB reveals that all studied *Desulfovibrio* spp. possesses the genes of periplasmic (NiFe) hydrogenase (hynAB-genes), containing the highly homologous domain. The occurrence of (Fe) and (NiFeSe) hydrogenase in *Desulfovibrio* spp is limited [14]. Furthermore, (NiFe) hydrogenases are particularly resistant to inhibitors such as CO and $NO^{2-}$, which are the main products of metabolism of bacterial community in the anaerobic conditions. The use of periplasmic (NiFe) hydrogenase gene (hynAB) strongly suggests the detection of *Desulfovibrio* spp. in SRB consortium. *Desulfobacterium* spp. possesses hynB periplasmic (NiFe) hydrogenase gene as well. The specific probe is designed on the basis of hynB gene of *Desulfobacterium* sp. In addition, two probes for the identification of SRB on the basis of the structural 16S rRNA genes are selected from the literature [Loy A., et al., *Oligonucleotide microarray for 16S rRNA gene-based detection of all recognized lineages of sulfate-reducing prokaryotes. Appl Environ Microbiol* (2002) 68:5064-5081]. These probes allow confirming the presence of *Desulfovibrio* spp. and *Desulfobacterium* spp. by the specific structural gene probes.

Group II consists of *Desulfobulbus, Desulfobacter* and *Desulfomicrobium*. They are characterized by the sequentially distinguished (NiFe) membrane-bound hydrogenase (hydA).

Group III comprises of *Desulfotomaculum* spp. These bacteria are gram-positive bacteria unlike other groups; this is reason why sulfate reduction occurs without periplasmic hydrogen oxidation. All hydrogenases are Fe-containing, excluding *Desulfotomaculum ruminis*, possessing (NiFe) hydrogenase. Corrosion is caused by bacterial genus *Desulfotomaculum* at high temperatures.

Group IV consists of *Desulfococcus*. This group can be discriminated by hydrogenase accessory protein HypB gene (hypB). *Desulfococcus* group is the less dangerous group of bacteria involved in steel corrosion as this group predominantly uses organic substrates as electron donors thereby not accelerating the cathodic depolarization.

In view of these correlations, detecting at least the above mentioned panel of 6 functional genes and 1 structural gene (16S rRNA) in a functional array (FGA) using the low-density MIC BioChip enables identification of the main SRB groups involved in biocorrosion (dsr, apr, hynAB (NiFe), hydA (NiFe), hydA(Fe), hypB, 16S rRNA). 12 probes were selected for identification of main SRB groups, 10 for functional genes and 2 for structural genes (Table 1, probes 1-12, e.g., SEQ ID NO:1-12). 7 probes for functional genes were designed de novo.

The selection of these microorganisms, whose metabolic products contribute to the SRB life cycle, is very beneficial for the risk assessment and monitoring of biocorrosion.

TABLE 1

38 initial oligonucleotide probes selected on the basis of the key genes of metabolic pathways involved in MIC.

| Probe | Group | Targeted | Targeted geme | Probe name | Sequence 5'-3' | References |
|---|---|---|---|---|---|---|
| 1 | SRB (Sulfate-Reducing Bacteria) | SRB | APR-reductase | SRB1 | CCA GGG CCT GTC CGC CAT CAATAC (SEQ ID NO: 1) | Zinkevich V., et al., FEMS Microbiol Ecol (2000) 34:147-155 |
| 2 | | SRB | DSR-reductase | DRS1 | GTG TAG CAG TTA CCG CA (SEQ ID NO: 2) | Klein M., et al., Journal of Bacteriology, (2001)183: 6028- |
| 3 | | SRB | DSR-reductase | DRS2 | ACC CAC TGG AAG CAC G (SEQ ID NO: 3) | Klein M., et al., Journal of Bacteriology, (2001)183: 6028-6035 |
| 4 | | *Desulfobvibrio* | hynB (periplasmic Ni,Fe hydrogenase) | Dv | CAC CCC TGC ATC GGC TGC AG (SEQ ID NO: 4) | de novo |
| 5 | | *Desulfobacterium* | hynB (periplasmic Ni, Fe hydrogenase) | Dbacterium1 | CAC TGG AAC AG CGA TCA AG (SEQ ID NO: 5) | de novo |
| 6 | | *Desulfobulbus* | hydA (Ni, Fe-hydrogenase) | Dbulbus | GCG CCA CCC TGC CGT TCA AC (SEQ ID NO: 6) | de novo |
| 7 | | *Desolfobacter* | hydA (Ni, Fe-hydrogenase) | Dbacter2 | TCA CCT GGT GAA AAT CGG ACT (SEQ ID NO: 7) | de novo |
| 8 | | *Desulfomicrobium* | hydA (Ni, Fe-hydrogenase) | Dsmicrobium1 | CCA CAA CCT GGC CAT CCC GGA AAT (SEQ ID NO: 8) | de novo |
| 9 | | *Desulfotomaculum* | hydA (Fe-hydrogenase) | Dtomaculum2 | CAC GCA TCG GGG AGA GGG TGG (SEQ ID NO: 9) | de novo |
| 10 | | *Desulfococcus* | hydB gene of hydrogenase accessory protein HypB | Dscoccus | CAC CTC CTC CAA AAC CGG GGA AGG (SEQ ID NO: 10) | de novo |
| 11 | | *Desulfobibrio* | 16S rRNA gene for *Desulfovibrio* spp. (including *Dv. vulgaris*, *Dv. desuluricans*) | Dv 16S_1 | CAA TCC GGA CTG GGA CGG (SEQ ID NO: 11) | Loy A., et al., Appl Environ Microbial (2002)68:5064-5081 |
| 12 | | *Desulfobacterium* | 16S rRNA gene for *Desulfobacterium* spp | Dbacterium 16S_2 | GCG CGT TGT ACA TAC CAT (SEQ ID NO: 12) | Loy A., et al., Appl Environ Microbial (2002)68:5064-5081 |
| 13 | *Archaea* | Methanogenic Archaea | Methyl coenzyme M reductase (mcr) | MCR1 | CCA GGT GC ATC AAG TTC GGA CAC (SEQ ID NO: 13) | de novo |
| 14 | | *Archaea* | 16S rRNA gene | Archaea1 | GTG CTC CCC CGC CAA TTC AT (SEQ ID NO: 14) | Loy A., et al., Appl Environ Microbial (2002)68:5064-5081 |

TABLE 1-continued 38 initial oligonucleotide probes selected on the basis of the key genes of metabolic pathways involved in MIC.

| Probe | Group | Targeted | Targeted gene | Probe name | Sequence 5'-3' | References |
|---|---|---|---|---|---|---|
| 15 | | Archaea | 16S rRNA gene | Archaea2 | TGT TGA CTA CGT GTT ACT GAG (SEQ ID NO: 15) | Loy A., et al., Appl Environ Microbial (2002)68:5064-5081 |
| 16 | | Archaea | 16S rRNA gene | ARC16SRNA | AGG AAT TGG CGG GGG AGC AC (SEQ ID NO: 16) | Raskin L., et al. Applied and Environmental Microbiology (1994) |
| 17 | MRB (Metal-Reducing Bacteria) | Geobacter spp | hydA (Ni, Fe-hydrogenase) | Geobac | CAC CCG GTGCAC TCC TGG A (SEQ ID NO: 17) | de novo |
| 18 | | Shewanella spp | hydA (Ni, Fe-hydrogenase) | Shew | ACA ACT GCC CAA CCG AGC GC (SEQ ID NO: 18) | de novo |
| 19 | | Geobacter spp | 16S rRNA gene | Geobacter | CTCACG CAC TTC GGG ACC G (SEQ ID NO: 19) | de novo |
| 20 | | G. sulfurreducens | 16S rRNA gene | GeoS | TTC GGG CCT CCT GTC TTT C (SEQ ID NO: 20) | de novo |
| 21 | | G. metallireducens | 16S rRNA gene | GeoM | TTC GGG CCT TTT GTC ACC (SEQ ID NO: 21) | de novo |
| 22 | | Shewanella spp | 16S rRNA gene | ShewRNA1 | CGC GAT TGG ATG AAC CTA G (SEEQ ID NO: 22) | de novo |
| 23 | | Shewanella spp | 16S rRNA gene | ShewRNA2 | AGC TAA TCC CAC CT GGT CA (SEQ ID NO: 23) | de novo |
| 24 | | Arthrobacter spp | 16S rRNA gene | 16SRNA PR | GTC TGC CGT GAA AGT CCG (SEQ ID NO: 24) | de novo |
| 25 | FB (Fermentative bacteria) | Acetogenic | formyltetrahydrofolate synthetase (fthfs) | FTHFS | TGC ATG GCC AAG ACC CAA TAC AGC (SEQ ID NO: 25) | Salmassi TM., et al. Microbiology (2003) 149:2529-2537 |
| 26 | | Hydrocarbon-degrading | alkylsuccinate synthase and benzylsuccinate synthase alpha subunits (assA/bssA) | a/bssA | TCG TCA TTG CCC CAT TTG GGG GC (SEQ ID NO: 26) | Callaghan AV., et al. Environ Sci and Technol (2010)44: 7287-7294 |
| 27 | NRB (Nitrate Reducing Bacteria) | Firmicutes | hydA (Fe-hydrogenase) | FirmicutishydA | AGG CGG CGA GCA TGA TCC AGC AAT (SEQ ID NO: 27) | de novo |
| 28 | | E.coli | hyaA | E.coli | ACT CCT GCG CGC CAA TCC AG (SEQ ID NO: 28) | de novo |
| 29 | | NRB (Nitrate Reducing | nitrite reductase (nirS) | nirS | CGC TGT TCG TCA AGA CCC ATC CG (SEQ ID NO: 29) | de novo |
| 30 | | NRB (Nitrate Reducing | nitrite reductase (nirK) | nirK | CCC GAC CCA CGT CGT ATT CAA CGG (SEQ ID NO: 30) | de novo |
| 31 | | NRB (Nitrate Reducing | nitrite reductase (narG) | napG | CCA GCT TCT TCT ACG CCC ACA CCG (SEQ ID NO: 31) | de novo |
| 32 | | NRB (Nitrate Reducing | nitrite reductase (napA) | napA | CCG CGG CTA TGT GGG TCG AAA AAG (SEQ ID NO: 32) | de novo |

TABLE 1-continued 38 initial oligonucleotide probes selected on the basis of the key genes of metabolic pathways involved in MIC.

| Probe | Group | Targeted | Targeted geme | Probe name | Sequence 5'-3' | References |
|---|---|---|---|---|---|---|
| 33 | Bacterial Controls | Bacteria | 16S rRNA gene | Bacterial | GAC ATA AAG GCC ATG AGG CTG (SEQ ID NO: 33) | Loy A., et al., Appl Environ Microbial (2002)68:5064-5081 |
| 34 | | Bacteria | 16S rRNA gene | Bacteria2 | CAG TGA GGA ATT TTG CGC AC (SEQ ID NO: 34) | Loy A., et al., Appl Environ Microbial (2002)68:5064-5081 |
| 35 | | Bacteria | 16S rRNA gene | Universal | GAC GGG CGG TGT GTA CA (SEQ ID NO: 35) | amann RI., et al. Microbiol Rev (1995)59:143-169 |
| 36 | | Bacteria | 16S rRNA gene | 16SCONS_1 | CCT ACG GGA GGC AGC AG (SEQ ID NO: 36) | Muyzer G., et al., Appl and Environ Micobiol. (1993) 59:695-700 |
| 37 | | Bacteria | 16S rRNA gene | 16SCONS_2 | ATT ACC GCG GCT GCT GG (SEQ ID NO: 37) | Muyzer G., et al., Appl and Environ Micobiol. (1993) 59:695-700 |
| 38 | | Bacteria | 16S rRNA gene | 16SCONS_3 | CGG CAG GCC TAA CAC ATG CAA GTC G (SEQ ID NO: 38) | Avaniss-Aghajani E., et al., BioTechniques (1994)17:144-149 |

In addition to detecting the genes identified above relating to the SRB community, aspects of the present invention also may include detecting one or more additional genes from the following groups which contribute to accelerating biocorrosion processes:

1. A complex set of reactions participates in the production of MIC on metal surface. These reactions are strongly influenced by methanogenic respiration. The most methanogens utilize hydrogen and acetate by forming methane. Since corrosion is accelerated in the anaerobic zone by utilizing cathodic hydrogen, *methanogenic archaea* plays an important role in biocorrosion. The functional gene, encoding the alpha subunit of the methyl-coenzyme M reductase (MCR) (FIG. 12B), catalyzes the last step in methanogenesis and is present in all methanogens, including *methanogenic archaea*. Methanogens represent a unique but phylogenetically diverse group of prokaryotes, which can be conveniently tracked in the environment by targeting the mcrA gene as a functional marker. The conservative sequence of the structural 16S rRNA gene of *Archaea* was selected from a public database [16] and was used for the detection of *Archaea* in the MIC consortium. The block of 4 probes (1 for functional gene mcrA and 3 for structural genes 16S rRNA genes) was used for detection of *methanogenic archaea* in the biocorrosion consortium (probes 13-16, Table 1).

Figure 12C:
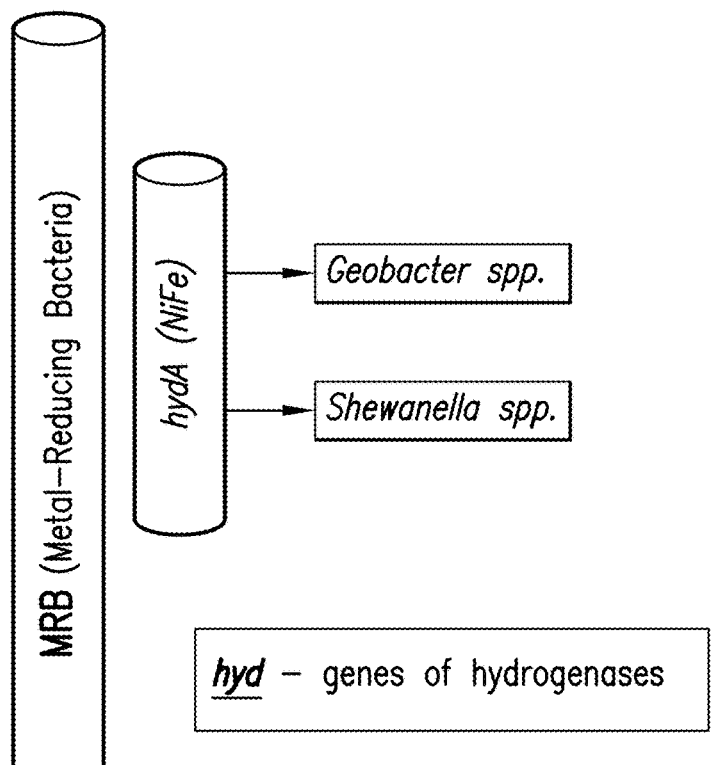

2. Metal-reducing bacteria (MRB) as shown in FIG. 12C, metabolize iron as well as other metals and create conditions for insoluble metal sulfide formation and as consequence produce alternative cathode areas; MRB also decreases oxygen during its growth, which in turn supports SRB. *Geobacter* spp. are all capable of acetate oxidation by reducing Fe (III). Moreover, the different species of *Geobacter* are capable of making electrical contacts with other organisms as electron acceptors outside the cell. The *Geobacter* spp. occurs in a variety of anaerobic environments, where reduction of Fe (III), as the terminal electron acceptor, is very important. The most intensively studied species of *Geobacter* are *G. metallireducens* and *G. sulfurreducens*. Bacteria of the genus *Shewanella* are facultative anaerobes, and can reduce metal oxides, nitrates and sulfates in the anaerobic environments. The genus is capable for long-term environmental adaptation. The identification of *Geobacter* and *Shewanella* genus can be carried out on the basis of hydrogenases hydA (Ni,Fe-hydrogenase) genes. In addition, 6 probes were designed on the basis of the structural 16S rRNA gene for the identification of *Geobacter*, *Shewanella* and *Arthrobacter* spp., and for distinguishing *G. metallireducens* from *G. sulfurreducens*. The block of 8 probes (2 for functional genes (hydA (Ni,Fe-hydrogenase)) and 6 for structural genes (16S rRNA)) were designed for the discrimination of Metal-reducing bacteria in the biocorrosion consortium (as shown in Table 1).

3. Fermentative bacteria (FB), which increase the metabolism of methanogenic bacteria by producing acetate through degradation of hydrocarbons and acidic fermentation in the anaerobic conditions. For the characterization of the FB the following functional genes were used as the source of the probe design: formyltetrahydrofolate synthetase (fthfs) gene, and alkylsuccinate synthase and benzylsuccinate synthase alpha subunits (assA/bssA) genes. Firmicutes are the phylum of bacteria including anaerobic Clostridia spp., and obligate or facultative *Bacillus* spp. with very well developed hydrogenase activity. The block of 3 probes (all 3 for functional genes, fthf, assA/bssA, and hydA) were used for the discrimination of fermentative bacteria involved in the biocorrosion (probes SEQ ID NO:25-27, Table 1).

4. Since biocorrosion is accelerated by hydrogenase utilizing cathodic hydrogen, all microorganisms in the anaerobic conditions with well-developed and active hydrogenase system can be considered as activators of biocorrosion, for example *E. coli*. *E. coli* can be detected using a probe based on the functional hydrogenase hyaA (probe SEQ ID NO:28, Table 1).

5. Presence of the nitrate-reducing bacteria (NRB) is another important characteristics of MIC development, as NRB are microorganisms that compete with SRB in the redox processes. Soil sulfate reduction starts only when the environment becomes exhausted of nitrates. This is likely the consequence of the extremely high oxidation-reduction potential for sulfate reduction in the presence of NO3-ions as well as consequence of the competitive inhibition of sulfate reduction with nitrates, which may serve as an electron acceptor during anaerobic respiration. As the result, an accumulation of ammonium ions and a significant alkalinization takes place in the environment. The presence of NRB in the bacterial consortium can be confirmed through the detection of functional nar and nap genes, coding nitrate-reduction pathway, and functional nir genes, coding nitrite-reduction pathway. Nitrate reductases catalyse the two-electron reduction of nitrate to nitrite. narG genes encode a catalytic α subunit of membrane-bound respiratory nitrate reductase; napA genes encode a catalytic subunit of periplasmic dissimilatory nitrate reductase. Nitrite formed by nitrate reduction can be reduced to ammonium or to nitric oxide by different types of nitrite reductases. nirS genes encode cytochrome $cd_1$ nitrite reductase and nirK genes encode copper nitrite reductase, reducing nitrite to nitric oxide in the periplasm of denitrifying bacteria. Consequently, under certain circumstances, it will be useful to include detection of one or more of the narG, nirS/nirK, and napA, in the low-density MIC BioChip and related methods. The block of 4 probes for functional genes (nirS, nirK, narG, napA) was used to detect denitrifying bacteria (probes SEQ ID NO:29-32, Table 1).

6. Lastly, six probes were chosen for the detection of any bacteria in the consortium. The hybridization signal from these probes may serve as the positive control in the low-density MIC BioChip (probes SEQ ID NO:33-38, Table 1).

An important factor of SRB survival is interspecies interactions with methanogens. In the absence of sulfates, SRB perform the transfer of hydrogen to other microorganisms, acting as acceptors. The genus *Desulfovibrio* and methanogens (functioning satellites of SRB) accomplish the transfer of hydrogen by hydrogenases, localized in the periplasmic space of the membranes.

It will be beneficial under certain conditions, to detect certain sulfate-reducing bacteria and methanogens in a monitoring program for MIC risk assessment. Monitoring programs can be expanded and improved by including the metabolic relationship of a consortium of microorganisms that significantly contribute to corrosion. Under certain conditions, the following microorganisms can be included in the monitoring of MIC risk assessment as sustaining MIC microorganisms:

1. Fermentative bacteria (Firmicutes-Clostridia), which can metabolize organic substrates into organic acids (especially acetate), as acetate, $H_2$ and $CO_2$ are the sources of energy and carbon for SRB and *Archaea*;

2. Metal-reducing bacteria that create the conditions for the formation of insoluble products, particularly metal sulfides as alternative cathode regions.

3. Bacteria with active NiFe hydrogenase system (*E. coli*).

A unique assortment of specific probes for low-density MIC BioChips have been identified as described herein, and in part by focusing on the cathode and anode reactions and ranking functional genes to evaluate and detect a panel of microorganisms most likely to influence MIC. Certain groups of the enzymes coded for by these functional gene probes accelerate the electrochemical processes in biocorrosion. While not wishing to be bound by theory, the microorganisms with active and developed hydrogenase systems are targeted; and in certain embodiments include detecting *Desulfovibrio* spp. Detection by using hydrogenase genes hynAB, hydA, and by hydrogenase accessory protein HypB gene hypB is expected to provide the ratio of sulfate-reducing microorganisms within the MIC consortium.

In certain aspects, the presently described low-density MIC biochip provides data for assessing not only the biocorrosion risk, but also estimates alternative processes such as nitrate reduction. In other aspects, the low-density MIC biochip of the present invention will provide accurate data and more comprehensive coverage of the relevant organisms involved in MIC inducing, sustaining and opposing bacteria providing a corrosion scale for the bacterial community.

In some aspects, the present invention relates to an informative arrangement of 30 oligonucleotide probes, with variations in the subsets of probes to be used for various scenarios as described herein, immobilized on an MIC biochip, such that upon hybridization with oligonucleotides in a test sample, a pattern is produced that can be interpreted with a suitable means.

In one aspect, the MIC BioChip described herein is a collection of miniaturized test sites arranged on a solid substrate that permits numerous tests to be performed simultaneously in order to achieve higher throughput and speed. MIC BioChip of the present invention comprises an arrayed series of microscopic spots of DNA oligonucleotides, each containing picomoles ($10^{-12}$ moles) of a specific DNA sequence, referred to as probes. The probes are synthesized prior to deposition on the array surface and are then immobilized onto a solid support (matrix).

In additional aspects, the MIC BioChip provides DNA oligonucleotide probes for key genes of metabolic pathways involved in MIC. The resulting MIC BioChip pilot comprises 30 highly specific and sensitive probes, wherein 11 probes enable identification of key SRB groups involved in the biocorrosion and allow for grading SRB groups on the corrosion scale, 18 probes are used for the identification of other MIC bacterial groups, one probe serves as positive control.

In another aspect, the present invention provides a method for detecting binding between a probe and a target sample, comprising applying the target sample including a target DNA to be bound to the oligonucleotide probe onto the MIC BioChip and detecting the target DNA specifically bound to the oligonucleotide probe. In one embodiment, fragments of DNA are labeled with a signaling substance, such as a fluorescent dye for easy detection of the target DNA. The binding between an oligonucleotide probe and a target DNA can be detected by a variety of methods, for example, a fluorescent detection method, an electrochemical detection method, a mass detection method, a charge detection method, or an optical detection method, which are currently in wide use and are classified according to the type of the signaling substance labeled to the target substance.

More specifically, the present invention provides a low-density MIC BioChip comprising 30 probes proposed for the identification of main bacterial groups involved in biocorrosion. The MIC BioChip of the invention includes 18 de novo probes based on the functional genes and 4 de novo probes based on structural genes. Structural 16S rRNA genes were used for the probe design, based on conserved regions of 16S rRNA gene which will capture as many bacterial species as possible on a biochip and also serve as positive controls, in certain instances.

In certain embodiments, the present invention provides for simultaneous detection of target nucleic acids in a sample. One of the major challenges in designing DNA probes that can be used simultaneously with other DNA is the variation in the conditions necessary for proper hybridization between the DNA probe and nucleic acid target, requiring each hybridization reaction to be carried out individually. Thus, probes that can be used simultaneously require identical hybridization characteristics. In the present invention, inventors used a novel method to evaluate BioChip probes in one reaction, using DNA cassettes, comprising all of the probes in equimolar proportions for a quick determination of the probes unsuitable for inclusion in the biochip [23]. This allowed for the design of probes with identical hybridization characteristics. Thus, the BioChip of the present disclosure offers the ability to achieve simultaneous detection of many DNA targets without detriment to sensitivity.

The inventors of the present disclosure initially designed and evaluated the activity of 38 probes (SEQ ID NO:1-38) described in Table 1, which were then subjected to experimental analysis for their hybridization capacity and sensitivity for inclusion in the pilot MIC BioChip, after the design of four test pilot BioChips.

Numerous steps are involved in the design and generation of an MIC BioChip as described herein. In general, the development of an MIC BioChip includes a combination of any of the following steps:
 a) Design of the appropriate probes;
 b) Selection of the microarray format (2-D array vs. 3-D array);
 c) Equalization of the hybridization capacity of the probes for their inclusion in the biochip prototype by the cassette approach.

More specifically, designing and developing an MIC BioChip as described herein, includes any of the following: probe design, biochip matrix preparation, activation of the surface for the immobilization of oligonucleotide probes, immobilization of oligonucleotide probes onto the activated matrix, and deactivation of matrix. Additionally, several levels of analyses were completed for generation of oligonucleotide probes to be immobilized onto the matrix. Finally, preparation of target DNA and the hybridization of the target DNA is a multistep process that has also been optimized, as described herein.

General steps involved in target DNA preparation for the hybridization on a biochip are the following:
 a) DNA amplification, fragmentation and labeling; and
 b) Hybridization and visualization.

Matrix Preparation: Sensitivity of 3D Matrix Vs. 2D Matrix

A wide variety of supports may be used with the invention. In one aspect, supports are rigid solids that have a surface, preferably a substantially planar surface so that single molecules to be interrogated are in the same plane. The latter feature permits efficient signal collection. Suitable solid support materials include materials such as glass, polyacrylamide-coated glass, ceramics, silica, silicon, quartz, various plastics, and the like. In one aspect, the area of a planar surface may be in the range of from 0.5 to 4 $cm^2$. In one aspect, the solid support is glass or quartz, such as a microscope slide, having a surface that is uniformly silanized. This may be accomplished using conventional protocols, e.g. acid treatment followed by immersion in a solution of 3-glycidoxypropyl trimethoxysilane, N,N-diisopropylethylamine, and anhydrous xylene (8:1:24 v/v) at 80° C., which forms an epoxysilanized surface.

Solid support (matrix) used for the microarray/biochips can be generally divided into two main formats: two-(2D) and three-dimensional (3D). Typical 2D support constitutes glass slides (silanized and subsequently activated or modified by aldehyde, epoxy, activated carboxyl groups etc.) modified to couple with the DNA probes. DNA density on these coated substrates cannot exceed a monolayer that limits the absolute fluorescent signal intensity during biochip visualization. A 3D format considerably increases the available surface area and allows the deposition of higher probe quantities, promoting a higher sensitivity of the biochip analysis. Example of 3D format support is polyacrylamide gel-pads affixed on glass slides and activated to couple with DNA probes [17].

Another example of 3D structures is dendrimer support, which can be formed by the glass slide treatment in a special manner. Dendrimers are repetitively branched polymeric molecules chemically synthesized with well-defined shapes, size and nanoscale physicochemical properties [18]. In contrast to traditional polymers, dendrimers are unique core-shell structures possessing three basic architectural components: a core, an interior of shells (generations), and an outer shell or periphery consisting of branch cell units and terminal functional groups [19, 20]. Identical monomer units bind repeatedly around a core, sequentially building tree architecture of the polymer. Each of these layers between the core and the periphery is called generation. The generation rises after every additional interaction by a sequence of repetitive reactions. The surface of the dendrimer contains reactive terminal groups to perform a variety of functions.

Thus, according to the methods of the present invention, both 2D and 3D solid support matrices can be used to generate a BioChip of the present invention.

The inventors of the present disclosure tested two types of 3D matrices and one type of commercially available 2D matrix (Vantage aldehyde slides, Arrayit, USA) for their coupling and hybridization sensitivity (Example 1). As shown in Example 1, dendrimeric matrix was found to be the most sensitive platform. The main advantages of the dendrimeric matrix include: 1) higher sensitivity compared to that of gel matrix (approximately 2 times); and 2) following the stripping of the surface from the hybridized targets, the surface can be re-used.

Hybridization Capacity of the Probes

A nucleic acid hybridization is a highly specific and sensitive procedure. When designing a probe, it is critical to ensure that the design meets the following well established requirements: (i) probe is specific to the target agent, (ii) predicted melting temperatures (Tm) of the probes are homogeneous, (iii) the length of oligonucleotides, preferably between 18 and 25 bases, is homogeneous, and (iv) the predicted temperature of hairpin formation is above or below temperature of hybridization.

Hybridization kinetics of nucleic acids is temperature dependent, and the specificity and efficiency depend on the hybridization temperature. One of the main difficulties with designing oligonucleotide microarrays is to achieve nearly identical melting temperatures for all probes on the array. There are several approaches for equalizing the probes' hybridization ability. The oligonucleotide probes should be designed with the same predicted melting temperature (±2° C.) by using the algorithm based on the nearest neighbor model [21].

Options and challenges associated with hybridization efficiency have been described and addressed in the field (See, for example: Yilmaz, L. S. and Noguera, D. R. (2004) "Mechanistic Approach to the Problem of Hybridization Efficiency in Fluorescent in situ Hybridization", *Applied and Environmental Microbiology*, 70: 7126-7139. Yilmaz, L. S., Okten, H. E., and Noguera, D. R. (2006) "All Regions of the 16S rRNA of *Escherichia coli* are Accessible in situ to DNA Oligonucleotides with Sufficient Thermodynamic Affinity", *Applied and Environmental Microbiology*, 72: 733-744. Yilmaz, L. S. and Noguera, D. R. (2007) "Development of Thermodynamic Models for Simulating Probe Dissociation Profiles in Fluorescence in situ Hybridization", *Biotechnology and Bioengineering*, 96 (2): 349-363. Yilmaz, L. S., Bergsven, L., and Noguera, D. R. (2008) "Systematic Evaluation of Single Mismatch Stability Predictors for Fluorescence in situ Hybridization", *Environmental Microbiology*, 10(10):2872-2085.) However, there remains much room for improvement of hybridization efficiency in the context of multiple probes on a biochip, as described herein below.

A critical step in biochip design is the selection of probes with identical hybridization characteristics. The theoretical profiles of probes, however, are often inconsistent with experimental data, and this can generate BioChips with irregular signal responses. In the present invention, a novel method was used to evaluate BioChip probes in one reaction, using DNA cassettes, comprising all of the probes in equimolar proportions for a quick determination of the probes unsuitable for inclusion in the biochip [23].

The evaluation of the hybridization potential of each of the 38 probes was accomplished using 16 ss (single strand) cassettes. ss cassettes present a lineal set of sequences complimentary to the studied set of probes (Example 2). The Cy3 fluorescent dye was inserted at 5'-end of ss cassette during the synthesis. The number of probes included in each cassette ranged from 3 to 8, and the size varied from 65 to 142 bases. Table 2 lists composition of ss cassettes. The variations in the fluorescent intensities on a biochip, coming from probe's size and nucleotide sequence differences were determined by the cassette method. Using this approach, the inventors identified 35 probes with similar fluorescent intensities (or binding capacity) and chose them from the initial 38 probes (Table 1) for the identification of main bacterial groups involved in the biocorrosion (Example 2, Table 3).

Optimization of Conditions for Biochip Analysis

The application of microarrays to assessment of microbes in the environmental samples poses a number of technical challenges. One of the main challenges is the specific detection of target nucleic acids against a complex background of non-target sequences. The difficulty of the microarray approach is that all probes are hybridized simultaneously, but specific hybridization conditions often vary between probes. The extended ssDNA approach based on the hybridization of the short (100-200 bases) single stranded ssDNA (PCR fragments) with the appropriate oligonucleotide probe on the biochip was developed and used to evaluate hybridization efficiency (Example 3). This method allows for the preparation of samples in a manner that provides optimal hybridization signal intensity.

Sensitivity is another critical parameter for biochip application. The sensitivity of biochip depends on many factors, such as the quantity of the probes, on the biochip matrix (3-D array format vs. 2-D array format), and the quantity of the labeled target DNA. The pilot MIC BioChip exhibits improved sensitivity in part based on embodiments that are in the 3-D array format. Test results evaluated coupling and hybridization sensitivity of 3 matrixes: 3D gel- and dendrimeric matrixes and one type of commercially available 2D matrix (aldehyde slides, Arrayit, USA). It was shown, that the coupling capacity of the 3D-dendrimeric matrixes is 6 times higher than 3D gel-matrixes. Coupling capacities of 3D gel-matrixes and 2D matrixes are comparable. With respect to the hybridization with the single stranded compliment, the aldehyde slides show the lowest hybridization sensitivity; the hybridization characteristics of both 3D matrixes are comparable and are 3-4 times higher than 2D matrixes.

Target DNA amplification prior to hybridization results in stronger signals and allows detecting specific targets even if they are present in low abundance. The steps of random fragmentation of DNA and its fluorescent labeling precede the hybridization of DNA fragments with the immobilized probes onto the matrix for the biochip visualization. The inventors have developed ten protocols with different combinations of DNA amplification, fragmentation and labeling procedures and tested them by using pure bacterial cultures (*Desulfovibrio indonensis* and *E. coli* BP) and the environmental samples (Example 4). The most effective procedure was then used for analysis of environmental samples on different biochip prototypes.

In One Embodiment, the Target DNA Preparation Comprises the Following Steps:
1. $1^{st}$ target DNA amplification
2. Fragmentation of amplified target DNA
3. $2^{nd}$ amplification and labeling simultaneously.

Thus, in one embodiment, amplified target DNA is fragmented according to any standard method known to a skilled person into smaller fragments. In the following step, the fragmented fragments are subjected to second amplification step and labeling simultaneously (Example 4). Subsequently, the fragments of labeled target DNA are subjected to a hybridizing reaction in order to obtain hybridization between the target DNA and the oligonucleotide probes present in the low density MIC BioChip. These hybridizations can be carried out according to the general knowledge in the art by a skilled person. A number of different methods of DNA preparation for the hybridization on a biochip were tested and compared and they include: 1) $1^{st}$ amplification and labelling simultaneously and then fragmentation, 2) $1^{st}$ amplification, fragmentation, and then labelling without $2^{nd}$ amplification etc. However, not one of the other nine combinations of steps showed the highly detectable fluorescent signals and clear background as the method described above ($1^{st}$ amplification, fragmentation, $2^{nd}$ amplification and labelling simultaneously).

Figure 5:
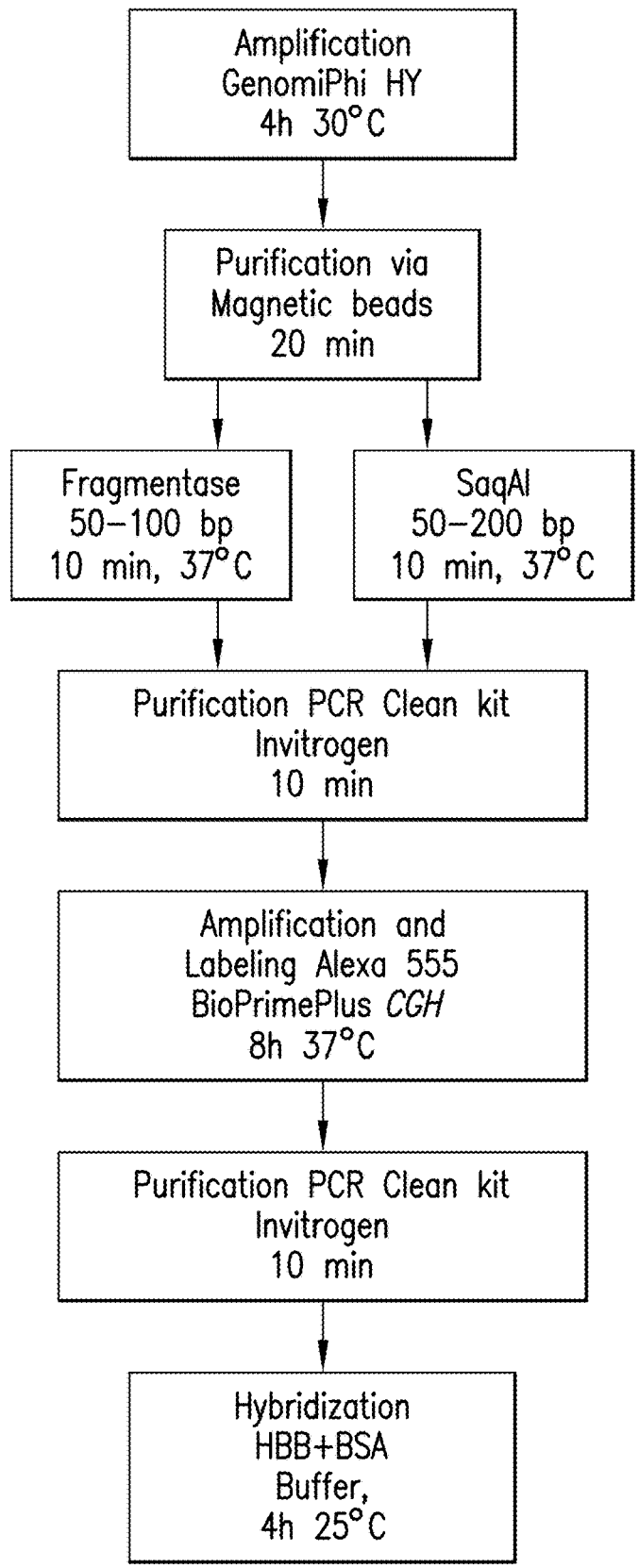
FIG. 5 is a chart outlining the steps of the protocol for target DNA preparation and hybridization.

By designing and testing protocols with different combinations of DNA amplification, fragmentation, and labeling procedures, the inventors have developed an efficient method for amplification of target DNA, referred to as N10 protocol (Example 4, FIG. 5).

Finally, the inventors tested a biochip prototype using *Desulfobacterium autotropicum* DNA (Example 5) and showed that they can obtain successful specificity (FIG. 6).

Example 1

Generation of 3D Matrices

The inventors of the present disclosure generated two different types of 3D matrices: Gel- and two generations Dendrimeric matrices. Two types of 3D matrices and one type of commercially available 2D matrix (Vantage aldehyde slides, Arrayit, USA) were tested for their coupling and hybridization sensitivity. 5'-end of the probe was chemically modified during the synthesis by C6-Amine-group for the 2D aldehyde matrix and 3D dendrimeric matrices. 3'-end was chemically modified by Cy-3 fluorophore for the coupling signal detection. 3'-end is chemically modified during the synthesis by N3-Methyl Uridine, and 5'-end is chemically modified by Cy-3 fluorophore for the coupling signal detection on 3D Gel matrices.

The following protocol was used for dendrimeric platforms preparation:

1. Silanisation of Microscopic Slides for Glass Surface Activation (Amination)

The microscopic glass slides were immersed in 10% NaOH for overnight and subsequently washed with $H_2O$, 1% HCl, again with $H_2O$ and finally with methanol (or ethanol). After 15 min immersion in a 3% 3-aminopropyltrimethoxysilane (APTMS) solution made in 95% methanol (or ethanol) the slide was washed in pure methanol (or ethanol), then in water, dried under a stream of nitrogen (or centrifuged) and baked at 110° C. for 15 min.

2. Dendrimeric Matrix Formation (Synthesis of Linker-System)

Synthesis was performed by repeating the following reaction steps 1 and 2 twice with the respective amines until the desired linker molecules were obtained.

Step 1. Acylation reaction. The aminated glass slides were incubated for 2 hrs in a solution made of 1 mmol acryloylchloride and 1 mmol N,N-diisopropylethylamine (DIEA) in 30 ml anhydrous 1,2-dichloroethane. Subsequently, the supports were thoroughly washed with dichloroethane and dried.

Step 2. Reaction with amine. The acylated glass slides were incubated for 36 hrs with 1 mmol tetraethylenepentamine (TEPA) in 30 ml anhydrous amine free N,N-dimethylformamide (DMF). Afterwards, the slides were extensively washed with DMF, ethanol and acetone before being dried.

Step 3. Acylation reaction. (Step 1). The aminated glass slides were incubated for 2 hrs in a solution made of 1 mmol acryloylchloride and 1 mmol N,N-diisopropylethyl-amine (DIEA) in 30 ml anhydrous 1,2-dichloroethane. Subsequently, the supports were thoroughly washed with dichloroethane and dried.

Step 4. Reaction with amine. The acylated material was incubated for 36 hrs with 1 mmol 1,4-bis-(3-aminopropoxy)butane (BAPB) in 30 ml anhydrous amine free dimethylformamide (DMF). The slides were then extensively washed with DMF, ethanol and acetone before being dried.

3. Activation of the Surface for the Immobilization of Oligonucleotide Probes

Activation was performed by N,N'-disuccinimidylcarbonate (DSC). Specifically, activation was conducted by incubation with 1 mmol DSC and 1 mmol N,N-diisopropylethyl-amine (DIEA) in 20 ml anhydrous acetonitrile for 4 hrs. Subsequently, slides were washed with DMF and 1, 2-dichloroethane and dried under a stream of nitrogen (or centrifuged).

4. Immobilization of Oligonucleotide Probes onto the Activated Dendrimeric Matrix 250 pmol/0.1 µl oligonucleotide probes solutions in 1% DIEA in water were placed onto the activated support media. The oligonucleotide probes were modified by C6 amino-linker at 3'-end.

Spotting was performed by pins (200 nl/spot). Following attachment of the oligonucleotide probes, the slides were incubated overnight in a humid chamber at 37° C. for the immobilization and afterwards washed with $H_2O$ and methanol (or ethanol).

5. Deactivation of Dendrimeric Matrix

The glass slides surface with the immobilized probes was deactivated by a 2 hrs treatment using a solution made of 6-amino-1-hexanol (50 mM) and DIEA (150 mM) in DMF. Finally, the DNA arrays were washed with DMF, acetone, water and dried. The deactivated glass slides with the immobilized probes (ready for the hybridization) could then be stored at 4° C. (shelf-life at 4° C. is at least 6 months).

Results

Coupling signal detection revealed that the coupling capacity of probes on the 3D dendrimeric matrices is much higher than on 3D gel-matrices, while coupling capacities of 3D-gel matrices and 2D matrices are comparable. The hybridization sensitivity with the ss compliment was arranged according to the following: 3D dendrimeric matrices>3D gel-matrices>2D aldehyde matrix.

In conclusion, the main advantages of the dendrimeric matrix are: 1) higher sensitivity compared to that of gel matrix (approximately 2 times); 2) following the stripping of the surface from the hybridized targets, the surface can be re-used. The shelf-life of the dendrimeric matrix is estimated to be 3 months.

Thus, the inventors determined dendrimeric matrix to be the most sensitive platform. Accordingly, all experiments conducted for the evaluation of the hybridization capacities were performed on the dendrimeric matrices manufactured by the inventors.

Example 2

Equalization of the Hybridization Capacity of the Probes

Hybridization kinetics of nucleic acids is temperature dependent, and the specificity and efficiency depend on the hybridization temperature. In order to determine melting temperature (Tm), the inventors used IDT OligoAnalyzer 3.1 (http://eu.idtdna.com/analyzer/Applications/OligoAnalyzer/Default.aspx) and Primer3 program (http://simgene.com/Primer3). For the Tm calculation, the program demands not only the oligonucleotide sequence, but the buffer conditions as well. Thus, Tm and consequently the hybridization temperature depend on the buffer composition. The length of each probe was established to range from 17 to 25 bases. The GC content was calculated and only probes with GC content between 40 and 60% were selected for further analysis.

The IDT OligoAnalyzer3.1 program was used for the estimation of the conditions of the hairpin formation. The formation of hairpins (intra-molecular self-structure of the probe) significantly prevents the process of hybridization and can decrease the sensitivity of the microarray. All designed probes were verified against the GenBank nucleic acid database for specificity using the basic local alignment search tool (BLAST) program (http://blast.ncbi.nlm.nih.gov/Blast.cgi).

While specific probes for target microorganisms could be generated following well established and above mentioned requirements, this would require an experimental confirmation of their equal hybridization capacity, as it has been estimated that between 21-34% of probes do not match their intended targets [22]. The main limitation of the existed programs and approaches for the prediction of melting temperature and consequently the hybridization temperature is that all these predictions are for free oligonucleotides but not for those bound to solid surfaces due to the limited knowledge on the thermodynamics of hybridization at solid liquid interfaces. This is the reason why probes with optimal predicted melting temperature do not necessarily perform the optimal hybridization, and this can generate biochips with irregular signal responses. Besides, it is not always possible to fit the specific probe/probes into the Tm range optimal for the most chosen probes.

The evaluation of the hybridization potential of each of the 38 probes was accomplished by using 16 single strand (ss) cassettes. ss cassettes present the lineal set of sequences complimentary to the studied set of probes. The Cy3 fluorescent dye was inserted at 5'-end of ss cassette during the synthesis. The number of probes included in each cassette ranged from 3 to 8, and the size varied from 65 to 142 bases (Table 2). The hybridization buffer was SSARC buffer (4×SSC [600 mM NaCl, 60 mM Na-citrate], 7.2% (v/v) Na-sarcosyl). The samples in the hybridization buffer were pre-heated to the hybridization temperature (45° C., 5 min). Hybridization on microscope slides was carried out under cover slips after the application of sample solution. The volume of the sample solution is calculated from 2 µl solution per 1 $cm^2$ of the covered square. Hybridization proceeded at 45° C. for 4 hrs. After hybridization the biochip was washed once for 2 min in 2×SSC+0.2% SDS, once for 2 min in 0.2×SSC+0.2% SDS, once for 2 min in 0.2×SSC at 25° C., and dried by centrifugation.

TABLE 2

The composition of the ss cassettes

| | | |
|---|---|---|
| N1 MIC1 cassette 5'-SRB1*ARC16SRNA * MCR1-3' (68 bases) | MIC1 SEQUENCE: 5'-CCA GGG CCT GTC CGC CAT CAA TAC * AGG AAT TGG CGG GGG AGC AC* CCAGGT GGC ATC AAG TTC GGA CAC-3' (SEQ ID NO: 39) | MIC 1 Cassette ss COMPLEMENT: 5 Cy3'-GTG TCC GAA CTT GATGCC ACC TGG GTGCTC CCC CGC CAA TTC CTGTAT TGA TGG CGG ACA GGC CCT GG-3' (SEQ ID NO: 40) |
| N2 HYD1 cassette: 5'-Dv*Dbulbus*Geobac*Shew*E.coli-3' (99 bases) | HYD1 SEQUENCE: 5'-CAC CCC TGC ATC GGC TGC AG * GCG CCA CCC TGC CGT TCA AC* CAC CCGGTG CAC TCC TGG A*ACA ACT GCC CAA CCG AGC GC* ACT CCT GCG CGC CAA TCC AG*-3' (SEQ ID NO: 41) | HYD 1 Cassette ss COMPLEMENT: Cy3 5'-CTG GAT TGG CGC GCA GGA GTG CGC TCG GTT GGG CAG TTG TTC CAG GAG TGC ACC GGG TGG TTG AAC GGC AGG GTG GCG CCT GCA GCC GAT GCAGGG GTG-3' (SEQ ID NO: 42) |
| N3 16SRNA cassetteA: 5'-Bacteria2* Bacteria1*Archea2*ShewRNA1 *ShewRNA2-3' (101 bases) | 16SRNA cassette A SEQUENCE: 5'-CAG TGA GGA ATT TTG CGC AC *GAC ATA AAG GCC ATG AGG CTG *TGT TGACTA CGT GTT ACT GAG * CGC GAT TGG ATG AAC CTA G*AGC TAA TCC CAC CTA GGT CA-3' (SEQ ID NO: 43) | 16SRNA Cassette A ss COMPLEMENT: Cy3 5'-TGA CCT AGG TGG GAT TAG CTC TAG GTT CAT CCA ATC GCG CTC AGT AAC ACG TAG TCA ACA CAG CCT CAT GGC CTT TAT GTC GTG CGC AAA ATT CCT CAC TG-3' (SEQ ID NO: 44) |
| N4 16SRNA cassetteB: 5'-GeoM*GeoS*16SRNA PR*Universal-3' (72 bases) | 16SRNA cassette B SEQUENCE: 5'-TTC GGG CCT TTT GTC ACC* TTC GGG CCT CCT GTC TTT C * GTC TGC CGT GAA AGT CCG* GAC GGG CGG TGT GTA CA-3' (SEQ ID NO: 45) | 16SRNA Cassette B ss COMPLEMENT: Cy3 5'-TGT ACA CAC CGC CCG TCC GGA CTT TCA CGG CAG ACG AAA GAC AGG AGG CCC GAA GGT GAC AAA AGG CCC GAA-3' (SEQ ID NO: 46) |
| N5 16SRNA cassetteC: 5'-Archeal*Geobacter*Universal-3' (56 bases) | 16SRNA cassette C SEQUENCE: 5'-GTG CTC CCC CGC CAA TTC AT* CTC ACG CAC TTC GGG ACC G*GAC GGG CGG TGT GTA CA-3' (SEQ ID NO: 47) | 16SRNA Cassette C ss COMPLEMENT: Cy3 5'-TGT ACA CAC CGC CCG TCC GGT CCC GAA GTG CGT GAG ATG AAT TGG CGG GGG AGC AC-3' (SEQ ID NO: 48) |
| N6 16SRNA cassetteD: 5'-Bacteria2*Archeal*Geobacter*GeoM*GeoS *ShewRNA1*Universal*16SRNA PR-3' (150 bases) | 16SRNA cassette D SEQUENCE: 5'-CAG TGA GGA ATT TTG CGC AC* GTG CTC CCC CGC CAA TTC AT * CTC ACGCAC TTC GGG | 16SRNA Cassette D ss COMPLEMENT: Cy3 5'-CGG ACT TTC ACG GCA GAC TGT ACA CAC CGC CCG TCC TAG GTT CAT |

TABLE 2-continued

The composition of the ss cassettes

| | | |
|---|---|---|
| | ACC G* TTC GGG CCT TTT GTC ACC* TTC GGG CCT CCT GTC TTTC* CGC GAT TGG ATG AAC CTA G* GAC GGG CGG TGT GTA CA* GTC TGC CGT GAA AGT CCG-3' (SEQ ID NO: 49) | CCA ATC GCG AAA AGA CAG GAG GCC CGA AGG TGA CAA AAG GCC CGA ACGGTC CCG AAG TGC GTG AGA TGA ATT GGC GGG GGA GCA CGT GCG CAA AATTCC TCA CTG-3' (SEQ ID NO: 50) |
| N7 NRB/FB cassette: 5'-nirS*narG*nirK*napA*FTHFS*a/bssA-3' (142 bases) | NRB/FB cassette SEQUENCE: 5'-CGC TGT TCG TCA AGA CCC ATC CG*CCA GCT TCT TCT ACG CCC ACA CCG*CCC GAC CCA CGT CGT ATT CAA CGG*CCG CGG CTA TGT GGG TCG AAA AAG* TGC ATG GCC AAG ACC CAA TAC AGC* TCG TCA TTG CCC CAT TTG GGG GC-3' (SEQ ID NO: 51) | NRB/FB cassette ss COMPLEMENT: Cy3 5'-GCC CCC AAA TGG GGC AAT GAC GAG CTG TAT TGG GTC TTG GCC ATG CAC TTT TTC GAC CCA CAT AGC CGC GGC CGT TGA ATA CGA CGT GGG TCG GGC GGT GTG GGC GTA GAA GAA GCT GGC GGA TGG GTC TTG ACG AAC AGC G-3' (SEQ ID NO: 52) |
| N8 HYD2 cassette: 5'-Dbacterium1 *Dbacter2 *Dtomaculum2*Dscoccus1 *Dsmicrobium1-3' (110 bases) | HYD2 SEQUENCE: 5'-CAC TGG AAC AGG CGA TCA AG*TCA CCT GGT GAA AAT CGG ACT*CAC GCA TCG GGG AGA GGG TGG*CAC CTC CTC CAA AAC CGG GGA AGG*CCA CAA CCT GGC CAT CCC GGA AAT-3' (SEQ ID NO: 53) | HYD 2 Cassette ss COMPLEMENT: Cy3 5'-ATT CCC GGG ATG GCC AGG TTG TGG CCT TCC CCG GTT TTG GAG GAG GTG CCA CCC TCT CCC CGA TGC GTG AGT CCG ATT TTC ACC AGG TGA CTT GAT CGC CTG TTC AGT G-3' (SEQ ID NO: 54) |
| N9 16S SRB_16S CONS cassette: 5'-Dv 16S_1*Dbacterium 16S_2*16SCONS_1*16SCONS_2 *16SCONS_3-3' (95 bases) | 16S SRB_16S CONS cassette SEQUENCE: 5'-CAA TCC GGA CTG GGACGG*GCG CGT TGT ACA TAC CAT*CCT ACG GGA GGCAGC AG*ATT ACC GCG GCT GCT GG*CGG CAG GCC TAA CAC ATG CAA GTC G-3' (SEQ ID NO: 55) | 16S SRB_16S CONS cassette ss COMPLEMENT: Cy3 5'-CGA CTT GCA TGT GTT AGG CCT GCC GCC AGC AGC CGC GGT AAT CTGCTG CCT CCC GTA GGA TGG TAT GTA CAA CGC GCC CGT CCC AGT CCG GAT TG-3' (SEQ ID NO: 56) |
| N10 All 16S RNA_1: 5'-Bacteria1*Bacteria2*Archea1 *Archea2* ARC16SRNA*Universal-3' (119 bases) | All 16S RNA_1 cassette SEQUENCE: 5'-GAC ATA AAG GCC ATG AGG CTG* CAG TGA GGA ATT TGC GC AC*GTG CTC CCC CGC CAA TTC AT*TGT TGA CTA CGT GTT ACT GAG* AGG AAT GGG CGG GGGAGC AC* GAC GGG CGG TGT GTA CA-3' (SEQ ID NO: 57) | All 16S RNA_1 cassette ss COMPLEMENT: Cy3 5'-TGT ACA CAC CGC CCG TCG TGC TCC CCC GCC AAT TCC TCT CAG TAACAC GTA GTC AAC AAT GAA TTG GCG GGG GAG CAC GTG CGC AAA ATT CCT CAC TGC AGC CTC ATG GCC TTT ATG TC-3' (SEQ ID NO: 58) |
| N11 All 16S RNA_2: 5'-16SRNA PR*Geobacter* GeoM*GeoS* ShewRNA1 *ShewRNA2-3' (113 bases) | All 16S RNA_2 cassette SEQUENCE: 5'-GTC TGC CGT GAA AGT CCG* CTC ACG CAC TTC GGG ACC G* TTC GGG CCTTTT GTC ACC* TTC GGG CCT CCT GTC TTT C* CGC GAT TGG ATG AAC CTA G*AGC TAA TCC | All 16S RNA_2 cassette ss COMPLEMENT: Cy3 5'-TGA CCT AGG TGG GAT TAG CTC TAG GTT CAT CCA ATC GCG AAA GAC AGG AGG CCC GAA GGT GAC AAA AGG CCC GAA CCG AAG TGC |

TABLE 2-continued

The composition of the ss cassettes

| | | CAC CTA GGT CA-3'<br>(SEQ ID NO: 59) | GTGAGC GGA CTT<br>TCA CGG CAG AC-3'<br>(SEQ ID NO: 60) |
|---|---|---|---|
| N12 | All HYD_3A: 5'-Dv*Dbulbus*Dtomaculum2<br>*Dscoccus1-3' (85 bases) | All HYD_3A cassette<br>SEQUENCE:<br>5'-CAC CCC TGC ATC<br>GGC TGC AG*GCG CCA<br>CCC TGC CGT TCA<br>AC*CAC GCA<br>TCG GGG AGA GGG<br>TGG* CAC CTC CTC<br>CAA AAC CGG GGA<br>AGG-3' (SEQ ID NO: 61) | All HYD_3A cassette ss<br>COMPLEMENT:<br>Cy3 5'-CCT TCC CCG<br>GTT TTG GAG GAG<br>GTG CCA CCC TCT<br>CCC CGA TGC GTG<br>GTT GAA CGG CAG<br>GGT GGC GCC TGC<br>AGC CGA TGC AGG<br>GGT G-3' (SEQ ID NO: 62) |
| N13 | All HYD_3B: 5'-Dsmicrobium1*Dbacterium1<br>*Dbacter2-3' (65 bases) | All HYD_3B cassette<br>SEQUENCE:<br>5'-CCA CAA CCT GGC<br>CAT CCC GGA AAT*<br>CAC TGG AAC<br>CGA TCA AG*TCACCT<br>GGT GAA AAT<br>ACT-3' (SEQ ID NO: 63) | All HYD_3B cassette ss<br>COMPLEMENT:<br>Cy3 5'-AGT CCG ATT<br>TTC ACC AGG TGA<br>AGG CTT GAT CGC TG<br>TTC CAG TGA<br>CGG TTTCCG GGA TGG<br>CCA GGT TGT GG-3'<br>(SEQ ID NO: 64) |
| N14 | All HYD_4: 5'-<br>Geobac*Shew*E.coli*FirmicutishydA-3'<br>(83 bases) | All HYD_4 cassette<br>SEQUENCE:<br>5'-CAC CCG GTG CAC<br>TCC TGG A*ACA ACT<br>GCC CAA CCG AGC<br>GC*ACT CCT GCG<br>CGC CAA TCC AG*AGG<br>CGG CGA GCA TGA<br>TCC AGC AAT-3'<br>(SEQ ID NO: 65) | All HYD_4 cassette ss<br>COMPLEMENT:<br>Cy3 5'-ATT GCT GGA<br>TCA TGC TCG CCG<br>CCT CTG GAT TGG<br>CGC GCA GGA<br>GTGCGC TCG GTT<br>GGG CAG TTG TTC<br>CAG GAG TGC ACC<br>GGG TG-3' (SEQ ID<br>NO: 66) |
| N15 | Funcgenes_1: 5'-nirS*narG*nirK<br>*napA-3' (95 bases) | Funcgenesi cassette<br>SEQUENCE:<br>5'-CGC TGT TCG TCA<br>AGA CCC ATC CG*CCA<br>GCT TCT TCT ACG CCC<br>ACA CCG*CCC GAC<br>CCA CGT CGT ATT CAA<br>CGG* CCG CGG CTA<br>TGT GGG TCG AAA<br>AAG-3' (SEQ ID NO: 67) | Funcgenesi cassette ss<br>COMPLEMENT:<br>Cy3 5'-CTT TTT CGA<br>CCC ACA TAG CCG<br>CGG CCG TTG AAT<br>ACG ACG TGG<br>GTCGGG CGG TGT<br>GGG CGT AGA AGA<br>AGC TGG CGG ATG<br>GGT CTT GAC GAA<br>CAGCG-3' (SEQ ID NO: 68) |
| N16 | Funcgenes_2: 5'-<br>SRB1*FTHFS *a/bssA*MCR1*DSR1<br>*DSR2-3' (128 bases) | Funcgenes_2 cassette<br>SEQUENCE:<br>5'-CCA GGG CCT GTC<br>CGC CAT CAA<br>TAC*TGC ATG GCC<br>AAG ACC CAA TAC<br>AGC*TCG TCA TTG<br>CCC CAT TTG GGG GC*<br>CCA GGT GGC ATC<br>AAG TTC GGA<br>CAC*GTG TAG CAG<br>TTA CCG CA* ACC CAC<br>TGG AAG CAC G-3'<br>(SEQ ID NO: 69) | Funcgenes_2 cassette ss<br>COMPLEMENT:<br>Cy3 5'-CGT GCT TCC<br>AGT GGG TTG CGG<br>TAA CTG CTA CAC<br>GTG TCC GAA CTT<br>GAT GCC ACC TGG<br>GCC CCC AAA TGG<br>GGC AAT GAC GAG<br>CTG TAT TGG GTC<br>TTG GCC ATG CAG<br>TAT TGA TGG CGG<br>ACA GGC CCT GG-3'<br>(SEQ ID NO: 70) |

It is noted that the "*" merely indicate the end of one probe and the start of an adjacent probe in the cassette, and do not indicate any sequence modification.

The signal from the probe SRB1 for the identification of SRB in the bacterial consortia was used as a gold standard. The similar hybridization behavior of a cassette probe was used in the content of different cassettes. Moreover, this probe was designed in the mixture of randomly selected cassettes implicitly points with the absence of cross-hybridization between all studied probes.

The variations in the fluorescent intensities on a biochip, coming from probe's size and nucleotide sequence differences, are determined by the cassette method. 35 probes with similar fluorescent intensities (or binding capacity) have been chosen from the tested 38 probes for the identification of main bacterial groups involved in the biocorrosion (Table 3).

TABLE 3

35 oligonucleotide probes selected on the basis of the similar binding capacity estimated by ss cassette approach.

|  | Group | Targeted organism | Targeted gene | Probe name | Sequence 5'-3' | References |
|---|---|---|---|---|---|---|
| 1 | SRB (Sulfate-Reducing Bacteria) | SRB | APR-reductase | SRB1 | CCA GGG CCT GTC CGC CAT CAATAC (SEQ ID NO: 1) | Zinkevich V., et al., FEMS Microbiol Ecol (2000) 34:147-155 |
| 2 |  | SRB | DSR-reductase | DRS1 | GTG TAG CAG TTA CCG CA (SEQ ID NO: 2) | Klein M., et al., Journal of Bacteriology, (2001)183: 6028- |
| 3 |  | SRB | DSR-reductase | DRS2 | ACC CAC TGG AAG CAC G (SEQ ID NO: 3) | Klein M., et al., Journal of Bacteriology, (2001)183: 6028-6035 |
| 4 |  | Desulfobvibrio | hynB (periplasmic Ni,Fe hydrogenase) | Dv | CAC CCC TGC ATC GGC TGC AG (SEQ ID NO: 4) | de novo |
| 5 |  | Desulfo-bacterium | hynB (periplasmic Ni, Fe hydrogenase) | Dbacterium1 | CAC TGG AAC AG CGA TCA AG (SEQ ID NO: 5) | de novo |
| 6 |  | Desulfobulbus | hydA (Ni, Fe-hydrogenase) | Dbulbus | GCG CCA TGC TGC CGT TCA AC (SEQ ID NO: 6) | de novo |
| 7 |  | Desolfobacter | hydA (Ni, Fe-hydrogenase) | Dbacter2 | TCA CCT GGT GAA AAT CGG ACT (SEQ ID NO: 7) | de novo |
| 8 |  | Desulfo-microbium | hydA (Ni, Fe-hydrogenase) | Dsmicrobium1 | CCA CAA CCT GGC CAT CCC GGA AAT (SEQ ID NO: 8) | de novo |
| 9 |  | Desulfo-tomaculum | hydA (Fe-hydrogenase) | Dtomaculum2 | CAC GCA TCG GGG AGA GGG TGG (SEQ ID NO: 9) | de novo |
| 10 |  | Desulfococcus | hydB gene of hydrogenase accessory protein HypB | Dscoccus | CAC CTC CTC CAA AAC CGG GGA AGG (SEQ ID NO: 10) | de novo |
| 11 |  | Desulfobibrio | 16S rRNA gene for Desulfovibrio spp. (including Dv. vulgaris, Dv. desuluricans) | Dv 16S_1 | CAA TCC GGA CTG GGA CGG (SEQ ID NO: 11) | Loy A., et al., Appl Environ Microbial (2002)68:5064-5081 |
| 12 |  | Desulfo-bacterium | 16S rRNA gene for Desulfobacterium spp | Dbacterium 16S_2 | GCG CGT TGT ACA TAC CAT (SEQ ID NO: 12) | Loy A., et al., Appl Environ Microbial (2002)68:5064-5081 |
| 13 | Archaea | Methanogenic Archaea | Methyl coenzyme M reductase (mcr) | MCR1 | CCA GGT GC ATC AAG TTC GGA CAC (SEQ ID NO: 13) | de novo |
| 14 |  | Archaea | 16S rRNA gene | Archaea1 | GTG CTC CCC CGC CAA TTC AT (SEQ ID NO: 14) | Loy A., et al., Appl Environ Microbial (2002)68:5064-5081 |
| 15 |  | Archaea | 16S rRNA gene | Archaea2 | TGT TGA CTA CGT GTT ACT GAG (SEQ ID NO: 15) | Loy A., et al., Appl Environ Microbial (2002)68:5064-5081 |
| 16 |  | Archaea | 16S rRNA gene | ARC16SRNA | AGG AAT TGG CGG GGG AGC AC (SEQ ID NO: 16) | Raskin L., et al. Applied and Environmental Microbiology (1994) |

TABLE 3-continued 35 oligonucleotide probes selected on the basis of the similar binding capacity estimated by ss cassette approach.

| | Group | Targeted organism | Targeted geme | Probe name | Sequence 5'-3' | References |
|---|---|---|---|---|---|---|
| 17 | MRB (Metal-Reducing Bacteria) | *Geobacter* spp | hydA (Ni, Fe-hydrogenase) | Geobac | CAC CCG GTGCAC TCC TGG A (SEQ ID NO: 17) | de novo |
| 18 | | *Shewanella* spp | hydA (Ni, Fe-hydrogenase) | Shew | ACA ACT GCC CAA CCG AGC GC | de novo |
| 19 | | *G. sulfurreducens* | 16S rRNA gene | GeoS | TTC GGG CCT CCT GTC TTT C (SEQ ID NO: 20) | de novo |
| 20 | | *G. metalli-reducens* | 16S rRNA gene | GeoM | TTC GGG CCT TTT GTC ACC (SEQ ID NO: 21) | de novo |
| 21 | | *Shewanella* spp | 16S rRNA gene | ShewRNA1 | CGC GAT TGG ATG AAC CTA G (SEEQ ID NO: 22) | de novo |
| 22 | | *Arthrobacter* spp | 16S rRNA gene | 16SRNA PR | GTC TGC CGT GAA AGT CCG (SEQ ID NO: 24) | de novo |
| 23 | FB (Fermentative bacteria) | Acetogenic | formyltetrahydrofolate synthetase (fthfs) | FTHFS | TGC ATG GCC AAG ACC CAA TAC AGC (SEQ ID NO: 25) | Salmassi TM., et al. Microbiology (2003) 149:2529-2537 |
| 24 | | Hydrocarbon-degrading | alkylsuccinate synthase and benzylsuccinate synthase alpha subunits (assA/bssA) | a/bssA | TCG TCA TTG CCC CAT TTG GGG GC (SEQ ID NO: 26) | Callaghan AV., et al. Environ Sci and Technol (2010) 44: 7287-7294 |
| 25 | | *Firmicutes* | hydA (Fe-hydrogenase) | FirmicutishydA | AGG CGG CGA GCA TGA TCC AGC AAT (SEQ ID NO: 27) | de novo |
| 26 | | *E.coli* | hyaA | E.coli | ACT CCT GCG CGC CAA TCC AG (SEQ ID NO: 28) | de novo |
| 27 | NRB (Nitrate Reducing Bacteria) | NRB (Nitrate Reducing) | nitrite reductase (nirS) | nirS | CGC TGT TCG TCA AGA CCC ATC CG (SEQ ID NO: 29) | de novo |
| 28 | | NRB (Nitrate Reducing) | nitrite reductase (nirK) | nirK | CCC GAC CCA CGT CGT ATT CAA CGG (SEQ ID NO: 30) | de novo |
| 29 | | NRB (Nitrate Reducing) | nitrite reductase (narG) | napG | CCA GCT TCT TCT ACG CCC ACA CCG (SEQ ID NO: 31) | de novo |
| 30 | | NRB (Nitrate Reducing) | nitrite reductase (napA) | napA | CCG CGG CTA TGT GGG TCG AAA AAG (SEQ ID NO: 32) | de novo |
| 31 | Bacteria | Bacteria | 16S rRNA gene | Bacteria1 | GAC ATA AAG GCC ATG AGG CTG (SEQ ID NO: 33) | Loy A., et al., Appl Environ Microbial (2002) 68:5064-5081 |
| 32 | | Bacteria | 16S rRNA gene | Bacteria2 | CAG TGA GGA ATT TTG CGC AC (SEQ ID NO: 34) | Loy A., et al., Appl Environ Microbial (2002) 68:5064-5081 |
| 33 | | Bacteria | 16S rRNA gene | 16SCONS_1 | CCT ACG GGA GGC AGC AG (SEQ ID NO: 36) | Muyzer G., et al., Appl and Environ Micobiol. (1993) 59:695-700 |
| 34 | | Bacteria | 16S rRNA gene | 16SCONS_2 | ATT ACC GCG GCT GCT GG (SEQ ID NO: 37) | Muyzer G., et al., Appl and Environ Micobiol. (1993) 59:695-700 |

TABLE 3-continued 35 oligonucleotide probes selected on the basis of the similar binding capacity estimated by ss cassette approach.

| Group | Targeted organism | Targeted geme | Probe name | Sequence 5'-3' | References |
|---|---|---|---|---|---|
| 35 | Bacteria | 16S rRNA gene | 16SCONS_3 | CGG CAG GCC TAA CAC ATG CAA GTC G (SEQ ID NO: 38) | Avaniss-Aghajani E., et al., BioTechniques (1994)17:144-149 |

Example 3

Optimization of the Probes Using Extended ssDNA Approach

As previously mentioned, the difficulty of the microarray approach is that all probes are hybridized simultaneously, but specific hybridization conditions often vary between probes. The hybridization signal intensity in the real environment has been estimated for the selected probes characterized by equal hybridization capacity. The probes are embedded in the fragment of appropriate DNA and not in the set of compliments as it is in the case of cassette. For this reason, the extended ssDNA approach has been developed.

The approach is based on the hybridization of the short (100-200 bases) single stranded ssDNA (PCR fragments) with the appropriate oligonucleotide probe on the biochip. The sequence complimentary to the appropriate probe is imbedded in ssDNA fragments. The SRB strains, obtained from DSMZ (Deutsche Sammlung von Mikroorganismen und Zellkulturen) collection, the probes and PCR primers are listed in Table 4. Individual gene-specific PCR primers were designed using Primer3Plus software (http://www.bioinformatics.nl/cgi-bin/primer3plus/primer3plus.cgi). The sequences complementary to the biochip probes were embedded in the one of PCR amplicon strains, which was Cy3 labeled.

TABLE 4

DNA, oligonucleotide probes and PCR primers

| DNA | Target gene GenBank accession no. | Probe name | Sequence 5'-3' | PCR Primers name | Sequence 5'-3' | PCR fragment size (bp) |
|---|---|---|---|---|---|---|
| Desulfovibrio alaskensis, DSM 16109 | hynB1 (periplasmic Ni, Fe hydrogenase); CP000112 | Dv. | CAC CCC TGC ATC GGC TGC AG (SEQ ID NO: 4) | For1<br><br>Rev1 | CAA AGG GTG TCT GTA CG (SEQ ID NO: 71)<br>CTC ATG GCA TCC CAG AAA TC (SEQ ID NO: 72) | 150 |
| Desulfobacterium autotropicum, DSM 3382 | hynB (periplasmic Ni, Fe hydrogenase); CP001087 | D-bacterium1 | CAC TGG AAC AGG CGA TCA AG (SEQ ID NO: 5) | For2<br><br>Rev2_Cy3 | CTT GAG ACC ATT TCG GTT GA (SEQ ID NO: 73)<br>GGC GCC GTT ATA GGC TGT AG (SEQ ID NO: 74) | 150 |
| Desulfobulbus propionicus, DSM 2032 | hydA (Ni, Fe-hydrogenase); CP002364 | Dbulbus | GCG CCA CCC TGC CGT TCA AC (SEQ ID NO: 6) | For1<br><br>Rev1_Cy3 | CTC TAC AAA CTG GGG TGC AAG (SEQ ID NO: 75)<br>GAC CTT TGC CTT GGA AAACA (SEQ ID NO: 76) | 165 |
| Desulfobacter postgatei, DSM 2034 | hydA (Ni, Fe-hydrogenase); NZ_CM001488 | Dbacter2 | TCA CCT GGT GAA AAT CGGACT (SEQ ID NO: 7) | For1<br><br>Rev1_Cy3 | TCA CCT GGT GAA AAT CGG ACT (SEQ ID NO: 85)<br>CCA GGT CTG TCC ACT GTT CC (SEQ ID NO: 77) | 220 |
| Desulfomicrobium baculatum, DSM 4028 | hydA (Ni, Fe-hydrogenase); CP001629 | Dsmicrobium1 | CCA CAA CCT GGC CAT CCC GGA AAT (SEQ ID NO: 8) | For1_Cy3<br><br>Rev1 | GTT TCG CCG AAG AAC ATG A (SEQ ID NO: 78)<br>CCGC CCA ATC CCT ACA ACC T (SEQ ID NO: 79) | 109 |

TABLE 4-continued

DNA, oligonucleotide probes and PCR primers

| DNA | Target gene GenBank accession no. | Probe name | Sequence 5'-3' | PCR Primers name | Sequence 5'-3' | PCR fragment size (bp) |
|---|---|---|---|---|---|---|
| Desulfo-maculum ruminis, DSM 2154 | hydA (Ni, Fe-hydrogenase); CP002780 | Dtomaculum1 | ACC TAT GCC GAT TGT CCC CG (SEQ ID NO: 80) | For2_Cy3<br><br>Rev2 | GGA AAT TCC GGA CTG GTA CA (SEQ ID NO: 81)<br>GAGGGAGTCTTCT CCAAGCA (SEQ ID NO: 82) | 170 |

Figure 1:
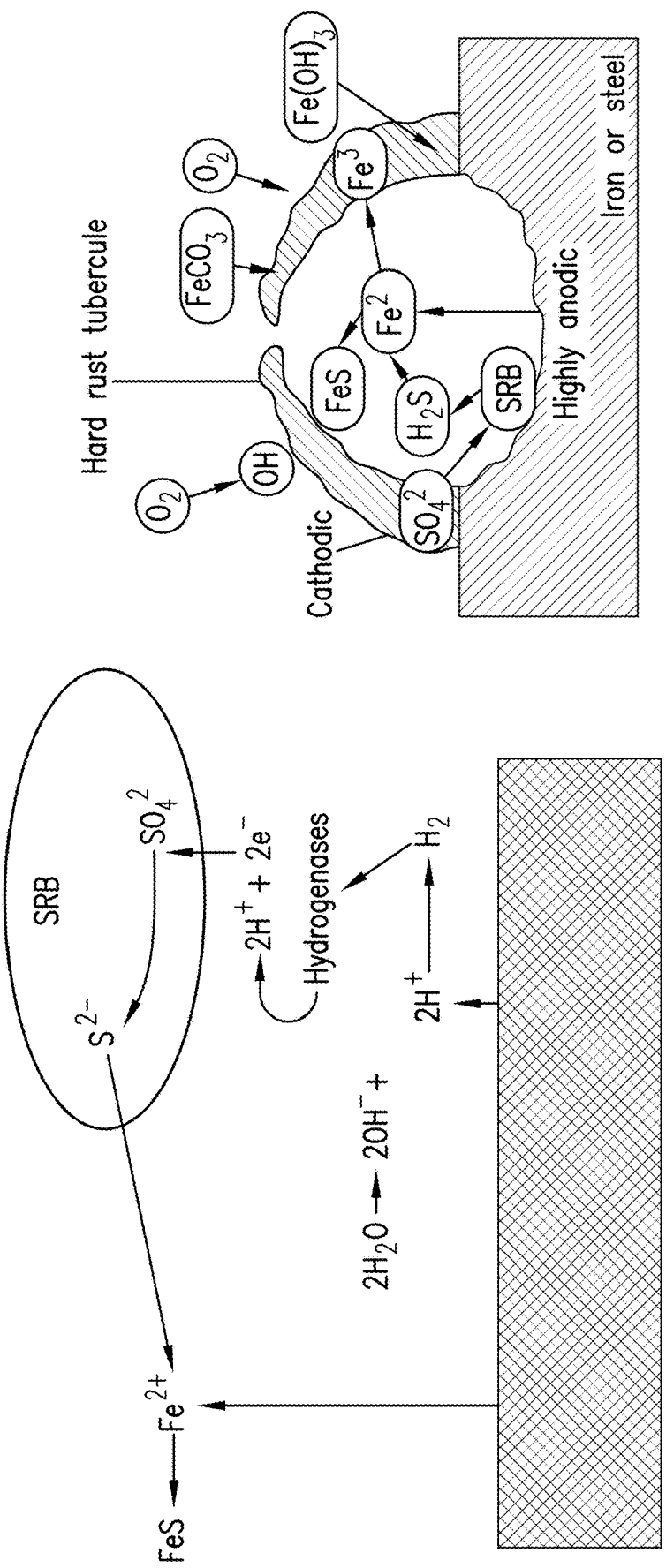
FIG. 1 is a schematic showing the impact of SRB on the corrosion (cathodic and anodic processes).
Figure 2:
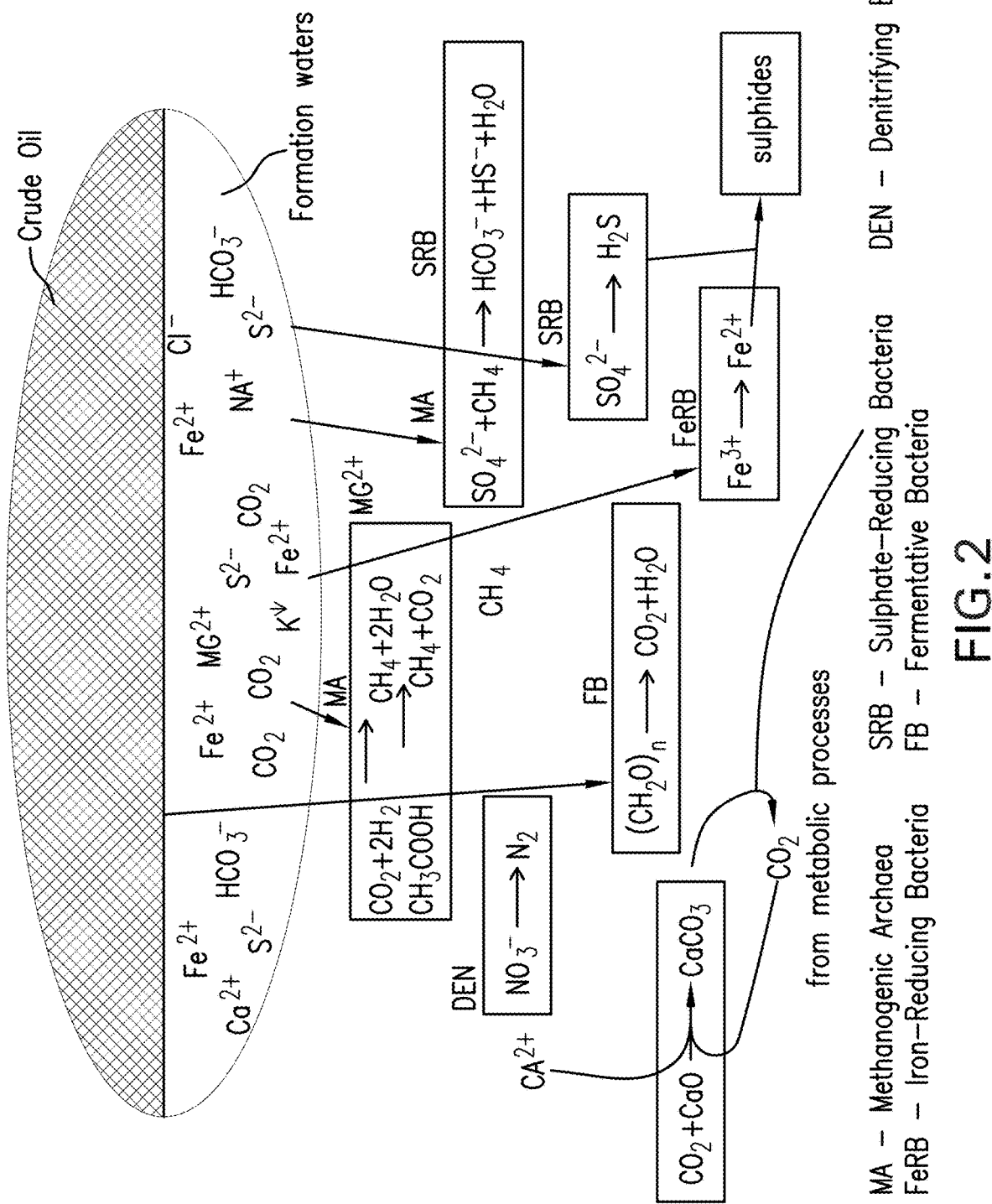
FIG. 2 is a schematic showing microbial assemblage that participates in biocorrosion.
Figure 3:
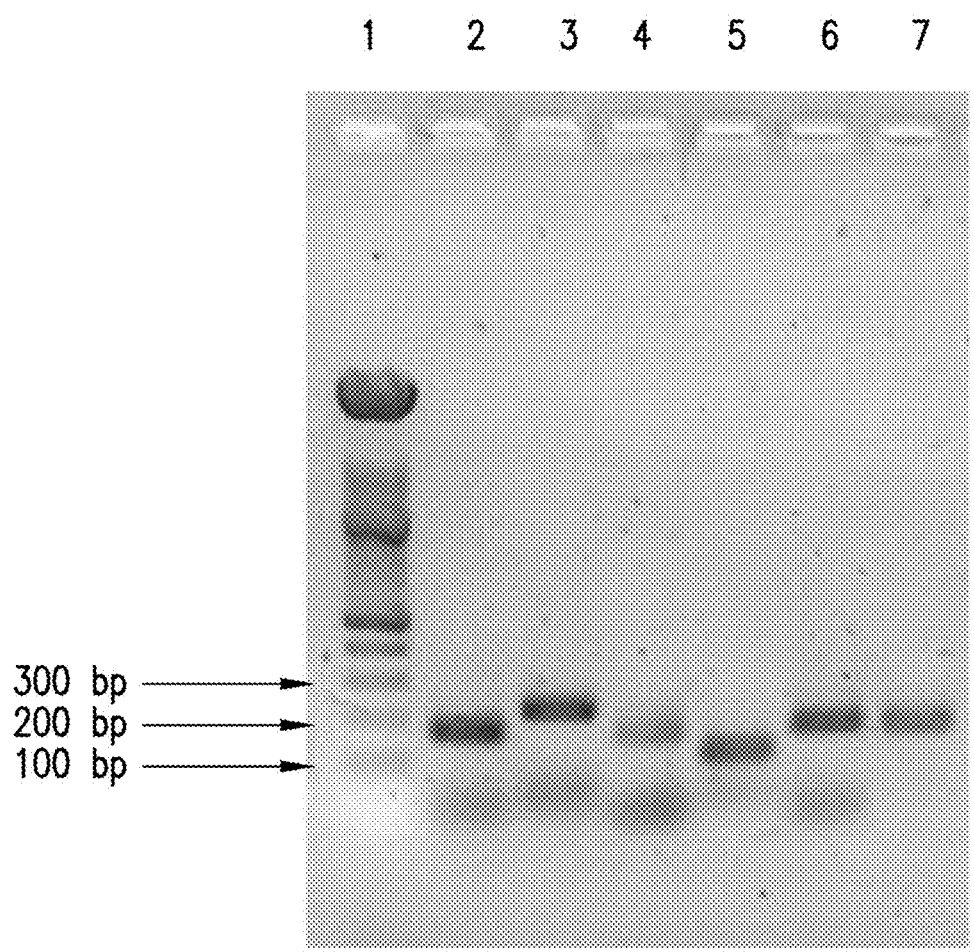
FIG. 3 is an image showing agarose gel analysis of PCR fragments following DNA amplification. Lane 1 corresponds to Gene Ruler 100 bp Plus DNA Ladder (Thermo Scientific, USA); lane 2 corresponds to a PCR fragment (165 bp) amplified on *Desulfobulbus* DNA; lane 3 corresponds to a PCR fragment (220 bp) amplified on *Desulfobacter* DNA; lane 4 corresponds to a PCR fragment (150 bp) amplified on *Desulfobacterium* DNA; lane 5 corresponds to a PCR fragment (109 bp) amplified on *Desulfomicrobium* DNA; lane 6 corresponds to a PCR fragment (170 bp) amplified on *Desulfotomaculum* DNA; and lane 7 corresponds to a PCR fragment (150 bp) amplified on *Desulfovibrio* DNA.

The approach included two PCR reactions: standard and primer extension reactions. Standard PCR and primer extension reactions were performed on each DNA presented in the Table 4. The 1$^{st}$ standard PCR mixture (50 µl) contained 1×iProof High-Fidelity Master Mix (Bio-Rad Laboratories, USA) with 1.5 mM $MgCl_2$, 200 µM (each) deoxynucleoside thriphosphate, 500 nM each primer, 50 ng of DNA template. PCR amplification was conducted using the following conditions identical for each primer pair: an initial denaturation step (30 s, 98° C.) was followed by 35 cycles of denaturation (10 s, 98° C.), annealing (20 s, 60° C.), and extension (15 s, 72° C.) and one terminal extension step (10 min, 72° C.). The results of the PCR amplification were assessed using agarose gel analysis of PCR fragments following DNA amplification (1.5% agarose gel, 1×TAE running buffer, ethidium bromide staining) and are shown in FIG. 3.

Amplified DNA was purified using a PureLink Quick PCR Purification Kit (Invitrogen, USA) before single strand DNA synthesis, and used as the template DNA in the primer extension reaction. Single strand DNA samples for hybridization were synthesized using the primer extension reaction with iProof DNA polymerase in the presence of subsequent reverse or forward primers labeled by Cy3 dye (Table 4). The use of the labeled reverse or forward primer in the primer extension reaction is governed by the position of the sequence complimentary to the probe on the 1st or the 2nd strain of the template (ds PCR amplicon) DNA. The reaction was performed in 50 µl containing 1× iProof High-Fidelity Master Mix (Bio-Rad Laboratories, USA) with 1.5 mM $MgCl_2$, 200 µM (each) deoxynucleoside thriphosphate, 1000 nM Cy3 labeled primer (Table 4), 120 ng of DNA template. Amplification protocol was the same for all primer extension reactions, and was the same as for amplification of the first standard PCR. iProof DNA polymerase (Bio-Rad Laboratories, USA) equalizes the PCR conditions for all ran reactions and speeds the reaction. The 35 cycles PCR is completed in 1 hour. Amplified ss PCR fragment was purified using a PureLink Quick PCR Purification Kit (Invitrogen, USA) and precipitated by 10 volumes of 2% $LiClO_4$ in acetone for 30 min at −20° C. The pellet was collected by centrifugation at 15,000 rpm for 30 min, washed 1 time with acetone and air dried. The pellet represents the labeled ssDNA ready for hybridization on the biochip. Each ssDNA fragment contains the sequence complimentary to the appropriate probe on the biochip in the environment of the other real-life sequences that models the hybridization of specific target DNA on the biochip.

To assess the hybridization signal from the oligoprobes (Table 4) each gene was amplified with single PCR. The amplified PCR of each gene was then used as a template in primer extension reaction to create single strand DNA. As the result, the single strand DNA of each gene was labeled and hybridized separately on the small microarray consisting of 6 probes, forming a part of MIC-biochip. In summary, six genes of different SRB DNA were amplified and hybridized separately with the biochip (FIG. 4).

The quantity of DNA and fluorophore Cy3 was estimated spectrophotometrically for each ssPCR fragment. The equal quantity of each labeled ssDNA was dissolved in hybridization buffer (1 M GuSCN (guanidine thyocianate), 5 mM EDTA, 50 mM HEPES (pH 7.5), 0.2 mg/ml BSA (bovine serum albumin). The mixture was denatured at 95° C. for 5 min, and chilled on ice for 2 min. The sample was placed onto oligonucleotide probes array slides at 25° C. and covered with a glass cover slip. After hybridization for 4 hours at 25° C. in Arrayit hybridization chamber (Arrayit Corporation, USA), the slides were rinsed with 4×SSC, 7.2% Sarcosyl (Sodium lauroyl sarcosinate) for 30 sec, afterwards, the slides were washed with 0.2×SSC at room temperature for 30 sec, spun-dry at 1000 rpm for 1 min before analyzing by the portable microarray reader PA5000 (Aurora Photonics, USA). The results are presented in FIG. 4.

The following detailed protocol was used for the extended ssDNA approach:
1. 1st standard PCR: total reaction volume is 50 µl
1.1 Mix:
   50 ng (X µl volume) of dissolved genomic DNA
   +25 µl 2× iProof High-Fidelity Master Mix (Bio-Rad)
   +200 µM (each) deoxynucleoside thriphosphate (Y µl volume)
   +500 nM each primer (Z µl volume)
   +Sterile water up to 50 µl
1.2 PCR conditions: total cycles 35
   one initial denaturation step (30 s, 98° C.)
   35 repeats of: denaturation (10 s, 98° C.), annealing (20 s, 60° C.), and extension (15 s, 72° C.)
   one terminal extension step (10 min, 72° C.)
1.3 Purify PCR product by using PureLink Quick PCR Purification Kit (Invitrogen, USA)
2. 2$^{nd}$ primer extension PCR: total reaction buffer is 50 µl
2.1 Mix:
   120 ng (X µl volume) of the purified ds DNA after 1st PCR
   +25 µl 2×iProof High-Fidelity Master Mix (Bio-Rad)
   +200 µM (each) deoxynucleoside thriphosphate (Y µl volume)
   +1000 nM Cy3 labeled primer for the extension only of one DNA strand (Z µl volume)
   +Sterile water up to 50 µl
2.2 PCR conditions: total cycles 35
   one initial denaturation step (30 s, 98° C.)
   35 repeats of: denaturation (10 s, 98° C.), annealing (20 s, 60° C.), and extension (15 s, 72° C.)
   one terminal extension step (10 min, 72° C.)

2.3 Purify PCR product by using PureLink Quick PCR Purification Kit (Invitrogen, USA)
2.4 Pellet of the purified ss DNA by adding 10 volumes of 2% $LiClO_4$ in acetone for at least 30 min at −20° C.
2.5 Collect DNA by centrifugation at 15,000 rpm for 20 min at 4° C.
2.6 Wash the pellet once with 1 ml acetone and leave for drying on air
3. Hybridization:
3.1 Dissolve the pellet in the hybridization buffer (1 M GuSCN (guanidine thyocianate), 5 mM EDTA, 50 mM HEPES (pH 7.5), 0.2 mg/ml BSA (bovine serum albumin), heat at 95° C. for 5 min followed by immediate chilling on ice for 2 min
3.2 Hybridization at 25° C. for 4 hr
3.3 Washing 1 time in 4×SSC, 7.2% Sarcosyl for 30 sec; 1 time in 0.2×SSC for 30 sec Shaking.

As shown in FIG. 4, the signal to noise ratio (S/N) was equal within reasonable errors for all six ssDNAs, and every ssDNA matched only to the appropriate probes. The approach was validated with a representative set of SRB-group probes and six commercially available DNAs. All gene-specific probes for MIC-biochip were designed to minimize possible cross-hybridization. The results, obtained by extended ssDNA approach, correlate with the results obtained by the cassette method for the selected probes.

The developed approach provides an opportunity to prepare the samples for the fine-tuning of the hybridization signal intensity under practical conditions, such as in 3 hours by using available DNA strains.

Example 4

Development of DNA Preparation Method for Biochip Analysis

The sensitivity of microarray depends on the quantity of the probes, the type of the biochip matrix, and the quantity of the labeled target DNA. In the present Example, all experiments for the evaluation of DNA preparation for biochip analysis, as well as analysis of environmental samples on different biochip prototypes were performed on the 3D dendrimeric matrices manufactured in the inventor's laboratory.

Target DNA amplification before hybridization leads to stronger signals and allows for detection of specific targets even if they are present in low abundance. The steps of random fragmentation of DNA and its fluorescent labeling precede the hybridization of DNA fragments with the immobilized probes onto the matrix for the biochip visualization. Ten protocols with different combinations of DNA amplification, fragmentation and labeling procedures were designed and tested by using the pure bacterial cultures (*Desulfovibrio indonensis* and *E. coli* BP) and the environmental samples. The most optimal procedure was used for analysis of environmental samples on different biochip prototypes.

While it is understood that each of the steps outlined below and in FIG. 5 can be performed using various methods and reagents used in the art, the inventors have optimized N10 protocol, which was finally adopted for implementation in the evaluation of MIC BioChip prototypes (Example 6).

1st amplification was performed by using Illustra™ GenomiPhi HY DNA Amplification Kit (Catalog. No.: 25-6600-22 GE Healthcare, Life Science, USA) and subsequent purification. Fragmentation of the amplified DNA was performed by using other NEBNext dsDNA Fragmentase (Catalog. No.: M0348S New England Biolabs, USA), other FastDigest SaqAI (Catalog. No.: #FD2174 Thermo Scientific, USA) and subsequent purification; and 2nd amplification and labelling was performed simultaneously by using BioPrime® Plus Array CGH Genomic Labelling System (Catalog. No.: 18095-13 Invitrogen, USA).

Detailed N10 Protocol for DNA Amplification, Fragmentation and Labeling:
1. 1st Amplification: total reaction volume is 50 μl
   1.1 Mix 2.5 μl of genomic DNA+22.5 μl Sample Buffer and incubate at 95° C. for 3 min and immediately chill on ice. The amount of genomic DNA per reaction can be varied from 10 to 100 ng with the satisfactory results;
   1.2 Add 25 μl of Reaction Buffer+2.5 μl of Enzyme mix;
   1.3 Incubate at 30° C. for 4 hours;
   1.4 Heat the samples to 65° C. for 10 minutes then cool to 4° C. for the enzyme inactivation;
   1.5 Check the extent of amplification, take 5 μl for the agarose gel;
   1.6 Purify the amplified DNA by magnetic beads from the ChargeSwitch® gDNA Mini Bacteria Kit or PureLink Quick PCR Purification Kit (Invitrogen, USA) according to the manufacturer's instructions;
   1.7 Take DNA spectra to estimate yield.
2. Fragmentation by dsDNA Fragmentase: total reaction buffer is 20 μl
   2.1 Mix X μl of genomic amplified DNA (do not exceed 2 μg)+2 μl 10×dsDNA Fragmentase Reaction Buffer+4 μl 200 mM $MgCl_2$+Sterile water up to 20 μl;
   2.2 Digest at 37° C. for 10 min;
   2.3 Check the extent of digestion, take 2.5 μl for the agarose gel;
   2.4 Purify product of digestion by using PureLink Quick PCR Purification Kit (Invitrogen, USA);
   2.5 Take DNA spectra to estimate yield.
OR
2. Fragmentation by FastDigest SaqAI: total reaction buffer is 10 μl
   2.1. Mix X μl of genomic amplified DNA (do not exceed 2 μg)+1 μl 10×FastDigest SaqAI
   Reaction Buffer+Sterile water up to 10 μl;
   2.2. Digest at 37° C. for 10 min;
   2.3. Check the extent of digestion, take 1.5 μl for the agarose gel;
   2.4. Purify product of digestion by using PureLink Quick PCR Purification Kit (Invitrogen, USA);
   2.5. Take DNA spectra to estimate yield.
3. 2nd Amplification: total reaction volume is 50 μl
   3.1. Mix X μl of fragmented genomic DNA+20 μl AlexaFluor®555 Panomer™9 solution+sterile water up to 44 μl and incubate at 95° C. for 10 min and immediately chill on ice for 5 min. The amount of genomic DNA per reaction can be varied from 500 to 2000 ng with the satisfactory results;
   3.2. Add 5 μl 10× Nucleotide Mix with Alexa Fluor® 555-aha-dCTP+1 μl Exo-Klenow Fragment;
   3.3. Incubate at 30° C. for 8 hours;
   3.4. Stop reaction by 5 μl Stop Solution;
   3.5. Check the amplification, take 5 μl for the agarose gel;
   3.6. Purify product of digestion by using PureLink Quick PCR Purification Kit (Invitrogen, USA);
   3.7. Take DNA spectra to estimate yield;
   3.8. Pellet of the purified DNA by adding 10 volumes of 2% $LiClO_4$ in acetone for at least 30 min at −20° C.;
   3.9. Collect DNA by centrifugation at 15,000 rpm for 20 min at 4° C.;

3.10. Wash the pellet once with 1 ml acetone and leave for drying on air.
4. Hybridization
  4.1. Dissolve the pellet in the hybridization buffer (1 M GuSCN (guanidine thyocianate), 5 mM EDTA, 50 mM HEPES (pH 7.5), 0.2 mg/ml BSA (bovine serum albumin), heat at 95° C. for 5 min and follow by immediate chilling on ice for 2 min.
  4.2. Hybridization at 25° C. for 4 hr;
  4.3. Washing 1 time in 4×SSC, 7.2% Sarcosyl for 30 sec; 1 time in 0.2×SSC for 30 sec shaking.

As outlined above, fragmentation can be performed using dsDNA Fragmentase or by FastDigest SaqAI. Additionally, steps of the target DNA preparation and hybridization are outlined in FIG. 5. All procedures were performed according to manufacturer instructions.

The developed protocol is presented schematically in FIG. 5. All procedures were performed according the manufacturer instructions. Illustra™ GenomiPhi HY DNA Amplification Kit was the most effective among the different tested amplification kits, as it amplified the initial DNA quantity (10-50 ng) 200-1000 times.

Fragmentase or restrictase SaqAI revealed less losses of DNA quantity after digestion in comparison with DNaseI. The labeling procedure by using ULYSIS® Alexa Fluor® 546 Nucleic Acid Labeling kit was substituted by BioPrime® Plus Array CGH Genomic Labelling System. The latter one was more effective because the labelling procedure is accompanied by the amplification. In addition, BioPrime® Plus Array CGH Genomic Labelling System kit contains not only Alexa Fluor® 555-aha-dCTP, but also random primers labelled at 5'-end with Alexa Fluor® 555.

The labelled target DNA was precipitated by 10 volumes of 2% $LiClO_4$ in acetone for 30 min at −20° C. The pellet was collected by centrifugation at 15,000 rpm for 30 min, washed 1 time with acetone and air dried. The pellet represents the labeled target DNA ready for hybridization on the biochip.

Various hybridization conditions (buffers, temperature, and time) were tested, and the optimized one was selected. The labeled target DNA was dissolved in hybridization buffer (1 M GuSCN, 5 mM EDTA, 50 mM HEPES (pH 7.5), 0.2 mg/ml BSA). The mixture was denatured at 95° C. for 5 min, and chilled on ice for 2 min. The sample was placed onto oligonucleotide probes array slides at 25° C. and covered with a glass cover slip. After hybridization for 4 hours at 25° C. in Arrayit hybridization chamber (Arrayit Corporation, USA), slides were rinsed with 2×SSC, 3.6% Sarcosyl (Sodium lauroyl sarcosinate) for 30 sec, afterwards, the slides were washed with 0.2×SSC at room temperature for 30 sec, spun-dry at 1000 rpm for 1 min before analyzing by the portable microarray reader PA5000 (Aurora Photonics, USA).

The most effective combination of DNA amplification, fragmentation and labeling procedures was generated and applied to environmental samples.

Example 5

Testing of a Biochip Prototype on the *Desulfobacterium autotropicum* DNA

The developed protocol for DNA amplification, fragmentation and labeling was next tested on *Desulfobacterium autotropicum*, DSM 3382. The results are shown in FIG. 6. A small array was constructed from 12 probes with duplicate of each probe. 8 probes were designed for detection of functional hydrogenases genes (Dv, Dbacterium1, Dbulbus, Dbacter1, Dbacter2, Dsmicrobium1, Dtomaculum 2, Dscoccus) to evaluate effects of SRB on corrosion scale. Three probes were designed to detect structural 16S rRNA genes, two of them (Dv 16S_1, Dbacterium 16S_2) specific to *Desulfovibrio* and *Desulfobacterium* according to literature [15] and one probe (16SCONS_1) was used for the discrimination of any bacteria in bacterial consortium (positive control). The probe SRB1 was used for the discrimination of any SRB in bacterial consortium [10].

Figure 6A:
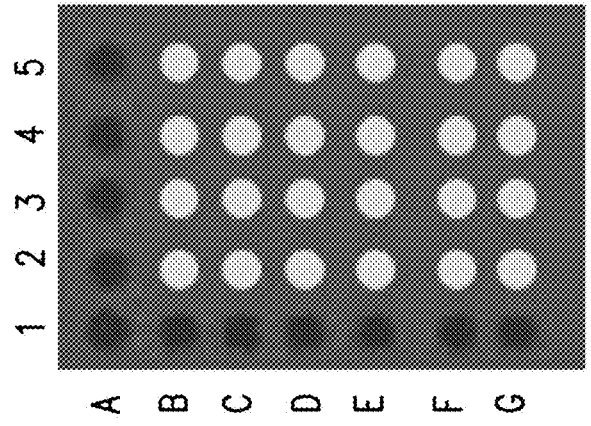
FIGS. 6A-C show amplification and hybridization results from *Desulfobacterium autotropicum* DNA reacted with one of the BioChip prototypes described herein.
Figure 6B:
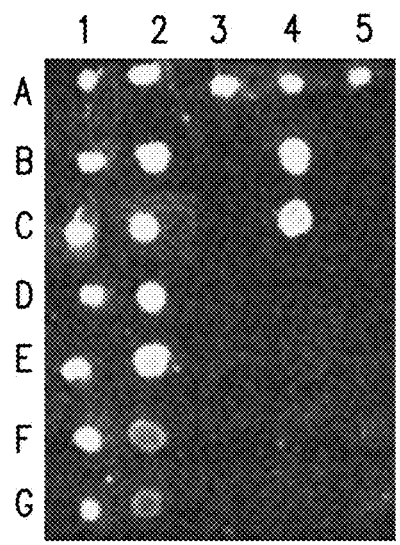
Figure 6C:
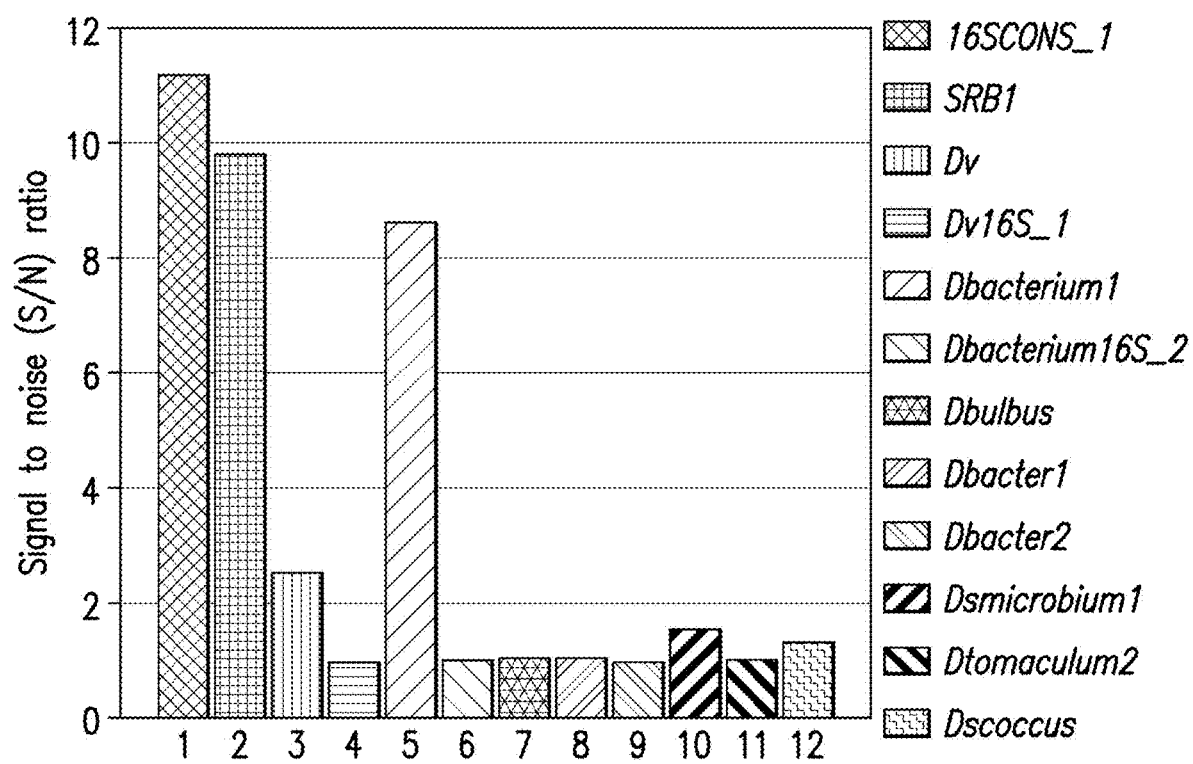

The arrangement of the probes on the biochip is shown in FIG. 6A. FIG. 6B represents the hybridization image, while FIG. 6C represents the hybridization signal intensities estimated as signal to noise (S/N) ratio. The signal from the probe 16SCONS_1 defines the presence of the bacteria. The signal from the probe SRB1 defines the presence of SRB. Two specific probes Dbacterium1 and Dbacterium 16S_2 have been selected to discriminate *Desulfobacterium* sp. Only the probe Dbacterium1 revealed the signal to noise ratio higher than 1. Thus, a positive reaction has occurred when the signal to noise ratio is higher than 1.

The probe Dv discriminates any *Desulfovibrio* in bacterial consortium on the basis of hynB (periplasmic Ni,Fe hydrogenase) gene. The similar structure is also present in the hynB (periplasmic Ni,Fe hydrogenase) gene of *Desulfobacterium*, where the difference is only one letter (SEQ ID NO:83: CAC CCC TGC ATC GGG TGC AG) in comparison with the Dv probe (SEQ ID NO:4: CAC CCC TGC ATC GG C TGC AG). It was found that the intensity of the fluorescent signal for this probe is significantly lower than that of the specific probe Dbacterium1 for *Desulfobacterium* sp.

Therefore, the *Desulfobacterium* sp. discrimination is accomplished by the probe Dbacterium1 on the biochip. The probes 16SCONS_1, SRB1, and Dbacterium1 revealed the similar fluorescent signal, as it has been observed when the probes have been tested by the cassette method.

The relevance of the cassette and extended ss DNA approaches for the selection of the probes with identical hybridization capacity for the inclusion in a biochip was confirmed on the bacterial DNA.

Example 6

Analysis of Environmental Samples Using Three Different MIC BioChip Prototypes

In order to develop a final pilot MIC BioChip (comprising probes listed in Table 5), the inventors used three DNA samples (A2, A21, and A13) and analyzed each using four different MIC BioChip prototypes. Different biochip prototypes provided an opportunity to analyze the efficiency of the selected probes as applied to environmental samples and to estimate the sufficient DNA quantity for the hybridization signal detection. The developed N10 protocol for DNA amplification, fragmentation and labeling described in Example 4 was used for the preparation of all DNA samples for hybridization.

Figure 7A:
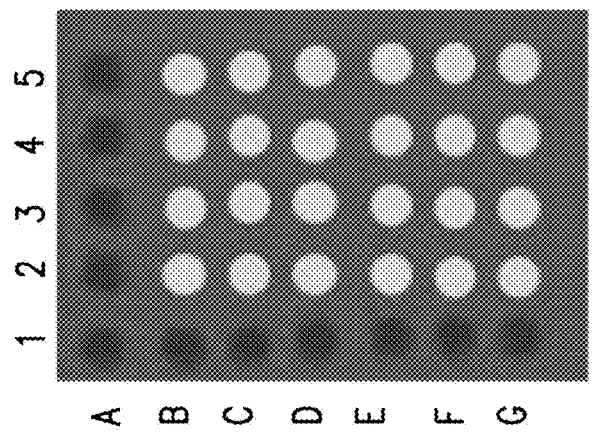
FIGS. 7A-C are results from DNA sample A2 that was amplified and hybridized with a prototype biochip.
Figure 7B:
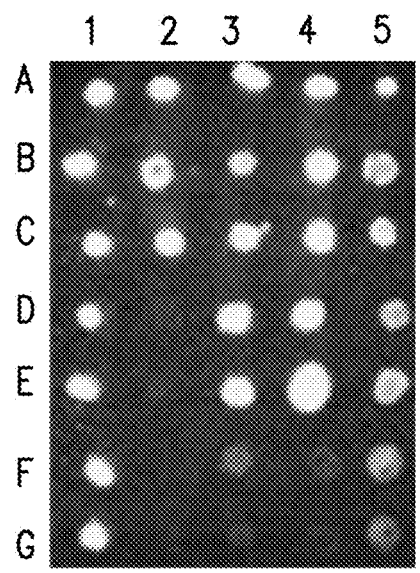

The biochip prototype for A2 sample analysis was constructed from 12 probes in duplicate. 11 probes were used for the detection of SRB and their 7 genera in the bacterial consortium (SRB1, DSR2, Dv, Dbacterium1, Dbulbus, Dbacter2, Dbacter1, Dsmicrobium1, Dtomaculum2, Dtomaculum1, and Dscoccus1) and one probe 16SCONS_1 served as a positive control probe. The results are presented in FIG. 7.

The probes SRB1 and DSR2 were chosen for detection of any SRB in bacterial consortium. The probe SRB1 was highly effective by applying it to the environmental sample A2. Among the 7 genera of SRB, 6 genera *Desulfovibrio* sp.,

*Desulfobulbus* sp., *Desulfobacterium* sp., *Desulfomicrobium* sp., *Desulfotomaculum* sp., *Desolfococcus* sp. were detected. The highest hybridization signals were observed for *Desulfovibrio* sp., *Desulfobulbus* sp., and *Desulfobacterium* sp.; followed by *Desulfomicrobium* sp., *Desulfotomaculum* sp., *Desolfococcus* sp. These observations indicate that *Desulfovibrio* sp. and *Desulfobulbus* sp. dominate in the SRB consortium of the sample A2. *Desulfobacter* sp. were not detected by applying the biochip to the sample A2.

Figure 8A:
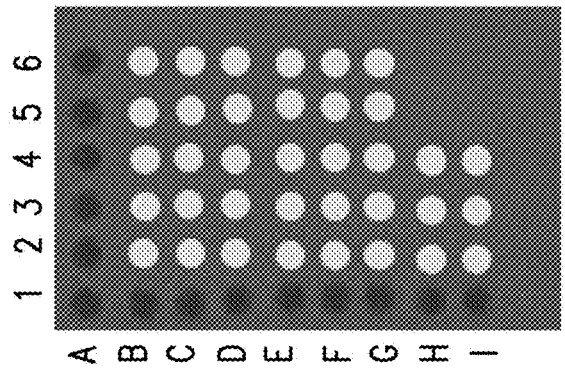
FIGS. 8A-C are results showing probe designs and hybridization results from amplified DNA of A21 sample. The A21 sample was amplified and hybridized with one of the prototype biochips.
Figure 8B:
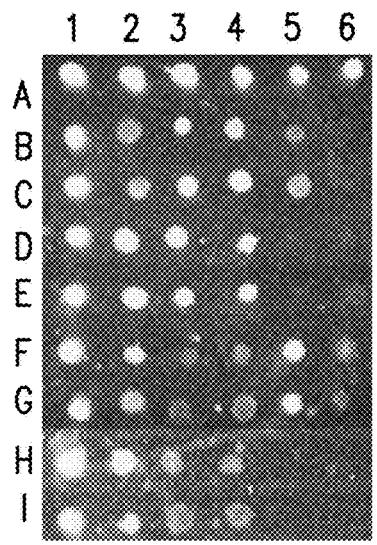
Figure 8C:
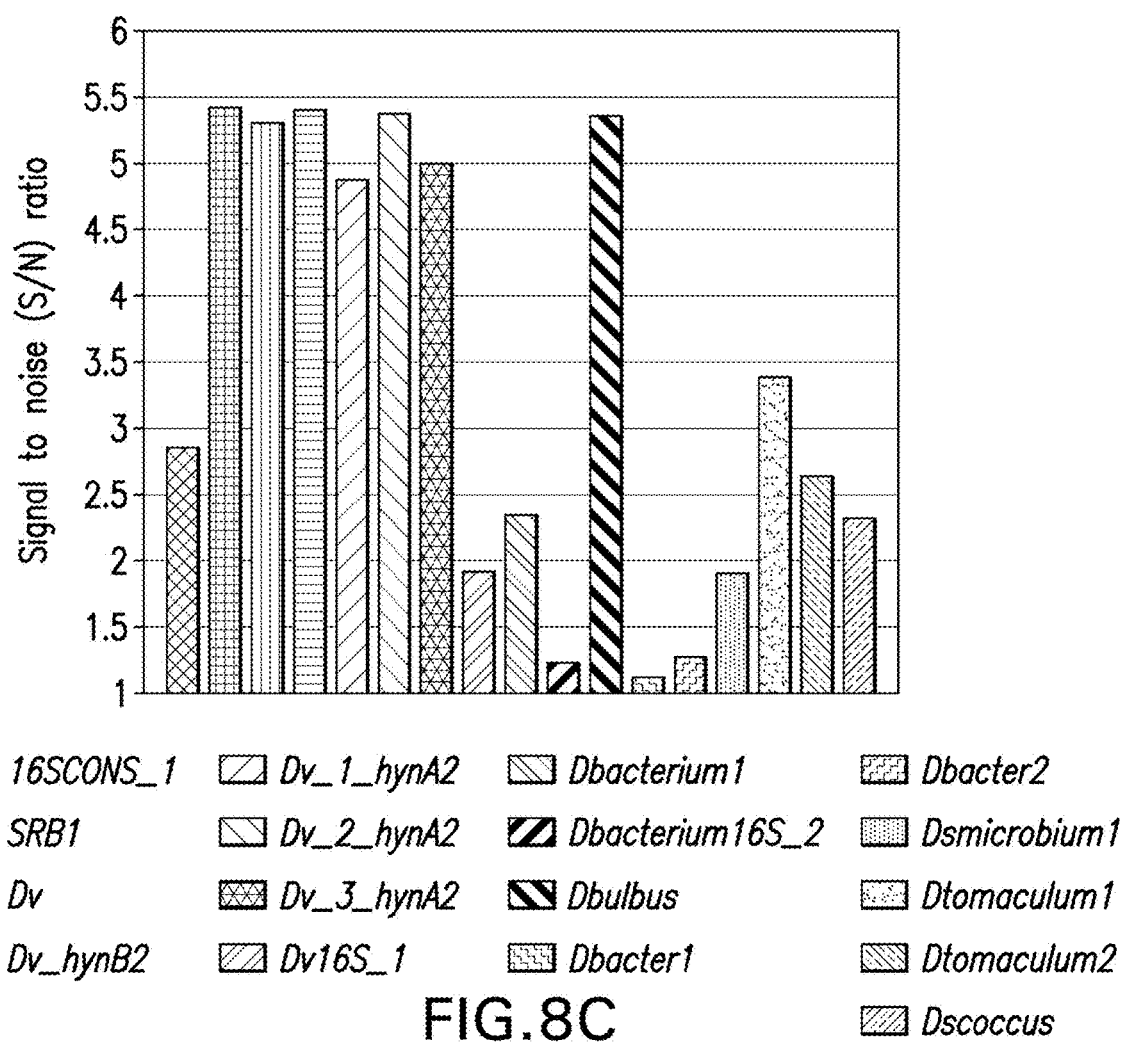

The MIC biochip prototype for A21 sample analysis was constructed using 17 probes in duplicate. 16 probes (SRB1, Dv, Dv_hynB2, Dv 1 hynA2, Dv_2_hynA2, Dv_3_hynA2, Dv16S_1, Dbacterium1, Dbacterium_16S_2, Dbulbus, Dbacter2, Dbacter1, Dsmicrobium1, Dtomaculum2, Dtomaculum1, and Dscoccus1) were used for the detection of SRB and one probe (16SCONS_1) was used as a positive control probe. The results are presented in FIG. 8. Five probes for the hydrogenase gene (Dv, Dv_hynB2, Dv_1_hynA2, Dv_2_hynA2, and Dv_3_hynA2) were tested for the specification of *Desulfovibrio* sp. as the leading genus in MIC development. All probes for the hydrogenase gene revealed the same hybridization signal. This strongly confirms the presence of *Desulfovibrio* sp. in the sample A21.

Among the 7 genera of SRB, 6 genus of SRB were present in the A21 sample. The highest hybridization signals were observed for *Desulfovibrio* sp. and *Desulfobulbus* sp., followed by *Desulfotomaculum* sp., and *Desolfococcus* sp., and then by *Desulfobacterium* sp., and *Desulfomicrobium* sp. *Desulfobacter* sp. were not detected by applying the biochip prototype to the environmental sample A21.

In conclusion, the inventors observed that profiles of SRB in sample A2 and A21 are different. *Desulfovibrio* sp., *Desulfobulbus* sp., and *Desulfobacterium* sp., dominate in sample A2, while *Desulfovibrio* sp. and *Desulfobulbus* sp. dominate in sample A21. 2.5 µg of total DNA was sufficient for the visualization of the biochip results.

Another MIC biochip prototype for A13 sample analysis was constructed from 16 probes in duplicate. This prototype includes the probes for the detection of two types of bacteria: SRB and NRB. NRB can weaken the biocorrosion process caused by SRB. 11 probes (SRB1, Dv, Dv16S_1, Dbacterium1, Dbacterium_16S_2, Dbulbus, Dbacter2, Dbacter1, Dsmicrobium1, Dtomaculum 2, and Dscoccus1) were used for the detection of SRB, while 4 probes (narG, napA, nirS, nirK) were used for the detection of NRB. One probe 16SCONS_1 served as a positive control probe.

Figure 9A:
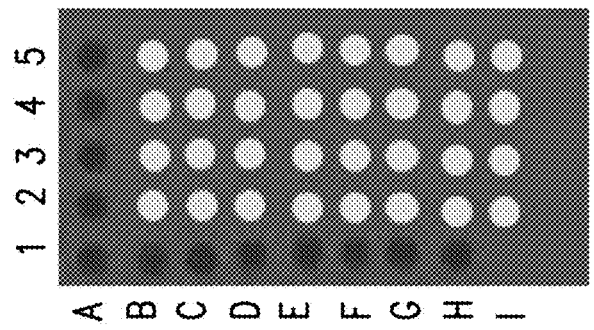
FIGS. 9A-C are results showing probe designs and hybridization results from amplified DNA of A13 sample. MIC biochip prototype for A13 sample analysis was constructed from 16 probes in duplicate. This prototype includes the probes for the detection of two types of bacteria: SRB and NRB. 11 probes (SRB1, Dv, Dv16S_1, Dbacterium1, Dbacterium_16S_2, Dbulbus, Dbacter2, Dbacter1, Dsmicrobium1, Dtomaculum 2, and Dscoccus1) were used for the detection of SRB, while 4 probes (narG, napA, nirS, nirK) were used for the detection of NRB. One probe 16SCONS_1 served as a positive control probe.
Figure 9B:
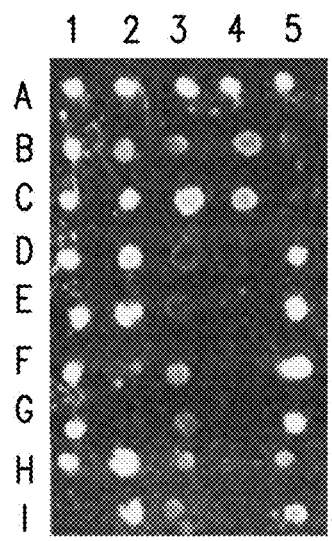
Figure 9C:
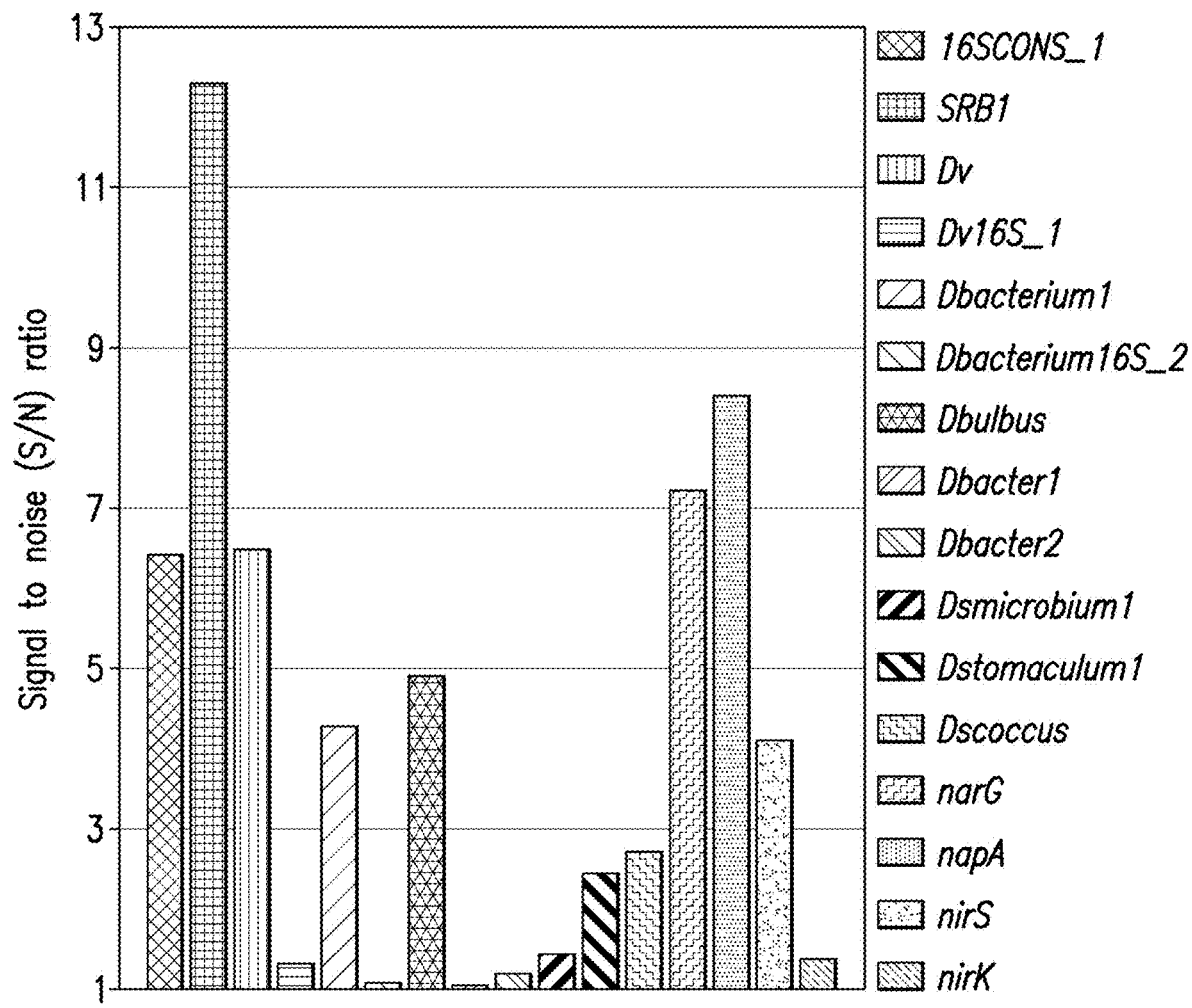

The results are shown in FIG. 9A-C. These results indicate that along the SRB, NRB are detected as well. Both groups of bacteria reveal comparable fluorescent signals. The profiles of SRB in samples A2 and A13 were similar. *Desulfovibrio* sp., *Desulfobulbus* sp., and *Desulfobacterium* sp. dominated, followed by *Desulfotomaculum* sp., *Desolfococcus* sp., *Desulfomicrobium* sp. *Desulfobacter* sp. were not detected by applying the BioChip to samples A2, A21 nor A13.

Figure 10A:
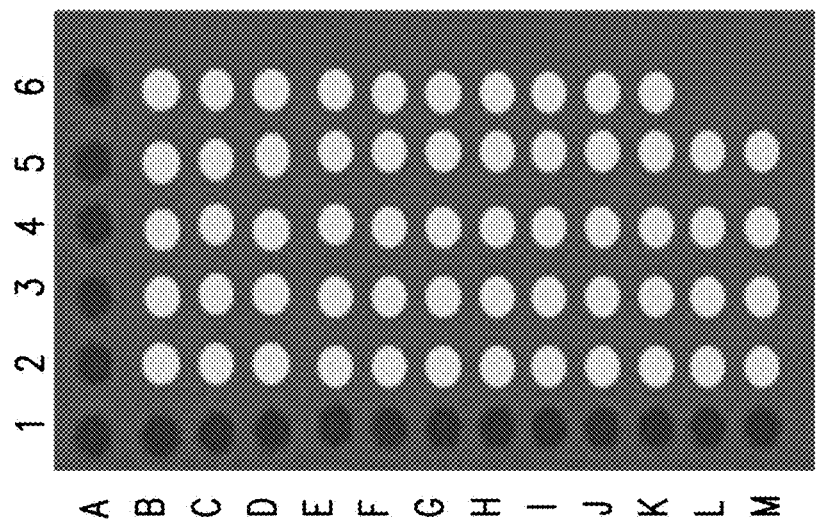
FIGS. 10A-C are results from DNA of sample A2 that was amplified and hybridized with the pilot biochip.
Figure 10B:
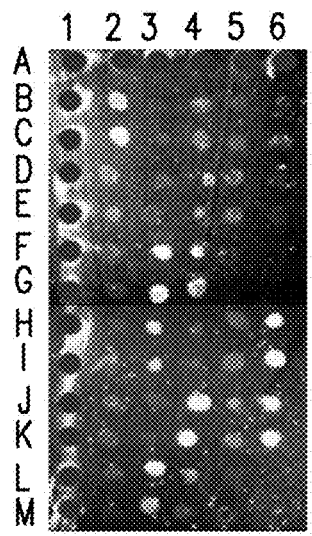
Figure 10C:
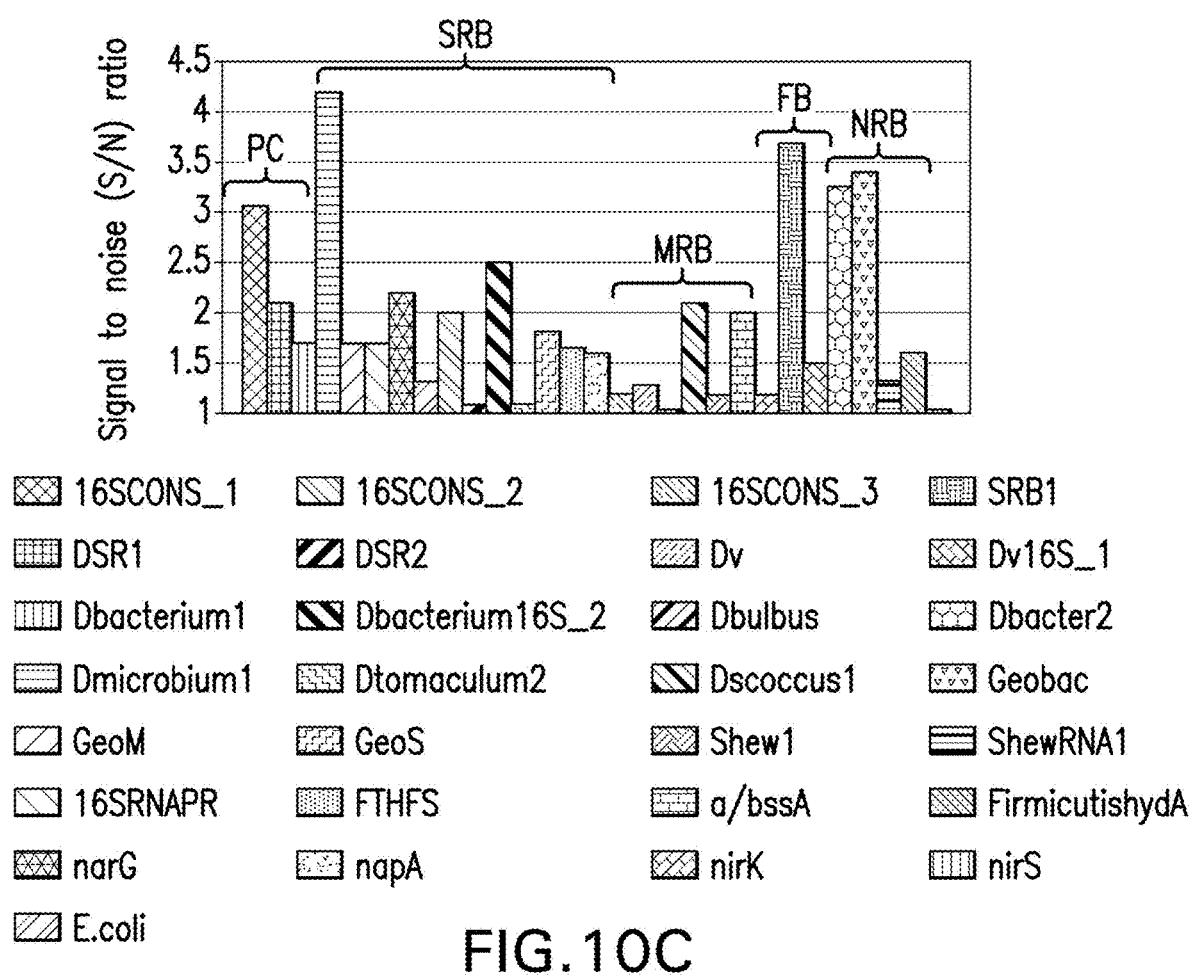

Yet another MIC BioChip prototype, containing 29 probes in duplicate for the identification of key bacterial groups involved in biocorrosion, was next used for the analysis of the A2 sample. The results are shown in FIG. 10. The arrangement of the probes is presented in FIG. 10A; the hybridization image is presented in FIG. 10B; and the distribution of the hybridization signals among the probes is presented in FIG. 10C.

12 probes (SRB1, DSR1, DSR2, Dv, Dv 16S_1, Dbacterium1, Dbacterium 16S_2, Dbulbus, Dbacter2, Dsmicrobium1, Dtomaculum 2, and Dscoccus1) were used for the detection of SRB and their 7 genera in the bacterial consortium. 6 probes (Geobac, GeoM, GeoS, Shew1, ShewRNA1, 16SRNAPR) were used for detection of MRB in the bacterial consortium. Three probes (FTHFS, a/bssA, FirmicytishydA) were used for identification of FB in the bacterial consortium. Four probes (narG, napA, nirS, nirK) were used for detection of NRB in the bacterial consortium. Three probes (16SCONS_1, 16SCONS_2, 16SCONS_3) were included for the discrimination of any bacteria in bacterial consortium (PC—positive controls).

Figure 7C:
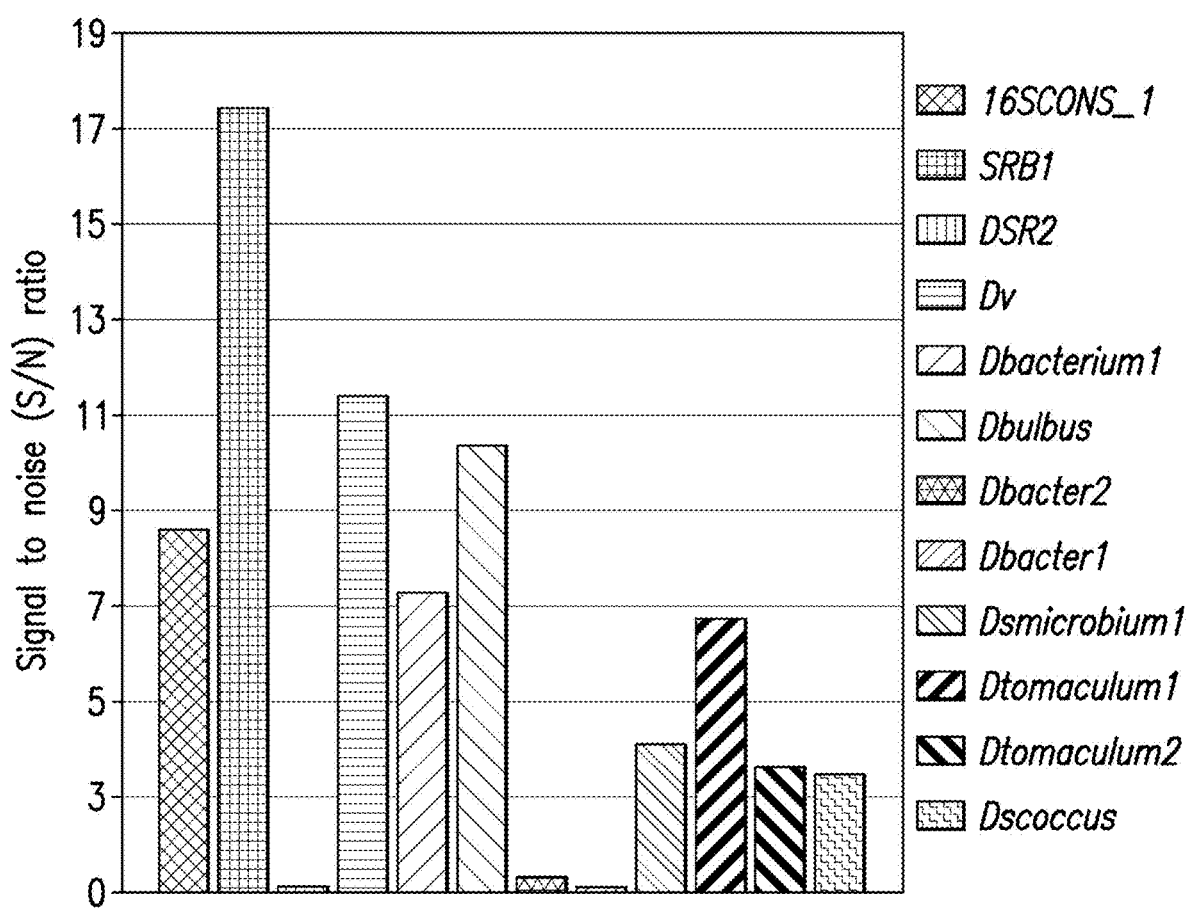

Analysis of the A2 sample using the 29 probe BioChip revealed the same profile of hybridization signals for SRB on both biochip prototypes (FIG. 10C, 7C). The intensities of the hybridization signals were higher on a smaller 12-probe biochip prototype (FIG. 10C), since the concentration of DNA and fluorophore was higher. 5.5 µg DNA was dissolved in 7 µl of hybridization buffer (in the instance of the 12-probe biochip prototype) vs. 6.5 µg DNA dissolved in 24 µl of hybridization buffer to cover the smaller surface are of the biochip (in the instance of the 29-probe biochip prototype).

Among the MRB group, *Shewanella* sp. were detected, while *Geobacter* sp. were not. Hydrocarbon degrading bacteria were identified in the FB group. NRB were detected based on the nitrate and nitrite reductase gene probes. Finally, A2 sample did not contain detectable *E. coli*.

The analysis of the environmental samples by the various biochip prototypes revealed that fluorescent signals are absent for some probes. This could either indicate the absence of the appropriate group of bacteria in the studied consortium (sample), or that the probe is not suitable for bacterial detection on a specific biochip.

The functional probe Dbacterium1 and structural probe Dbacterium 16S_2 have been selected for discrimination of *Desulfobacterium* sp. While de novo designed probe Dbacterium1 revealed the signal, the probe Dbacterium 16S_2, selected from the literature [15] did not provide the signal in any of the studied cases, including *Desulfobacterium autotropicum* DNA. The absence of signal thus indicates that Dbacterium 16S_2 probe is not suitable for the bacterial detection. Accordingly Dbacterium 16S_2 probe was not included in the pilot biochip.

Three probes SRB1, DSR1, and DSR2 were included in one of the prototype MIC-BioChip for the detection of any SRB in the consortium. The analysis of the environmental samples indicated that only probe SRB1 is highly effective, while the signals from the probes DSR1, and DSR2 were barely detectable. Both these probes were selected from the literature [11]. However, in all studied cases, including *Desulfobacterium autotropicum* DNA, probe SRB1 (based on apr gene) provided a strong signal. It is known that dsr gene is not sufficiently conservative. As the weak signal implies that these probes are not suitable for the bacteria detection, DSR1 and DSR2 were not included in the pilot MIC BioChip. While all three positive control probes (16SCONS_1, 16SCONS_2, 16SCONS_3) revealed detectable signal, the inventors included just one positive probe 16SCONS_1 in the pilot MIC BioChip, since it was the most effective in all studied cases.

Figure 4A:
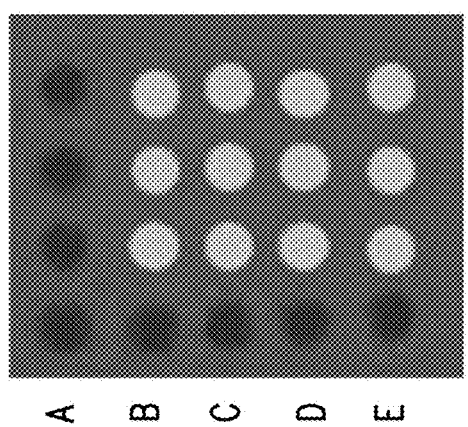
FIGS. 4A-H are schematic diagrams and hybridization analyses of six different SRB genes with the activated BioChip.
Figure 4B:
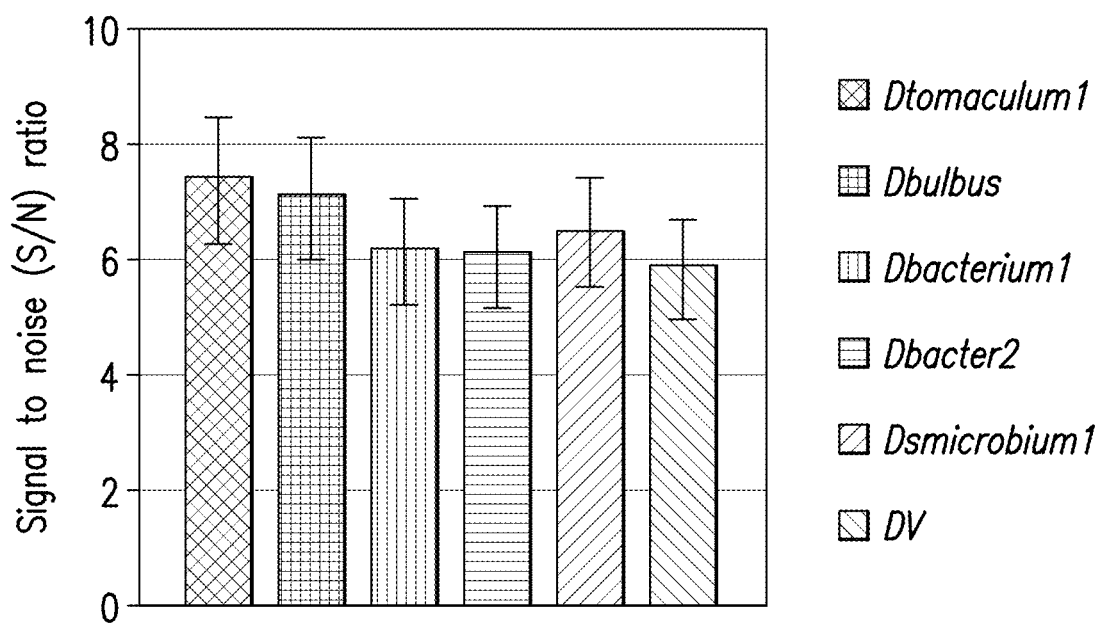
Figure 4C:
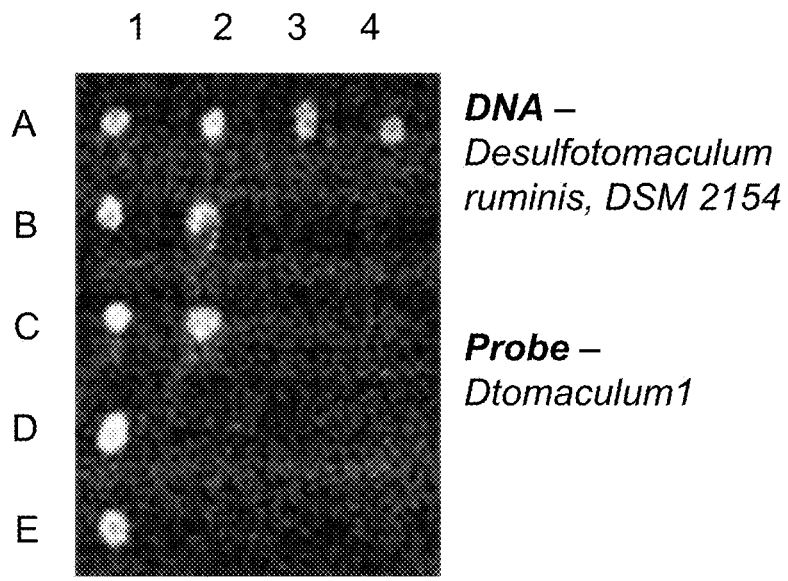
Figure 4D:
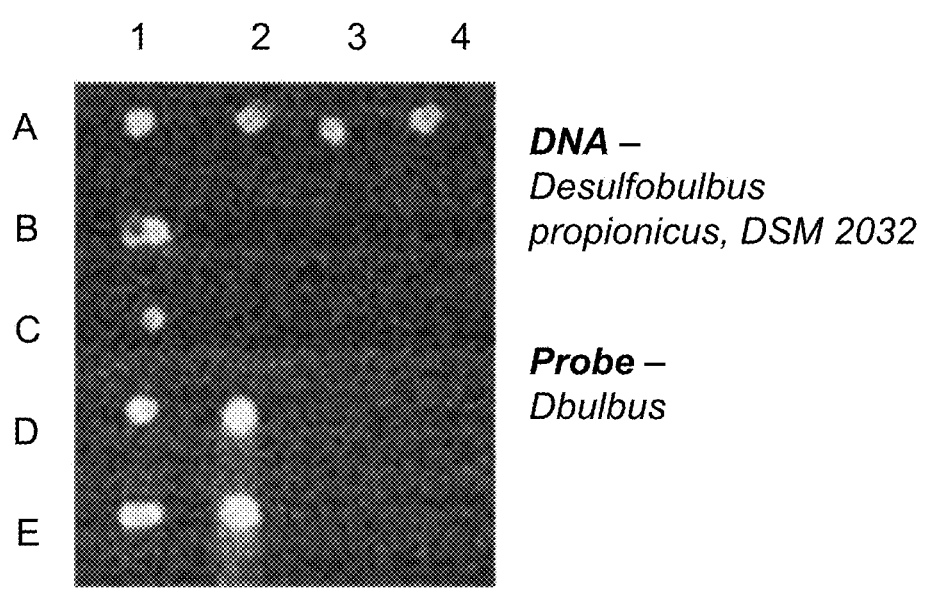
Figure 4E:
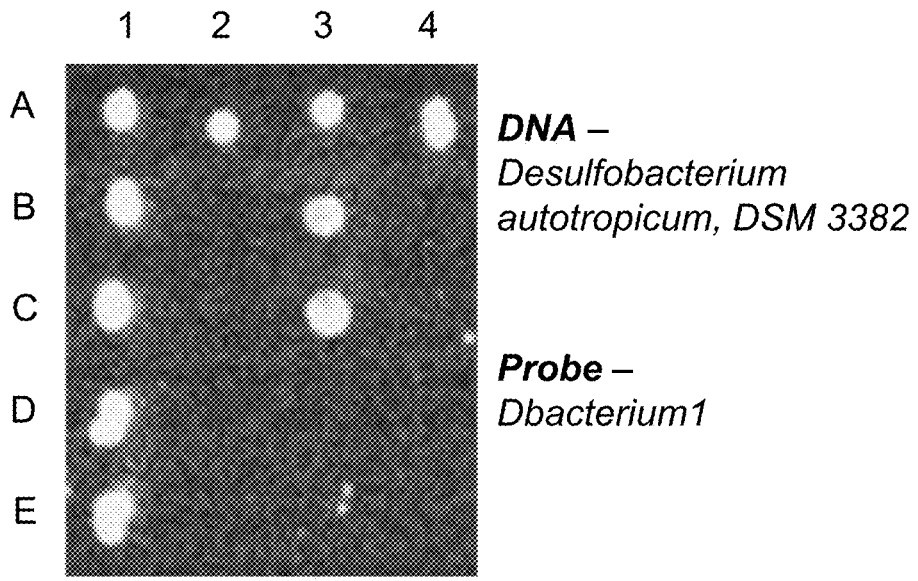
Figure 4F:
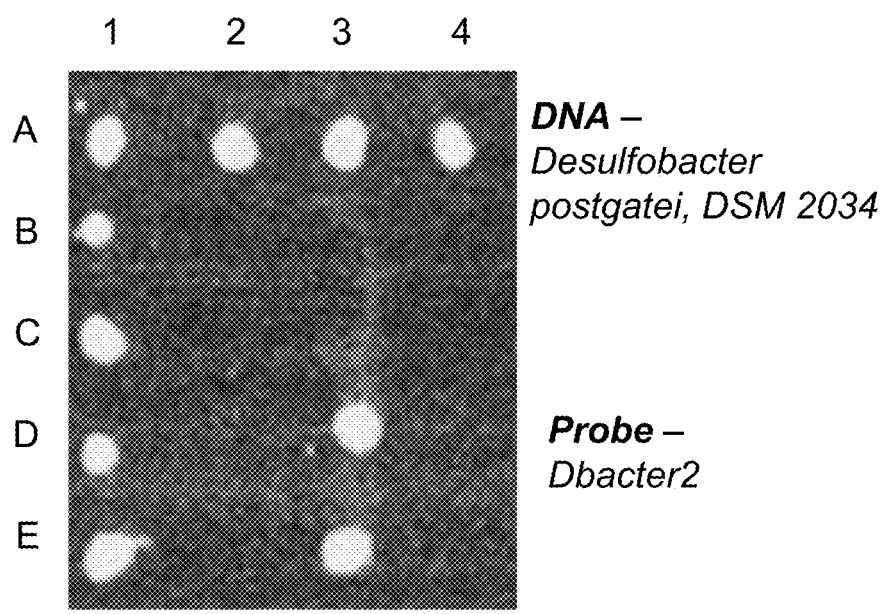
Figure 4G:
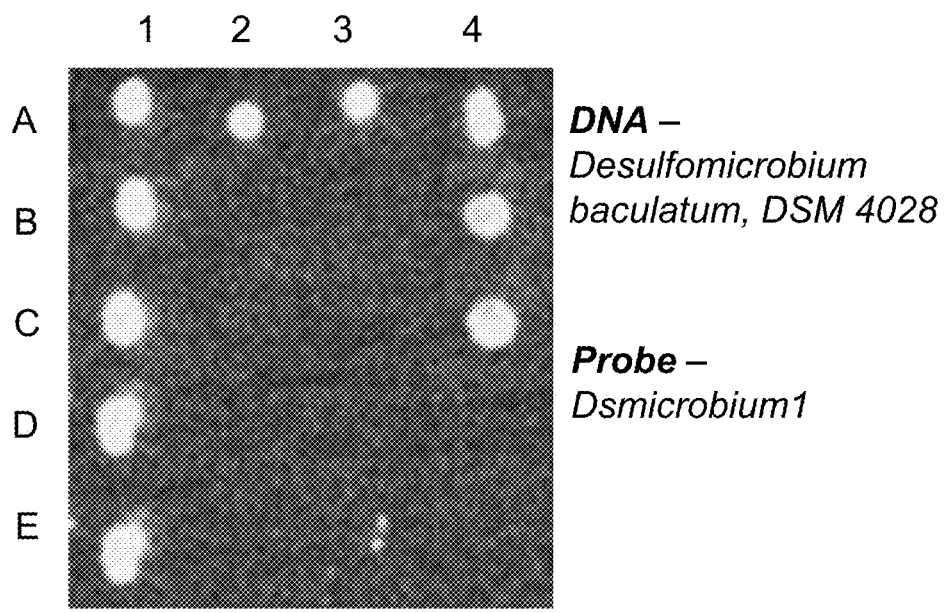
Figure 4H:
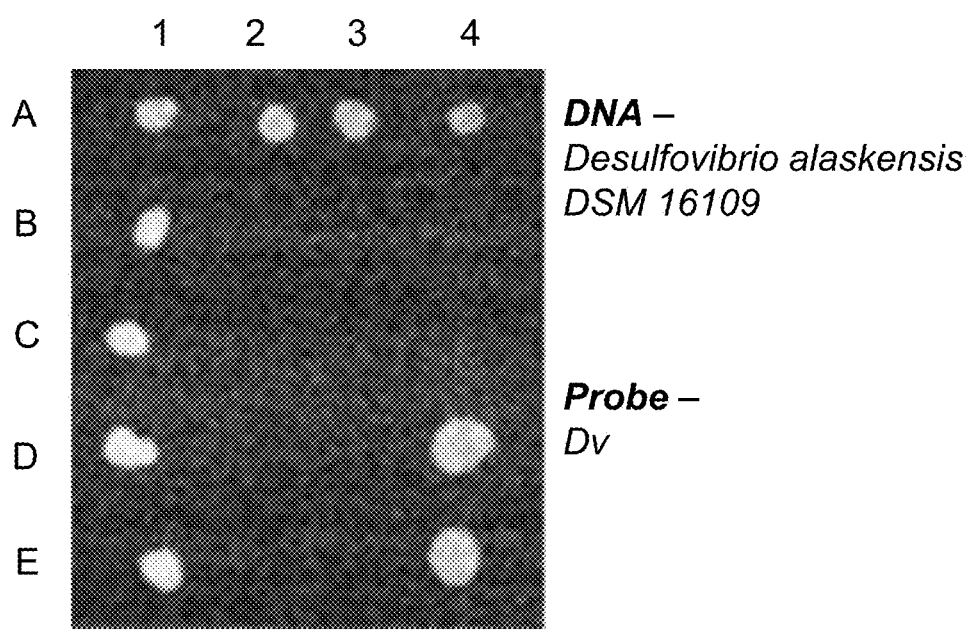

Dbacter1 and Dbacter2 functional probes were selected for detection of *Desulfobacter* sp. Neither of the two probes revealed signal using the environmental samples, however, the probe Dbacter2 worked well on *Desulfobacter* strain (FIG. 4F). This result is most likely due to the absence of *Desulfobacter* sp. in the studied cases. Thus, both Dbacter1 and Dbacter2 probes were included in the pilot biochip.

The experiments described herein allowed the inventors to develop a pilot MIC BioChip comprising 30 probes listed in Table 5. Among the 30 probes, 11 probes permit identification of the main SRB groups involved in the biocorrosion and provides a corrosion scale, 18 probes allow identification of additional MIC bacterial groups (Archea, MRB, FB, NRB, *E. coli*), one positive control probe (16SCONS_1).

TABLE 5

38 initial oligonucleotide probes selected on the basis of the key genes of metabolic pathways involved in MIC.

| | Group | Targeted organism | Targeted geme | Probe name | Sequence 5'-3' | References |
|---|---|---|---|---|---|---|
| 1 | Archaea | SRB | APR-reductase | SRB1 | CCA GGG CCT GTC CGC CAT CAATAC (SEQ ID NO: 1) | Zinkevich V., et al., FEMS Microbiol Ecol (2000) 34:147-155 |
| 2 | | *Desulfobvibrio* | hynB (periplasmic Ni,Fe hydrogenase) | Dv | CAC CCC TGC ATC GGC TGC AG (SEQ ID NO: 4) | de novo |
| 3 | | *Desulfobacterium* | hynB (periplasmic Ni, Fe hydrogenase) | Dbacterium1 | CAC TGG AAC AG CGA TCA AG (SEQ ID NO: 5) | de novo |
| 4 | | *Desulfobulbus* | hydA (Ni, Fe-hydrogenase) | Dbulbus | GCG CCA CCC TGC CGT TCA AC (SEQ ID NO: 6) | de novo |
| 5 | | *Desolfobacter* | hydA (Ni, Fe-hydrogenase) | Dbacter2 | TCA CCT GGT GAA AAT CGG ACT (SEQ ID NO: 7) | de novo |
| 6 | | *Desulfobacter* | hydA (Fe-hydrogenase) | Dbacter1 | CTG GAT CGT CCT TTC GAT CGT (SEQ ID NO: 84) | de novo |
| 7 | | *Desulfomicrobium* | hydA (Ni, Fe-hydrogenase) | Dsmicrobium1 | CCA CAA CCT GGC CAT CCC GGA AAT (SEQ ID NO: 8) | de novo |
| 8 | | *Desulfotomcaculum ruminis* | hydA (Fe-hydrogenase) | Dtomaculum1 | ACC TAT GCC GAT TGT CCC CG (SEQ ID NO: 80) | de novo |
| 9 | | *Desulfotomaculum* | hydA (Fe-hydrogenase) | Dtomaculum2 | CAC GCA TCG GGG AGA GGG TGG (SEQ ID NO: 9) | de novo |
| 10 | | *Desulfococcus* | hydB gene of hydrogenase accessory protein HypB | Dscoccus | CAC CTC CTC CAA AAC CGG GGA AGG (SEQ ID NO: 10) | de novo |
| 11 | | *Desulfobibrio* | 16S rRNA gene for *Desulfovibrio* spp. (including *Dv. vulgaris*, *Dv. desuluricans*) | Dv 16S_1 | CAA TCC GGA CTG GGA CGG (SEQ ID NO: 11) | Loy A., et al., Appl Environ Microbial (2002)68:5064-5081 |
| 12 | | *Methanogenic Archaea* | Methyl coenzyme M reductase (mcr) | MCR1 | CCA GGT GC ATC AAG TTC GGA CAC (SEQ ID NO: 13) | de novo |
| 13 | | Archaea | 16S rRNA gene | Archaea1 | GTG CTC CCC CGC CAA TTC AT (SEQ ID NO: 14) | Loy A., et al., Appl Environ Microbial (2002)68:5064-5081 |
| 14 | | Archaea | 16S rRNA gene | Archaea2 | TGT TGA CTA CGT GTT ACT GAG (SEQ ID NO: 15) | Loy A., et al., Appl Environ Microbial (2002)68:5064-5081 |
| 15 | | Archaea | 16S rRNA gene | ARC16SRNA | AGG AAT TGG CGG GGG AGC AC (SEQ ID NO: 16) | Raskin L., et al. Applied and Environmental Microbiology (1994) |
| 16 | MRB (Metal-Reducing Bacteria) | *Geobacter* spp | hydA (Ni, Fe-hydrogenase) | Geobac | CAC CCG GTGCAC TCC TGG A (SEQ ID NO: 17) | de novo |

TABLE 5-continued 38 initial oligonucleotide probes selected on the basis of the key genes of metabolic pathways involved in MIC.

| | Group | Targeted organism | Targeted geme | Probe name | Sequence 5'-3' | References |
|---|---|---|---|---|---|---|
| 17 | | Shewanella spp | hydA (Ni, Fe-hydrogenase) | Shew | ACA ACT GCC CAA CCG AGC GC (SEQ ID NO: 18) | de novo |
| 18 | | G. sulfurreducens | 16S rRNA gene | GeoS | TTC GGG CCT CCT GTC TTT C (SEQ ID NO: 20) | de novo |
| 19 | | G. metallireducens | 16S rRNA gene | GeoM | TTC GGG CCT TTT GTC ACC (SEQ ID NO: 21) | de novo |
| 20 | | Shewanella spp | 16S rRNA gene | ShewRNA1 | CGC GAT TGG ATG AAC CTA G (SEEQ ID NO: 22) | de novo |
| 21 | | Arthrobacter spp | 16S rRNA gene | 16SRNA PR | GTC TGC CGT GAA AGT CCG (SEQ ID NO: 24) | de novo |
| 22 | FB (Fermentative bacteria) | Acetogenic | formyltetrahydrofolate synthetase (fthfs) | FTHFS | TGC ATG GCC AAG ACC CAA TAC AGC (SEQ ID NO: 25) | Salmassi TM., et al. Microbiology (2003) 149:2529-2537 |
| 23 | | Hydrocarbon-degrading | alkylsuccinate synthase and benzylsuccinate synthase alpha subunits (assA/bssA) | a/bssA | TCG TCA TTG CCC CAT TTG GGG GC (SEQ ID NO: 26) | Callaghan AV., et al. Environ Sci and Technol (2010) 44: 7287-7294 |
| 24 | | Firmicutes | hydA (Fe-hydrogenase) | FirmicutishydA | AGG CGG CGA GCA TGA TCC AGC AAT (SEQ ID NO: 27) | de novo |
| 25 | | E.coli | hyaA | E.coli | ACT CCT GCG CGC CAA TCC AG (SEQ ID NO: 28) | de novo |
| 25 | NRB (Nitrate Reducing Bacteria) | NRB (Nitrate Reducing | nitrite reductase (nirS) | nirS | CGC TGT TCG TCA AGA CCC ATC CG (SEQ ID NO: 29) | de novo |
| 27 | | NRB (Nitrate Reducing | nitrite reductase (nirK) | nirK | CCC GAC CCA CGT CGT ATT CAA CGG (SEQ ID NO: 30) | de novo |
| 28 | | NRB (Nitrate Reducing | nitrite reductase (narG) | narG | CCA GCT TCT TCT ACG CCC ACA CCG (SEQ ID NO: 31) | de novo |
| 29 | | NRB (Nitrate Reducing | nitrite reductase (napA) | napA | CCG CGG CTA TGT GGG TCG AAA AAG (SEQ ID NO: 32) | de novo |
| 36 | Bacteria | Bacteria | 16S rRNA gene | 16SCONS_1 | CCT ACG GGA GGC AGC AG (SEQ ID NO: 36) | Muyzer G., et al., Appl and Environ Micobiol. (1993) 59:695-700 |

EQUIVALENTS

The invention can be embodied in other specific forms without departing from the spirit or essential characteristics thereof. The foregoing embodiments are to be considered in all respects illustrative rather than limiting on the invention described herein. In the various embodiments of the methods and systems of the present invention, where the term comprises is used with respect to the recited steps or components, it is also contemplated that the methods and systems consist essentially of, or consist of, the recited steps or components. Further, it should be understood that the order of steps or order for performing certain actions is immaterial so long as the invention remains operable. Moreover, two or more steps or actions can be conducted simultaneously. All percentages and ratios used herein, unless otherwise indicated, are by weight.

In the specification, the singular forms also include the plural forms, unless the context clearly dictates otherwise. Unless defined otherwise, all technical and scientific terms used herein have the same meaning as commonly understood by one of ordinary skill in the art to which this invention belongs. In the case of conflict, the present specification will control.

REFERENCES

1. He Zh., et al. GeoChip: a comprehensive microarray for investigating biogeochemical, ecological and environmental processes. *The ISME Journal* (2007) 1:67-77
2. Bodrossy L., et al. development and validation of a diagnostic microbial microarray for methanotrophs. *Environ Microbiol* (2003) 5:566-582
3. Tiquia S M., et al. Evaluation of 50-mer oligonucleotide arrays for detecting microbial populations in environmental samples. *Biotechniques* (2004) 36: 664-675
4. Wu L, et al. Microarray-Based Analysis of subnanogram quantities of microbial community DNAs by using whole-community genome amplification. *Applied and Environmental Microbiology* (2006) 72:4931-4941
5. Schatz M C., et al. Integrated microbial survey analysis of prokaryotic communities for the PhyloChip microarray. *Applied and Environ Microbiology* (2010) 76: 5636-5638
6. Abusam A., et al. (2002). Calibration and validation of a model for competition between methanogens and sulfate-reducers. In *Latin American Workshop and Symposium on Anaerobic Digestion*, 7 (p. 8). UNAM. Available from: http://www.bvsde.paho.org/bvsacd/unam7/calibration.df
7. Larsen J., et al. Consortia of MIC bacteria and archaea causing pitting corrosion in top side oil production facilities. *CORROSION* 2010, Mar. 14-18, 2010, San Antonio, Tex., Conference Paper N 10252. Available from: http://www.onepetro.org/mslib/servlet/onepetropreview?id=NACE-10252
8. Wolicka D., and Borkowski A. Microorganisms and Crude Oil. In: Introduction to Enhanced Oil Recovery (EOR) Processes and Bioremediation of Oil-Contaminated Sites. Dr. Laura Romero-Zerón (Ed.), ISBN: 978-953-51-0629-6, (2012) InTech, Available from: http://cdn.intechopen.com/pdfs/37040/InTech-Microorganisms_and_crude_oil.pdf
9. He Q., et al. Energetic consequences of nitrite stress in *Desulfovibrio vulgaris* Hildenborough, inferred from global transcriptional analysis. *Applied and Environ Microbiology* (2006) 72:4370-4381
10. Zinkevich V., Beech I B. Screening of sulfate-reducing bacteria in colonoscopy samples from healthy and colitic human gut mucosa. *FEMS Microbiology Ecology* (2000) 34:147-155
11. Klein M., et al. Multiple Lateral transfers of dissimilatory sulfite reductase genes between major lineages of sulfate-reducing prokaryotes. *Journal of Bacteriology* (2001) 183: 6028-6035
12. Vignaus P. M., Billoud B. Occurrence, classification, and biological function of hydrogenases: an overview. *Chem. Rev.* (2007) 107: 4206-4272
13. Li X., et al. Metabolism of $H_2$ by *Desulfovibrio alaskensis* G20 during syntrophic growth on lactate. *Microbiology* (2011) 157:2912-2921
14. Marshall I P G., et al. The hydrogenase chip: a tiling oligonucleotide DNA microarray technique for characterizing hydrogen-producing and—consuming microbes in microbial community. *The ISME Journal* (2012) 6:814-826
15. Loy A., et al., Oligonucleotide microarray for 16S rRNA gene-based detection of all recognized lineages of sulfate-reducing prokaryotes. *Appl Environ Microbiol* (2002) 68:5064-5081
16. Raskin L., et al. Group-specific 16S rRNA hybridization probes to describe natural communities of methanogens. *Applied and Environmental Microbiology* (1994) 60:1232-1240
17. Bavykin S. G., et al. Portable system for microbial sample preparation and oligonucleotide microarray analysis. *Applied and Environmental Microbiology* (2001) 67:922-928
18. D. A. Tomalia. Birth of a New Macromolecular Architecture: Dendrimers as quantized Building Blocks for Nanoscale Synthetic Organic Chemistry. *Aldrichimica Acta* (2004) 37, N2. Available from: http://www.sigmaaldrich.com/ifb/acta/v37/acta-vol37-2004.html#46
19. Lee, C. Cameron et al. Designing Dendrimers for Biological Application. *Nature Biotechnology* (2005) 23:1517-1526.
20. Balzani, Vincenzo. Dendrimers: order, complexity, functions. *Australian Journal of Chemistry* (2011) 64:129-130.
21. Breslauer K J, et al. Predicting DNA duplex stability from the base sequence. *Proc Natl Acad Sci USA* (1986) 83:3746-3750
22. Hager J. (2006) Making and using spotted DNA microarrays in an academic core laboratory. Methods Enzymol 410:135-168. doi: 10.1016/S0076-6879(06)10007-5.
23. Zinkevich V., Sapojnikova N., Mitchell J., Kartvelishvili T., Asatiani N., Alkhalil S., Bogdarina I., Al-Humam A. A novel cassette method for probe evaluation in the designed biochips. *PLOS ONE* (2014) 9: e98596. doi: 10.1371/journal.pone.0098596
24. Zhou and Thompson, *Advances in Agronomy*, Volume 82, 2004.

INCORPORATION BY REFERENCE

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims. The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

What is claimed is:

1. An oligonucleotide probe set suitable for detection, identification, or quantification of corrosion causing bacteria in a sample, comprising a plurality of probes, wherein the plurality of probes comprises at least one of SEQ ID NOs. 4-10, wherein all the probes of the probe set are immobilized at identifiable locations on a biochip.

2. The probe set of claim 1, further comprising a positive control probe of SEQ ID NO: 36.

3. A BioChip comprising oligonucleotide probes of SEQ ID NOs. 4 and 5, immobilized on a solid support, for detecting bacteria associated with microbially influenced corrosion.

4. The BioChip of claim 3, wherein the solid support comprises a 3D-matrix material.

5. The BioChip of claim 3, wherein the 3D-matrix material is dendrimer.

6. A kit suitable for performing an assay that detects, identifies and/or quantitates corrosion causing bacteria in a sample, wherein said kit comprises: a) the probe set of claim 1, wherein all the probes of the probe set are immobilized at identifiable locations on a biochip and optionally, b) additional reagents or compositions necessary to perform the assay.

7. The kit of claim 6, wherein the corrosion causing bacteria are selected from the group consisting of *Desulfovibrio, Desulfobacterium, Desulfobulbus, Desolfobacter, Desulfomicrobium, Desulfotomaculum*, and *Desulfococcus*.

8. The kit of claim 6, further comprising positive control probe of SEQ ID NO: 36.

9. The kit of claim 6, wherein the additional reagents or compositions comprise one or more of the following: sample buffer, reaction buffer, enzyme mix, Fragmentase reaction buffer, nucleotide mix, 1M GuSCN, 5 mM EDTA, or 50 mM HEPES.

* * * * *